(12) United States Patent
Swami et al.

(10) Patent No.: US 11,339,417 B2
(45) Date of Patent: May 24, 2022

(54) AMPLIFIER SYSTEM AND CONTROLS FOR DIELECTROPHORETIC TRACKING IN MICROFLUIDIC DEVICES

(71) Applicant: University of Virginia Patent Foundation, Charlottesville, VA (US)

(72) Inventors: Nathan Swami, Charlottesville, VA (US); Yi-Hsuan Su, Plano, TX (US); Cirle Alcantara Warren, Charlottesville, VA (US); Ali Rohani, Charlottesville, VA (US); Vahid Farmehini, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 399 days.

(21) Appl. No.: 15/515,528

(22) PCT Filed: Oct. 9, 2015

(86) PCT No.: PCT/US2015/055021
§ 371 (c)(1),
(2) Date: Mar. 29, 2017

(87) PCT Pub. No.: WO2016/057974
PCT Pub. Date: Apr. 14, 2016

(65) Prior Publication Data
US 2017/0218424 A1 Aug. 3, 2017

Related U.S. Application Data

(60) Provisional application No. 62/062,109, filed on Oct. 9, 2014.

(51) Int. Cl.
*B03C 5/00* (2006.01)
*B03C 5/02* (2006.01)
(Continued)

(52) U.S. Cl.
CPC ............... *C12Q 1/04* (2013.01); *B03C 5/005* (2013.01); *B03C 5/026* (2013.01);
(Continued)

(58) Field of Classification Search
CPC . C12Q 1/04; B03C 5/00–028; B03C 2201/26; G01N 33/56911; G01N 33/487;
(Continued)

(56) References Cited

U.S. PATENT DOCUMENTS

2003/0022466 A1* 1/2003 Escalera ............. H01L 21/8221
438/478
2004/0011650 A1 1/2004 Zenhausfem et al.
(Continued)

FOREIGN PATENT DOCUMENTS

JP 2008-245593 10/2008

OTHER PUBLICATIONS

Caldwell et al., High-Frequency Electronics for Contactless Dielectrophoresis, Virginia Polytechnic Institute and State University (2010) (Year: 2010).*
(Continued)

*Primary Examiner* — James Lin
*Assistant Examiner* — Vivian A Tran
(74) *Attorney, Agent, or Firm* — Meunier Carlin & Curfman LLC

(57) ABSTRACT

Systems, methods, and devices are described herein for identifying, monitoring, isolating, or selecting a cell having a predefined characteristic in a mixed population of cells utilizing a combination of any one or more of iDEP, a region of localized field enhancement, a variable frequency electric field, a wide bandwidth amplifier, and/or an imaging apparatus.

19 Claims, 23 Drawing Sheets

(51) Int. Cl.
*C12Q 1/04* (2006.01)
*G01N 33/569* (2006.01)
*G01N 33/487* (2006.01)

(52) U.S. Cl.
CPC .... *G01N 33/56911* (2013.01); *B03C 2201/26* (2013.01); *G01N 33/487* (2013.01); *G01N 2333/33* (2013.01)

(58) Field of Classification Search
CPC ... G01N 2333/33; B01L 2200/06–0694; B01L 2400/0406–0427; B01F 13/0001–001
USPC ...................................... 330/286, 295, 124 R
See application file for complete search history.

(56) References Cited

U.S. PATENT DOCUMENTS

| | | | |
|---|---|---|---|
| 2005/0158704 A1 | 7/2005 | Tyvoll et al. | |
| 2010/0224493 A1* | 9/2010 | Davalos | G01N 27/44791 204/547 |
| 2014/0367260 A1* | 12/2014 | Dickerson | B03C 5/028 204/547 |
| 2016/0193613 A1* | 7/2016 | Walti | B03C 5/005 204/547 |

OTHER PUBLICATIONS

LM7171, Texas Instruments (2014) (Year: 2014).*
Business Wire, Cirrus Logic Drives Piezoelectric Market With New Levels of Performance in Two New Single Package Solutions (2009) (Year: 2009).*
APEX Microtechnology, PA107DP Power Operational Amplifiers (2020) (Year: 2020).*
Kumar et al., Microfluidic Device for Conventional and Traveling-Wave Dielectrophoresis, NSTI-Nanotech, vol. 2, pp. 614-616 (2006) (Year: 2006).*
Ting et al., High Voltage Amplifier, Institute of Atomic and Molecular Sciences, IEEE, pp. 1247-1249 (2004) (Year: 2004).*
Lan et al, Design of wide-bind and multi-channel synchronous output driving power on dielectrophoresis, Applied Mechanics and Materials, vols. 427-429, pp. 1056-1059 (2013) (Year: 2013).*
Zellner, Three Dimensional Passivated-electrode Insulator-based Dielectrophoresis (3D PiDEP), Dissertation submitted to Virginia Polytechnic Institute and State University (2013) (Year: 2013).*
Braff, W.A., et al., "Dielectrophoresis-Bsed Discrimination of Bacteria at the Strain Level Based on Their Surface Properties," PLOS One, Oct. 2013, vol. 8, No. 10, 7 pages.
Chung, C.C., et al., "Screening of Antibiotic Susceptibility to β-Lactam-Induced Elongation of Gram-Negative Bacteria Based on Dielectrophoresis,", Analytical Chemistry, 2012, vol. 84, pp. 3347-3354.
Farmehini, V., et al., "A Wide-Bandwidth Power Amplifier For Frequency-Selective Insulator-Based Dielectrophoresis," Lab Chip, 2014, vol. 14, pp. 4183-4187.
Gascoyne, P., et al., "Correlations Between the Dielectric Properties and Exterior Morphology of Cells Revealed by Dielectrophoretic Field-Flow Fractionation," Electrophoresis, 2013, vol. 34, pp. 1042-1050.
Hawkins, B.G., et al., "Automated Dielectrophoretic Characterization of Mycobacterium Smegmatis," Analytical Chemistry, 2011, vol. 83, pp. 3507-3515.
Hoettges, K., et al., "Dielectrophoresis-Activated Multiwell Plate for Label-Free High Throughput Drug Assessment," Analytical Chemistry, 2008, vol. 80, pp. 2063-2068.
Jones, P.V., et al., "Differentiation of *Escherichia coli* Serotypes Using DC Gradient Insulator Dielectrophoresis,", Anal. Bioanan. Chem., 2014, vol. 406, pp. 183-192.
Rohani, A., et al., "Frequency-Selective Electrokinetic Enrichment of Biomolecules in Physiological Media Based on Electrical Double-Layer Polarization," Nanoscale, 2017, 8 pages.
Salmanzadeh, A., et al., "Isolation of Prostate Tumor Initiating Cells (TICs) Through Their Dielectrophoretic Signature," Lab Chip, 202, vol. 12, pp. 182-189.
Su, Y.H., et al., "Quantitative Dielectrophoretic Tracking for Characterization and Separation of Persistent Subpopulations of Cryptosporidium Parvum," Analyst, 2014, vol. 139, No. 1, pp. 66-73.
Su, Y.H., et al., "Tracking Inhibitory Alterations During Interstrain Clostridium Difficle Interactions by Monitoring Cell Envelope Capacitance," ACS Infectious Diseases, 2016, vol. 2, No. 8, pp. 544-551.
Unni, H.N., et al., "Characterization and Separation of Cryptosporidium and Giardia Cells Using On-Chip Dielectrophoresis," Biomicrofluidics, 2012, vol. 6, 15 pages.
Ratanachoo et al., "Detection of cellular responses to toxicants by dielectrophoresis," Biochim Biophys Acta. Aug. 31, 2002; vol. 1564, No. 2, Publication [online] Aug. 31, 2002, (retrieved Jan. 13, 2016). Retrieved from the internet: <URL:http://ncbi.nlm.nih.gov/pmc/articles/PMC2726261/>; pp. 449-458.
Rohani et al., "Electrical tweezer for highly parallelized electrorotation measurements over a wide frequency bandwith," Electrophoresis, Jul. 2014; vol. 35; (retrieved Jan. 13, 2016). Retrieved from the Internet: <URL:https://www.researchgate.net/publication/261105395>; pp. 1795-1802.
Weiss et al., "Dielectrophoretic mobility determination in DC insulator-based dielectrophoresis," Electrophoresis, Sep. 2011; vol. 32, No. 17, Publication [online]. Jan. 31, 2013 (retrieved Jan. 13, 2016). Retrieved from the Internet: <URL:http://www.ncbi.nim.nih.gov/pmc/articles/PM3517931/>; pp. 2292-2297.
International Search Report for related International Application PCT/US2015/055021, dated Jan. 14, 2016, 4 pages.

* cited by examiner

AMPLIFIER SYSTEM AND CONTROLS FOR DIELECTROPHORETIC TRACKING IN MICROFLUIDIC DEVICES

CROSS-REFERENCE TO RELATED APPLICATIONS

This application is a U.S. National Stage Application of and claims the benefit pursuant to 35 U.S.C. § 371 of, International Patent Application No. PCT/US2015/055021, filed Oct. 9, 2015, which claims priority to U.S. Provisional Patent Application No. 62/062,109, filed Oct. 9, 2014, the entire contents and substance of which are incorporated herein by reference in their entirety as if fully set forth below.

BACKGROUND

*Clostridium difficile* infection (CDI) is a toxin-mediated intestinal disease that is commonly attributed to exposure to pathogenic *Clostridium difficile* strains following the elimination of healthy microflora in the gut, due to administration of antibiotics. The incidence of CDI has exhibited a steady rise worldwide over the last two decades. With over 250,000 infections per year and 14,000 related fatalities per year nationwide, the CDC has judged that these infections are costing—$1 billion per year in health care costs. Prior studies within animal models strongly suggest that asymptomatic colonization with non-toxigenic *Clostridium difficile* (NTCD) strains can reduce the incidence of CDI from toxigenic *Clostridium difficile* (TCD) strains, and this preventive effect is substantiated within a meta-analysis of studies on hospitalized patients, as well as a phase 1 study that confirmed the ability of NTCD strains to colonize intestinal tracts of healthy human subjects pretreated with vancomycin. This has led to much interest towards reducing the incidence of CDI through pre-colonization with NTCD strains. The development of such preventive therapies against CDI requires means to monitor NTCD colonization during antibiotic and other therapeutic interventions, so that the antagonistic interactions between differing strains during co-infection can he characterized and optimized. However, there is no independent method to simultaneously monitor physiological alterations in both, NTCD and TCD strains, especially during antibiotic and therapeutic interventions. The standard of CDI diagnosis involves culture of the bacteria from stool samples and testing for toxin production levels (cytotoxicity assay). Given the time-consuming nature of toxigenic *C. difficile* culture, rapid diagnosis of CDI is usually accomplished by enzyme immunoassays (EIA) that can directly monitor TCD strains through detecting the glutamate dehydrogenase (GDH) levels, as well as that of toxin A (TcdA) and/or toxin B (TcdB) levels. However, this method is hampered by poor sensitivity due to rapid degradation of the toxins, thereby requiring its combined application with PCR to reduce false-positives and false-negatives. Furthermore, colonization by NTCD strains cannot be monitored by due to absence of the toxins, or by PCR-restriction fragment analysis of the pathogenicity locus (PaLoc) due to absence of the PaLoc within NTCD strains. Hence, there is a need for methods to simultaneously monitor the levels and physiological alterations of, for example, a *C. difficile* strain or other microbial strains within a mixed microbial sample, preferably in a label-free, non-destructive and real-time manner.

It is with respect to these and other considerations that the various embodiments described below are presented.

SUMMARY

In certain frequent embodiments, a method is provided for identifying a *Clostridium difficile* (*C. diff*) cell in a plurality of cells, comprising: exposing a plurality of *C. diff* cells in an analysis region to an electric field defined by a frequency to induce a change in each of the plurality of *C. diff* cells; imaging a position of a *C. diff* cell within the plurality of *C. diff* cells exposed to the electric field; calculating a velocity of the *C. diff* cell within the analysis region and conducting a comparison of the velocity with the frequency, and identifying the *C. diff* cell as toxigenic (TCD) or non-toxigenic (NTCD) based on the comparison.

Also, in certain frequent embodiments, methods are provided for identifying a cell exhibiting a characteristic in a mixed population of cells based on a dielectrophoretic spectra of the cell, comprising: exposing a plurality of cells in an analysis region that have or do not have the characteristic to an electric field defined by an applied frequency to induce a change in each of the plurality of cells; imaging a cell within the plurality of cells exposed to the electric field to identify a displacement of the cell at one or more different applied frequency defining the electric field, and identifying the cell as having the characteristic or not having the characteristic based on the displacement of the cell relative to the one or more different applied frequency. In a frequent embodiment, the cell comprises a *C. diff* cell.

In certain embodiments, a method is provided for identifying a TCD or a NTCD in a mixed population of cells based on a dielectrophoretic spectra of the TCD or NTCD, comprising: exposing a plurality of *C. diff* cells in an analysis region to an electric field defined by a frequency to induce a change in each of the plurality of *C. diff* cells; imaging a *C. diff* cell within the plurality of *C. diff* cells exposed to the electric field to identify a displacement of the *C. diff* cell at one or more different applied frequency defining the electric field, and identifying the *C. diff* cell as TCD or NTCD based on the displacement of the *C. diff* cell relative to the one or more different applied frequency.

Often, the frequency is defined by a frequency range between 0 kHz to about 40 MHz. Also often, the electric field is a 20V to 1000V field.

The electric field is frequently generated in an insulator or electrode-less dielectrophoresis device (iDEP). The insulator dielectrophoresis device often comprises, for example, an insulator constriction, insulator constrictions, or another nano-device or nano-feature provided to enhance localized electric fields in the presently described methods, systems, and devices.

In certain embodiments, the *C. diff* cell, or other cell such as a target cell obtained from a sample, is imaged while the frequency is shifted in magnitude. Often, the frequency is shifted from about 100 kHz to about 1 MHz. In certain embodiments, the cell is imaged while the frequency is shifted to evaluate, confirm, or monitor an electrophoretic spectra of the cell. Often, the frequency of the electric field is shifted or changed between a lower and a higher frequency during imaging. According to the present methods, a crossover frequency for the target cell such as a *C. diff* cell is identified. Often, the frequency is selected from the group consisting of 400 kHz, 500 kHz, 600 kHz, 900 kHz, or a combination thereof. Also often, the frequency is selected from the group consisting of 100 kHz, 200 kHz, 300 kHz, 400 kHz, 500 kHz, 600 kHz, 700 kHz, 800 kHz, 900 kHz, 1000 kHz, or a combination thereof. A cross-over frequency for a cell, often referred to as an electrophoretic spectra or characteristic of an electrophoretic spectra for the cell, often lies in these frequencies.

In certain frequent embodiments a method is utilized to determine an efficacy of an antibiotic or the presence of certain cell types or populations in the sample after use or introduction of an antibiotic. In frequent embodiments, the antibiotic is vancomycin, though other antibiotics are contemplated. Often, the *C. diff* cell is identified as a hypervirulent TCD cell, a less virulent TCD cell, or an NTCD cell based on the comparison. Frequently, the frequency to induce a change in each of the hypervirluent TCD, less virulent TCD, and NTCD according to the presently described methods is a different frequency. In certain embodiments, the change in the cell comprises a polarization of certain components or aspects of the cell as further described herein. In certain embodiments, the change in the cell comprises movement of the cell across or within a medium. In certain embodiments, other cellular changes described and contemplated herein are considered as a change in the cell according to the present methods.

In frequent embodiments, an antibiotic is administered to one or more of the plurality of *C. diff* cells prior to imaging. Often, each of the plurality of cells is imaged after administration of the antibiotic. Also often, each of the plurality of cells is imaged, the velocity of each is calculated, and the comparison is conducted for each, after administration of the antibiotic. Often, the *C. diff* cell is imaged in the presence of an insulator constriction (or other device or feature contemplated herein to provide localized field enhancement) positioned within the electric field.

In certain limited embodiments, an immunoassay agent (a labeled antibody or labeled portion or labeled fragment thereof) is not contacted with the target cell such as a *C. diff* cell prior to imaging. In certain embodiments immunological agent is provided as a capture reagent.

Often, the characteristic of the cell comprises virulence, pathogenicity, toxicity, or a combination thereof. Also often, the characteristic of the cell comprises toxin producing membrane presence.

In certain frequent embodiments, a system is provided for identifying, monitoring, and/or selecting or isolating a live cell having a predefined characteristic in a mixed population of cells, comprising: an analysis region defined by an electric field having a frequency and an insulator constriction; a cell culture media region positioned within the analysis region; and an imaging apparatus adapted to image the analysis region and identify or monitor the live cell having the predefined characteristic in a mixed population of cells based on the frequency of the electric field. Often, the predefined characteristic comprises virulence, pathogenicity, toxicity, or a combination thereof. Also often the characteristic comprises toxin producing membrane presence. Frequently, the cell comprises a *C. diff* cell.

Often, the present systems, the mixed population of cells comprises a mixed population of toxigenic and non-toxigenic cells, such as *C. diff* cells. Often, the cell culture media region comprises a cell culture agent that is not specifically adapted for electrophoreic analysis. When a *C. diff* cell or cell culture is being analyzed, *C. diff* cell culture media is often utilized.

In frequent embodiments, the imaging apparatus is operably connected with a processor. Often, the processor is adapted to extract position information related to the cell in the cell culture media region captured in multiple images. Also, often the processor is adapted to calculate a velocity or rate or movement or displacement of the cell using the position information captured in multiple images.

Often, the imaging apparatus comprises a camera. Frequently, the imaging apparatus comprises a differential interference microscope.

In frequent embodiments, a wide bandwidth amplifier for single particle tracking is provided, comprising: a paired and counter-phase coupled amplifier unit comprising a first and a second amplifier and a wideband splitter unit adapted to provide counter-phase signals to each of the first and second amplifier; and an adjustable power supply operably connected with the amplifier unit.

Often, the amplifier unit is operably connected with an insulator electrophoresis device.

In frequent embodiments, the first and second amplifier are provided with counter phase signals of the same amplitude. Often, the first and second amplifier are each operational amplifiers (Op-amps). Also often, the splitter unit comprises a super-fast low-power Op-amps. The adjustable power supply often comprises an attenuator. In frequent embodiments, the amplifier has a slew rate of over 2500 V/μs. Often, the amplifier has a slew rate of over 3000 V/μs. Also often, the amplifier has a slew rate of about 4000 V/μs. In a frequent embodiment, the amplifier has a slew rate of about 5000 V/μs.

In certain embodiments a system is provided for identifying or monitoring a live cell having a predefined characteristic in a mixed population of cells, comprising an analysis region defined by an electric field generated by the amplifier or amplifier unit described herein; an optional cell culture media region positioned within the analysis region; and an imaging apparatus adapted to image the analysis region and identify or monitor the live cell having the predefined characteristic in a mixed population of cells based on a frequency of the electric field. Often, the analysis region comprises an insulator constriction (or other device or feature contemplated herein to provide localized field enhancement).

While an imaging apparatus is exemplified as a frequently preferred mode of obtaining and monitoring data related to a target cell, the present disclosure is not intended to be so limited. In particular, other modes of data collection relevant to identifying a cell having a pre-determined characteristic identifiable through the DEP and iDEP-related methodologies described herein are contemplated. Similarly, imaging of a cell may occur after it is isolated or selected using the DEP and iDEP-related methodologies and devices described herein.

These and other embodiments, features, and advantages will become apparent to those skilled in the art when taken with reference to the following more detailed description of various exemplary embodiments of the present disclosure in conjunction with the accompanying drawings.

BRIEF DESCRIPTION OF THE DRAWINGS

The skilled person in the art will understand that the drawings, described below, are for illustration purposes only.

DETAILED DESCRIPTION OF THE VARIOUS EMBODIMENTS

Figure 1:
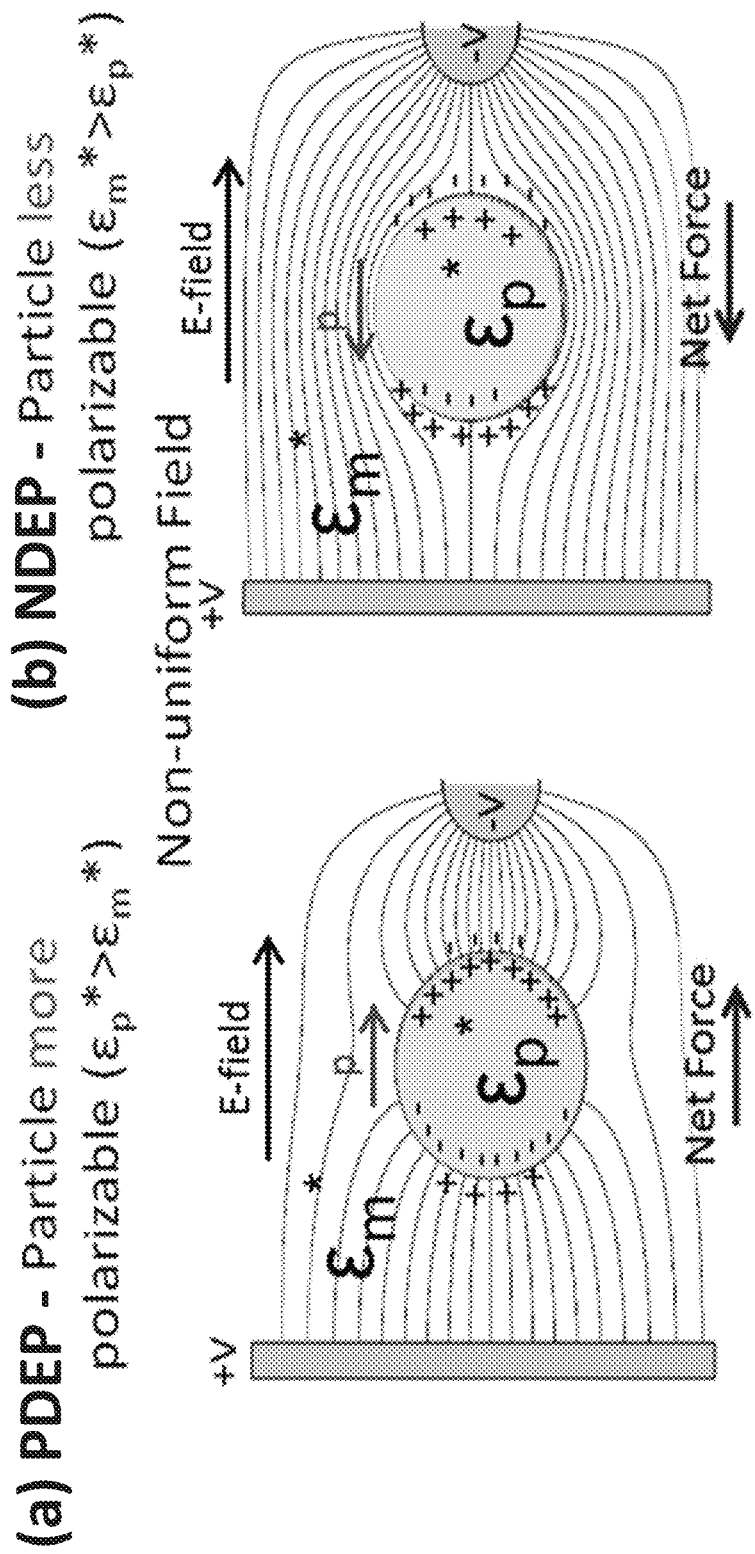
FIG. 1 depicts the localization of cells due to polarization at a characteristic frequency under a non-uniform field causes trapping at or away from high field points: (a) positive DEP (PDEP); (b) negative DEP (nDEP).

For clarity of disclosure, and not by way of limitation, the detailed description of the various embodiments is divided into certain subsections that follow.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, the term "and/or" may mean "and," it may mean "or," it may mean "exclusive-or," it may mean "one," it may mean "some, but not all," it may mean "neither," and/or it may mean "both."

As used herein, "subject" often refers to an animal, including, but not limited to, a primate (e.g., human). The terms "subject" and "patient" are used interchangeably herein.

As used herein, the terms "detect," "detecting," or "detection" may describe either the general act of discovering or discerning or the specific observation of a cell, molecule, or composition, whether directly or indirectly labeled with a detectable label.

As used herein, "insulator constrictor" or "insulator constriction(s)" refers to a specific insulator constriction, or a device or a feature (e.g., a nano-device or nano-feature) of a device or system described herein provided to enhance localized electric field strength.

As used herein, the term "displacement" is used interchangeably with "movement," except where specifically indicated.

As used herein, the phrase "live cell" refers to an intact cell that maintains activity of at least a portion of its typical intracellular processes or extracellular reactions. Typically, "live cell" excludes lysed or fixed cells.

As used herein, "sample" refers to any substance containing or presumed to contain a cell of interest or a cell for investigation. The term "sample" thus includes a cell, organism, tissue, fluid, or substance including but not limited to, for example, blood, plasma, serum, spinal fluid, lymph fluid, synovial fluid, urine, tears, stool, external secretions of the skin, respiratory, intestinal and genitourinary tracts, saliva, blood cells, tumors, organs, tissue, samples of cell culture constituents, natural isolates (such as drinking water, seawater, solid materials), microbial specimens, cell lines, and plant cells. Often, a target cell is present or suspected to be present in a sample.

The following detailed description should be read with reference to the drawings. The drawings, which are not necessarily to scale, depict selected embodiments and are not intended to limit the scope of the present disclosure. The detailed description illustrates by way of example, and is not intended to limit the scope of the present disclosure.

Current methods using animal models and cytotoxicity cell culture assays provide only an indirect assessment of CDI, and the time consuming procedures of these current methods limit the permutations for the study of interactions between strains across the microbiome. Moreover, while enzyme immunoassays (EIAs) can directly monitor TCD strains through tracking the production of toxin A (TcdA) and toxin B (TcdB), they can yield false negative results due to the rapid degradation of these toxins. Moreover, since NTCD strains do not produce these toxins, alterations of NTCD strains due to interactions with TCD strains cannot be monitored, in parallel, by EIAs.

The present disclosure sets forth, among other things, a microfluidic device (and related method) to fingerprint different strains of *Clostridium difficile* (*C. diff*) based on their unique electrophysiology and phenotype, which causes characteristic shifts in the dielectrophoretic (DEP) frequency spectra of the respective microbial strains. Specifically, based on automated and simultaneous tracking of the dielectrophoretic translation of single microbial cells under a frequency modulated electrical field, the present disclosure provides a label-free methodology to independently characterize the electrophysiology of particular subpopulations of cells within a mixed culture. As a result, the characteristic features of cell subpopulations on the dielectrophoretic frequency spectra can be applied to monitor interactions between toxigenic and non-toxigenic *C. diff.* strains under varying nutrient and environmental conditions. Finally, this probe can also be applied to study interactions between microbial strains within heterotypic microbial cell culture environments constructed on a microfluidic device to simulate the interactions within a nutrient ecosystem.

Dielectrophoresis

Microbial samples are usually spread over a range of species, strains and developmental lifecycles, so that their viability and functionality are determined by the microbiota. The resulting interactions can cause highly heterogeneous modifications, which poses challenges towards the sensitive, selective and quantitative monitoring of alterations in the microbial strain of interest. Dielectrophoresis (DEP) causes frequency-selective translation of polarized bio-particles in a non-uniform field, either towards or away from high field regions within a device, depending on the polarizability of the bio-particle versus that of the medium as exemplified in FIG. 1. See also T. B. Jones, Cambridge University Press, Cambridge, N.Y., 1995; N. G. Green and Hywel Morgan, USA: Research Studies Press Ltd., First edn., 2002.

At low frequencies (10-500 kHz), the polarization is determined by field screening caused by the cell wall and membrane, thereby leading to negative DEP (nDEP), whereas at high frequencies (0.5-2 MHz), the polarization is determined by the cell cytoplasm and nucleus, thereby leading to positive DEP (pDEP). See R. Pethig, *Biomicrofluidics,* 2010, 4. For a given cell phenotype and electrophysiology, this leads to a characteristic DEP force dispersion ($F_{DEP}$) and crossover frequency from nDEP to pDEP, as per Eq. (1):

$$F_{DEP} = \underbrace{2\pi a^3}_{size/shape} \varepsilon_m \mathrm{Re}\underbrace{\left(\frac{\overbrace{\varepsilon_p^* - \varepsilon_m^*}^{Electrophysiology}}{\varepsilon_p^* + 2\varepsilon_m^*}\right)}_{K_{CM}} \underbrace{\nabla E^2}_{geometry} \qquad \text{Eq. (1)}$$

Here, a: is particle radius and includes information on particle shape; $E_m$: is the medium permittivity; $K_{CM}$: is the Clausius-Mossoti factor or contrast between particle and media polarizability, and $\nabla E^2$: is the product of the localized field to its gradient, which displays dependence on device geometry.

Quantitative measurements of the frequency-selective translation of particles can be utilized to enrich a particular microbial strain and to selectively measure alterations to its structure, either due interactions across the microbiome that cause environmental or nutrient alterations or due to antibiotics that can cause heterogeneous microbial modifications because of the varying susceptibility of subpopulations. Current DEP methods to monitor microbial electrophysiology and phenotype include:

(a) Collection rate method that measures the DEP collection rate of a particular cell type over a frequency range to track the force dispersion. See D. J. Bakewell and H. Morgan, *Meas Sci Technol,* 2004, 15, 254-266. This method is accurate only when the DEP forces are substantial and when the localization regions for pDEP versus nDEP are well separated spatially across the device.

(b) Crossover frequency method measures the frequency for crossover from nDEP to pDEP for a particular microbial strain at different media conductivity values ($\sigma_m$), which is used to set the $K_{CM}$ to zero for extracting the electrophysiological microbial properties, using a least-square fit See Z. Gagnon et al., *Electrophoresis,* 2008, 29, 2272-2279; Z. Gagnon et al., *Biomicrofluidics,* 2009; M. Castellarnau et al., *Biophysical journal,* 2006, 91, 3937-3945. The drawback of this method is that its accuracy depends on having crossover frequency measurements over a range of $\sigma_m$; however, cells exhibit positive and negative DEP over a range of only limited $\sigma_m$ values.

(c) Levitation voltage method measures the minimum voltage required to levitate the cells under nDEP from an electrode to thereby generate the force response. See K. V. Kaler and T. B. Jones, *Biophysical journal,* 1990, 57, 173-182. This method does not work with cells exhibiting pDEP only.

As with all of these methods, since the force values are averaged over a collection region, measurements do not exhibit single-cell sensitivity. This presents a drawback while measuring the DEP response of fractional microbial subpopulations that are antibiotic resistant or altered by environmental interactions. As described herein methods and devices are provided that address each of these existing problems and drawbacks by applying, for example, a microfluidic device for initiating frequency-selective dielectrophoresis and measuring their translation in an automated manner, with single-cell sensitivity.

Figure 2:
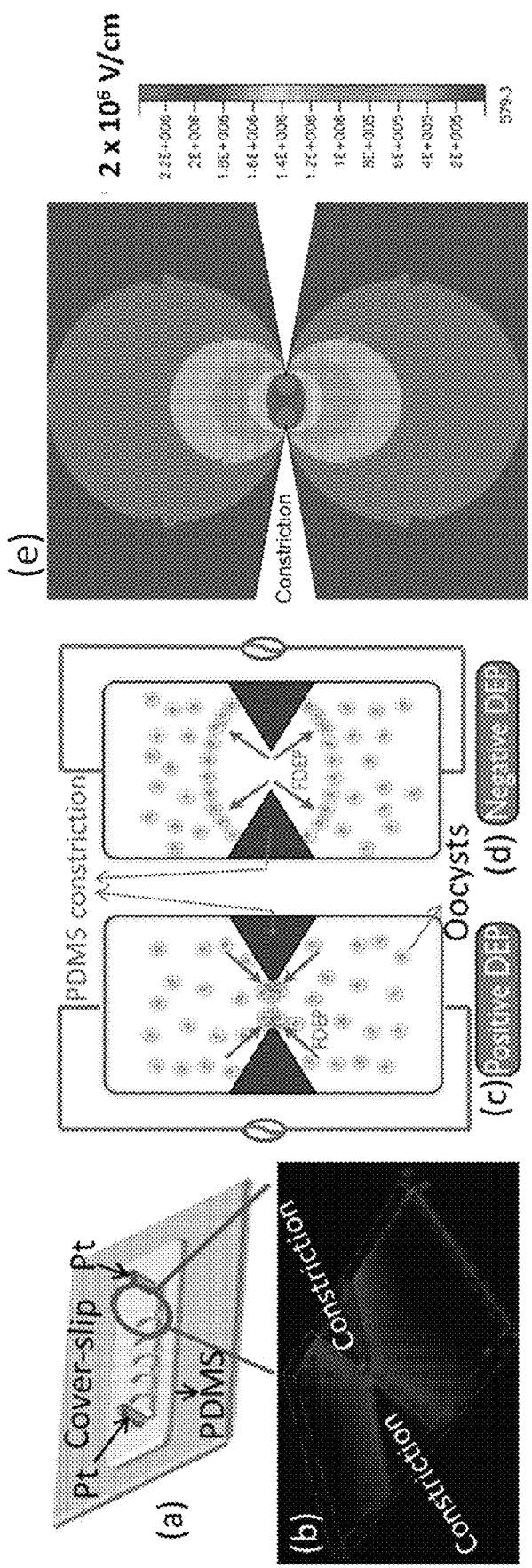
FIG. 2: Electrode-less DEP devices (a & b) showing localization under pDEP (c) and nDEP (d), due to localized enhancement of the field and its gradient (e)

In the present disclosure a non-uniform electric field to initiate DEP behavior is often applied in an "electrode-less" format. For example, hollow cylindrical Pt tubular electrodes are provided in the inlet and outlet regions (FIG. 2a) leading up to the several parallel channels (~1 mm wide) are utilized to apply the non-uniform AC field and microscale insulator constrictions (~15-20 gm gap) within the channels (FIG. 2b) are utilized for trapping the microbial cells due to bending of field lines (FIG. 2e). In this manner, microbial cells are not trapped at the electrodes where they may be destroyed due to the applied voltage and electrochemical reactions, but instead they are trapped at or away from the tips of insulator constrictions (FIGS. 2c & 2d), where there is no destruction due to absence of a pathway for current passage. See N. Swami et al., *Lab on a Chip,* vol. 9, p. 3212-3220, 2009. Furthermore, while media conductivity ($\sigma_m$) is typically lowered in electrode-based devices to enable the necessary field for DEP behavior by limiting the influence of double-layerscreening and electrolysis effects, this is not required within electrode-less devices, since electrolysis effects do not disrupt DEP behavior in this design, due to localization of trapping away from the electrodes. As depicted in FIG. 2e, localized fields due to a sharp insulating constriction are 2-3 orders of magnitude higher than the applied fields, thereby enabling trapping at significantly lower voltages and within media of significantly higher $\sigma_m$. See K. Liao et al., *Electrophoresis, vol.* 33, pp. 1958-1966, 2012. As such, DEP measurements can be carried out within the physiological media used for microbial culture, thereby enabling the real-time monitoring of interactions of multiple microbial strains within a mixed culture.

Exemplary microfluidic devices contemplated herein, including their manufacture, use, and results obtained therewith are further described herein.

Quantitative Dielectrophoretic Tracking with Single-Cell Sensitivity for Automated Monitoring of the Electrophysiology of Multiple Cells in Parallel The capability of DEP for frequency-modulated characterization of microbial cells, with selectivity to the properties of the cell wall or membrane at low frequencies and to the properties of the cytoplasm and nucleus at high frequencies, can enable electrophysiological monitoring without the need for chemical labeling or wash steps. Furthermore, this frequency-selective DEP behavior can be applied to the separation and enrichment of particular microbial strains due to their spatial localization based on their characteristic DEP spectra, thereby enabling the quantification of their heterogeneous modification by antibiotics or due to interactions across the microbiome. For this purpose, the present disclosure describes and exemplifies continuously tracking the time evolution of displacement of the oocysts, for example, under DEP behavior within an exemplary constriction microfluidic device. See FIG. 2. Prior methods have used interdigitated or quadrapole electrode devices to track the collection rate or velocity of polarized bio-particles under dielectrophoresis. See F. H. Labeed et al., *Bba-Gen Subjects,* 2006, 1760, 922-929; H. Watarai et al., *Langmuir,* 1997, 13, 2417-2420.

Figure 3:
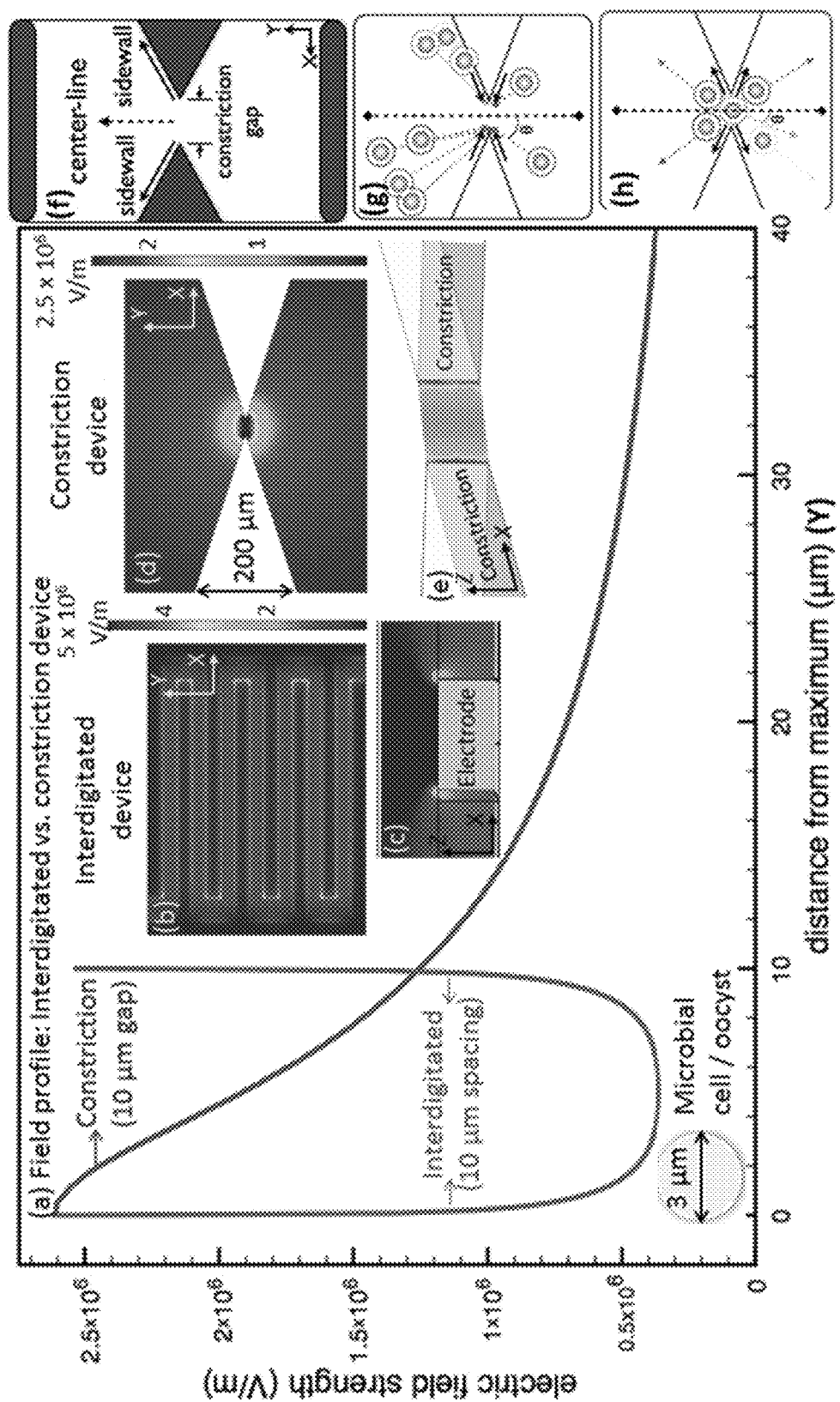
FIG. 3: Shows an effect of a field profile on dielectrophoretic tracking: (a) the sharp profile in the lateral direction of interdigitated (also in (b)) versus tapered profile in the constriction device (also in (d)), especially on the scale of a typical cell or oocyst, allows observation of more displacement (or movement) versus time points for the constriction device. The symmetric depth profile of the field for the constriction device (e) versus the highly non-uniform profile in the interdigitated device (c) ensures that the DEP trapping force has a similar effect on all particles across the depth in the former device. (f) Constriction device enables facile and simultaneous tracking of single oocysts under: (g) positive DEP; and: (h) negative DEP.

The chief disadvantage of devices with electrodes for quantifying the DEP behavior is that since electric field lines must terminate normal to the electrode surface, the degree of spatial control of the field gradient across the lateral and depth directions is rather limited. As per FIGS. 3a and 3b, the sharp field non-uniformity laterally from 10 gm spaced interdigitated electrode edges will cause polarized bio-particles to be abruptly accelerated, only in close proximity of the electrode edge. Hence, under positive DEP, this sharp field profile often does not allow for recording of significant displacement versus time points, especially for microbial and mammalian cells that extend over several microns. Furthermore, as depicted in FIG. 3c, the field non-uniformity vertically from the electrode causes differential influence of the field across the device depth. As a result, displacement tracking to quantify the DEP response is not accurate. While collection rate measurements can enable quantification, they will require averaging over a large region due to the ill-defined trapping region, which will make the data less sensitive to variations from fractional subpopulations. Quantifying negative DEP behavior presents even greater problems since the polarized bio-particles are translated along the device depth. While confocal microscopy can quantify the final position under negative DEP, active tracking at high frame rates is not possible.

In this context, the insulator constriction within the microfluidic device described herein (see, e.g., FIG. 2) provides an unprecedented degree of spatial control of the field to define the trajectory of the polarized bio-particles under both, positive and negative DEP. First, the high-field point is localized at the constriction tip and the gradient is modulated over a specified spatial extent of ~50 gm, as shown in FIGS. 3a and 3d. Hence, the trajectory of polarized bio-particles is well-defined, for example, from the beginning of a field gradient to a constriction tip under positive DEP (FIG. 3g); and/or from a constriction tip to the end of a field gradient under negative DEP (FIG. 3h). Furthermore, since the constriction is most frequently provided uniformly across the device depth, the field profile in such embodiments is symmetric across the depth (FIG. 3e). Therefore, polarized bio-particles in the device and within the vicinity of the field gradient are influenced uniformly due to the constriction, irrespective of their position within the device depth; whereas the differences in trapping force due to the lateral field non-uniformity can be normalized by the field gradient (FIG. 3d) along a particular trajectory. In this manner, since the particle trajectory is highly defined under both, positive and negative DEP, the displacement versus time data of individual bio-particles can be simultaneously measured in a facile manner by image analysis, without the need for averaging of the data from multiple bio-particle collection measurements over a large region. This enhances the sensitivity of our measurements towards small differences in electrophysiology of subpopulation.

Ability to independently monitor toxigenic and non-toxigenic C. diff strains by probing alterations to their cell electrophysiology based on shifts in their DEP spectra: Applying the automated tracking method described herein with specific operational amplifiers (OP-AMPs) designed to reduce charging time by reducing junction capacitances, the voltage output is frequently enhanced to 300-500$V_{pp}$ over a wide frequency bandwidth (10 kHz to 10 MHz) for obtaining quantitative DEP spectra.

Figure 4:
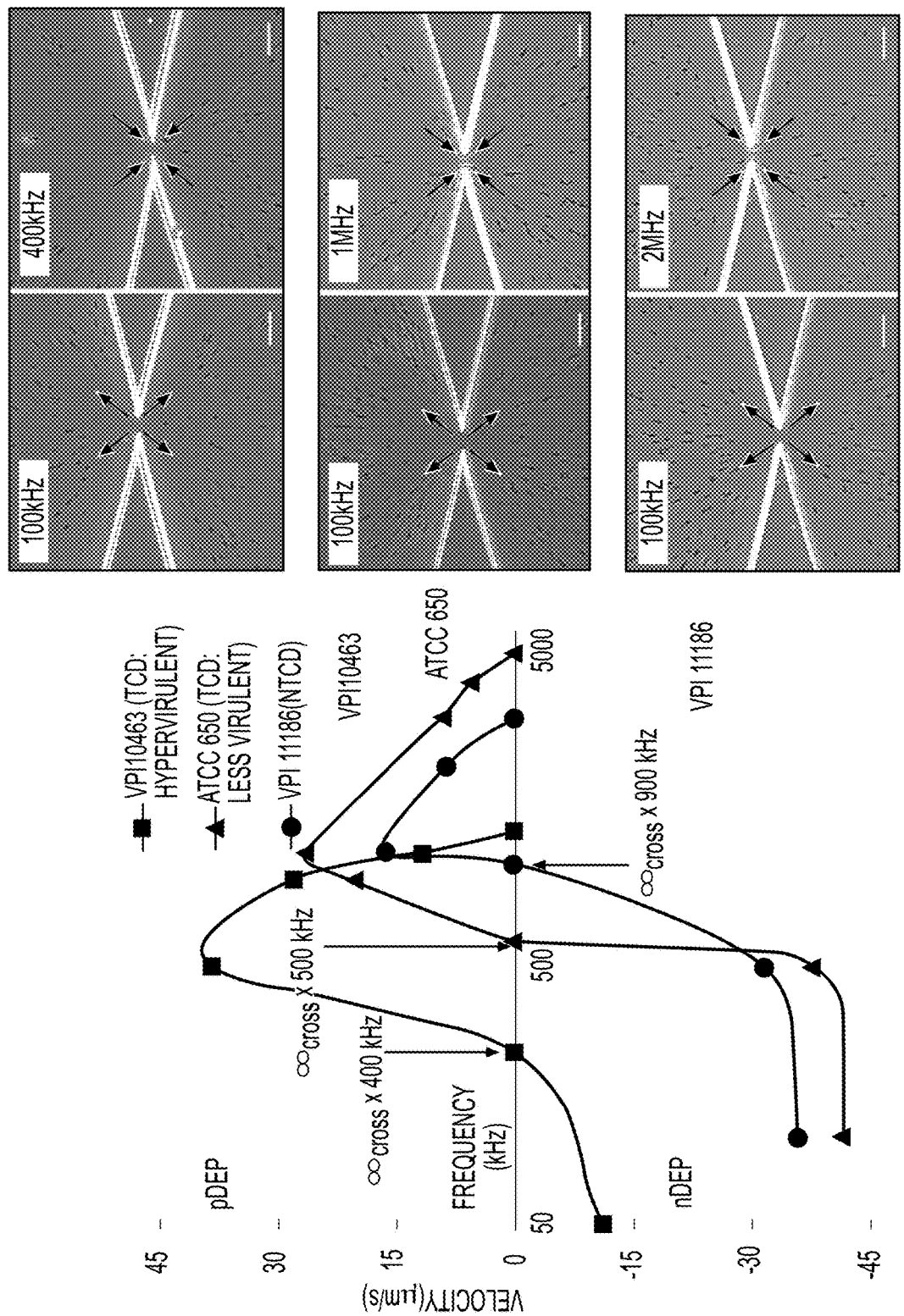
FIG. 4: Well-separated DEP spectra (velocity under FDEP) for TCD (VPI10463), TCD (ATCC 630) & NTCD (VPI11186) strains for simultaneous viability measurement FIG. 5:(a) (top) Modification of DEP spectra (velocity under FDEP) can be used to monitor alterations after antibiotic treatment of toxigenic and non-toxigenic C. diff (TCD & NTCD) in a quantitative, label-free and real-time manner. (b) (bottom) Drop in microbial growth rate confirms alterations due to antibiotic treatment.

In FIG. 4, this capability is exemplified in the acquisition of DEP spectra of toxigenic and non-toxigenic C. diff (TCD and NTCD) strains. The DEP spectra of the NTCD strain shows a crossover from nDEP to pDEP behavior at 900 kHz, with pDEP response thereafter until 3 MHz, whereas the crossover for less virulent and hypervirulent TCD strains are at successively lower frequencies of 500 kHz and 400 kHz, respectively. One important difference between TCD and NTCD strains for purposes of the present disclosure is the missing Pathogenecity Locus (PaLoC) within the genome of the non-toxigenic strains (NTCD VPI11186), which leads to absence of the toxin producing membrane protein: TcdE. The present disclosure attributes observations on the systematic down-shifting in DEP crossover frequency with increasing TcdE level (non-toxigenic to medium toxigenic to highly toxigenic strains) to the electrophysiological alterations that accompany the successive enhancement of membrane conductance with increasing toxin production due to their TcdE levels. The well-separated spectra for each strain and the correspondence of DEP crossover to toxin production level is often applied towards independent characterization of each strain within heterogeneous samples and its correlation to toxin production.

Though not wishing to be bound to any particular theory, DEP spectra depend on inherent dielectric properties of a particle versus the media where the particle is located. As detailed herein, DEP spectra can be utilized to fingerprint a particular microbial strain, as well as to probe its modification due to antibiotic treatment or environmental (or nutrient) alterations from interactions between strains.

Figure 5A:
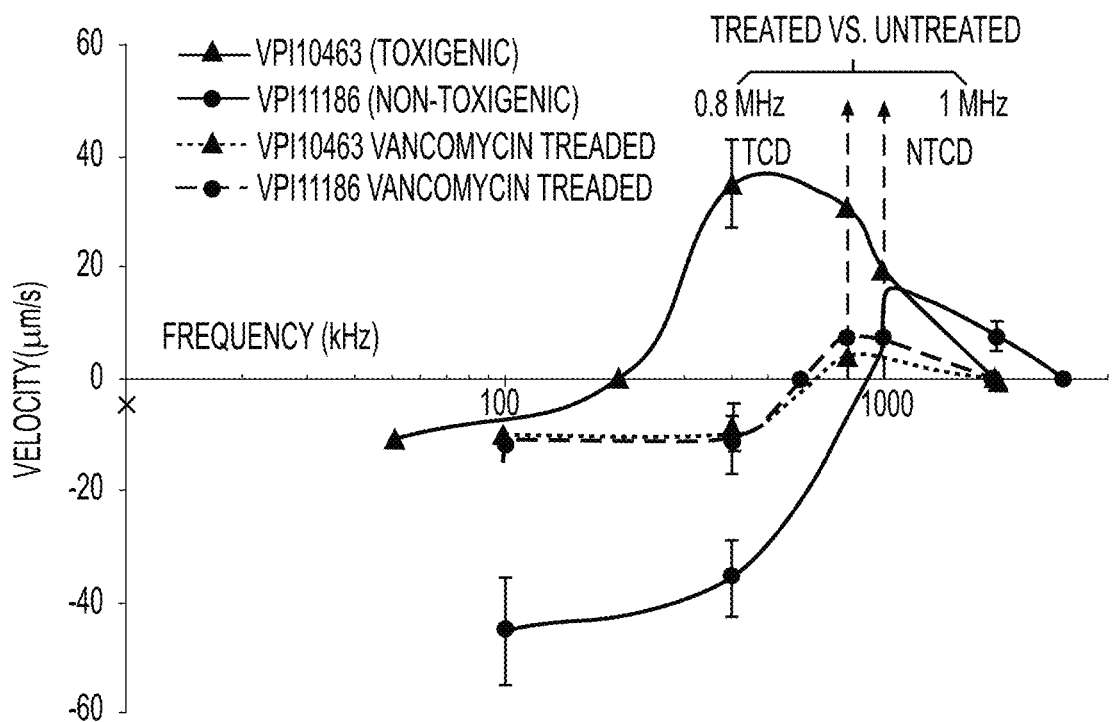
Figure 5B:
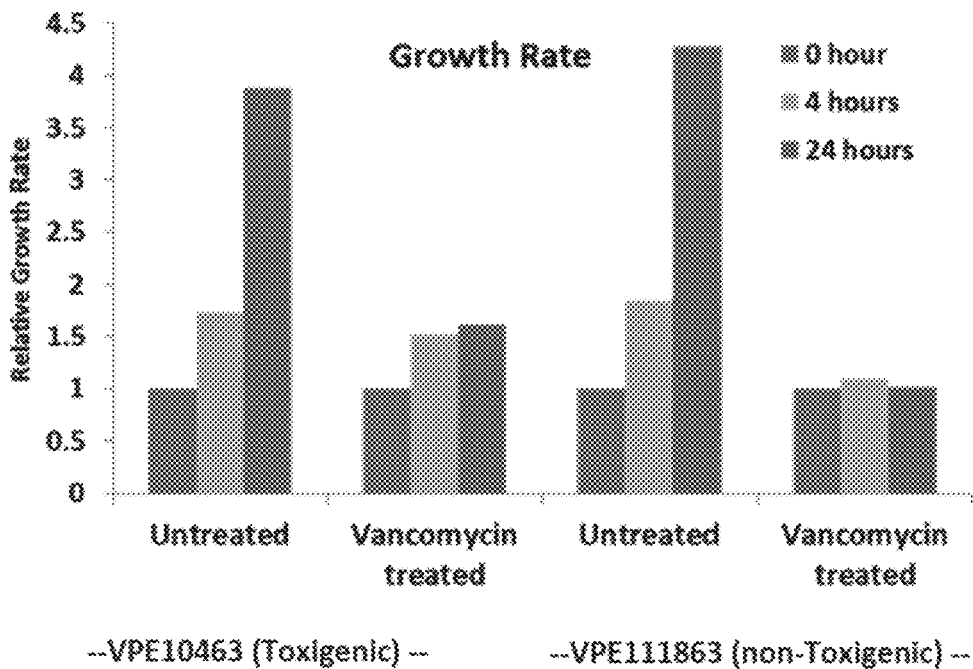

As depicted and exemplified in FIG. 5, the DEP spectra can distinguish the change of electrophysiology in the TCD and NTCD strains after antibiotic treatment with vancomycin. Overall, after antibiotic treatment the microbial cells of all strains become less polarizable due to functionality alterations of the cell. Furthermore, the DEP crossover frequency of the hypervirulent TCD strain (solid line with triangle markers) is shifted from 400 kHz to 900 kHz after vancomycin treatment (dashed line with triangle markers), while that of the NTCD strain (solid line with diamond markers) is shifted from 900 kHz to 600 kHz. While these alterations in DEP spectra are apparent initially and rapidly after antibiotic treatment, the alterations in microbial growth rate before and after antibiotic treatment are only barely distinguishable after 4 hours of treatment (FIG. 5b), while treatment for 24 hours confirms the alterations. Similarly, the present disclosure correlates the DEP velocity level at 800 kHz for the untreated versus antibiotic treated TCD strain to its toxin production level, as determined by the immunoassay.

Figure 6A:
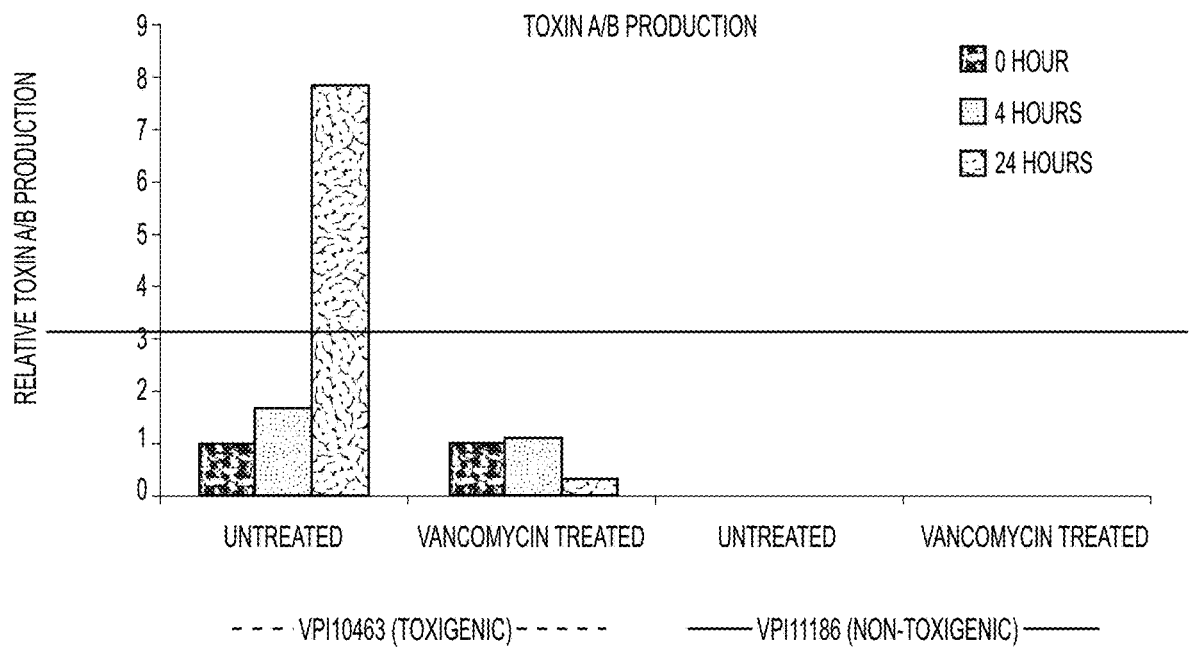
FIG. 6:(a) (top) Antibiotic treatment causes the reduction of toxin production for the TCD strains. (b) (bottom) This reduction correlates with the alteration DEP velocity.
Figure 6B:
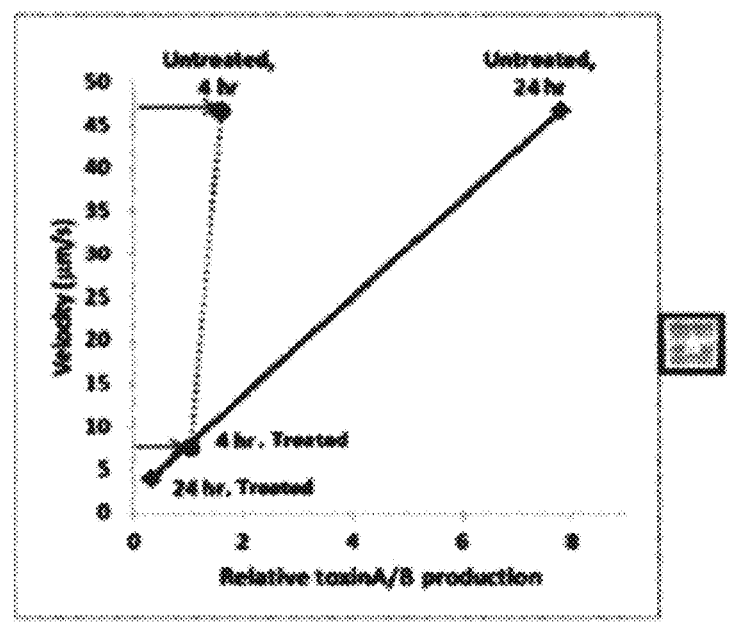

As depicted in FIGS. 6a & 6b, the DEP velocity correlates linearly with the toxin production level for TCD strains after varying treatment time points. In particular, the higher sensitivity of the DEP methods described herein compared with immunoassays to monitor microbial alterations is apparent, for example, from the observation that while the differences in toxin production level before and after vancomycin treatment for 4 hours (dotted line) are only barely distinguishable (arrows), the DEP velocity differences (Y-axis) on the same samples are substantial. For the NTCD strain, since there is no toxin production before or after antibiotic treatment, though not wishing to be bound by any particular theory, the drop in DEP velocity at 1 MHz (or the downshifting of the DEP crossover frequency) is correlated to the drop in microbial growth rate after antibiotic treatment. In summary, the DEP spectra of the TCD and NTCD strains correlates quantitatively with conventional probes of C. diff alteration after antibiotic treatment, such as utilizing the microbial growth rate and is more sensitive than the conventional probes.

Microfluidic Device for Heterotypic Cell Culture to Study the Microbiome Interactions Within Heterogeneous Samples The microfluidic device described herein is well suited for characterizing the interactions between C. diff strains, among other microbial strains, within a heterogeneous sample. For instance, the introduction of TCD strains to a nutrient niche pre-colonized by an NTCD strain will cause systematic alterations in the electrophysiology, viability and heterogeneity of the NTCD, as well as the TCD microbial strains within the mixed culture. The well-separated DEP spectra of NTCD versus the TCD strains (see, e.g., FIG. 4) provides a way to simultaneously characterize both types of strains within a mixed culture, as well as to separate and enrich each strain type, for independent monitoring their respective growth curves. The data, for example, in FIGS. 5 and 6 confirm that the alteration in the DEP spectra of the respective strains correlates with conventional probes of C. diff alteration after antibiotic treatment. The effect of interactions within the microbial nutrient microenvironment will be characterized by measuring the DEP spectra of each C. diff strain on this microfluidic device platform, to measure the histogram of $F_{DEP}$ and $U_{cross}$ on single cells. To measure the force response on individual cells, an automated particle tracking algorithm to monitor the displacement (x) of the cell over time (t) under nDEP or pDEP, using images from high frame per second (e.g., 30-100 fps) movies is often applied to compute FDEP using Eq. (2):

$$F_{DEP} - 6\pi n\alpha \frac{dx}{dt} = m\frac{d^2x}{dt^2} \qquad \text{Eq. (2)}$$

The FDEP data averaged over multiple cells can be fit to a shell model to compute alterations in conductivity and permittivity of the cell membrane and cytoplasm. Within heterogeneous microbial samples, a histogram from $U_{cross}$ on single cells will be plotted, so that viability changes can be monitored based on the mean, while the standard deviation provides information on the heterogeneity due to interactions between the strains.

Current methods using animal models and cytotoxicity cell culture assays provide an indirect assessment of CDI, and their time consuming procedures limit the permutations for the study of inter-species interactions. While enzyme immunoassays (EIAs) can directly monitor TCD strains through tracking toxin production (e.g., TcdA and TcdB), they can cause false negatives due to the rapid degradation of these toxins. Furthermore, since NTCD strains do not produce these toxins, their alterations due to interactions with TCD strains cannot be monitored, in parallel, by EIAs. Finally, while PCR-restriction fragment analysis of the pathogenicity locus (PaLoc) can sensitively identify the respective strains, it mainly detects the tcd and cdu genes located on the PaLoc; hence, it cannot directly monitor NTCD strains. Furthermore, nucleic acid extraction procedures can be cumbersome, destructive and not well suited for real-time monitoring.

In contrast, DEP spectra described herein, which occur, at least in part, due to a characteristic frequency dependence of the dielectric properties (e.g., conductivity and permittivity) of a particular microbial strain versus those of the media, can fingerprint the particular microbial strain and enable its separation from other closely-related strains. More specifically, the present methods are often provided for real-time monitoring of interactions through simultaneously gauging alterations in viability and heterogeneity of each microbial strain. In summary, the present disclosure provides, among other things, a microfluidic device methodology (and related system) to simultaneously monitor the alterations within multiple microbial strains such as *C. diff* strains, with single-cell sensitivity, to gauge the effect of antibiotics or the nutrient microenvironment due to interactions between, for example, TCD and NTCD strains.

Wide Bandwidth Amplifier and Frequency-Selective iDEP

Insulator-based dielectrophoresis, as described herein, provides contact-less separation and analysis of biosystems. However, due to certain limitations in the system, at present, its operation in the MHz frequency range is often inefficient. Operation in such frequency ranges is often important for the manipulation of biological cells based on the characteristic electrophysiology of their cytoplasm or biomolecular preconcentration based on their unique conformation. To address the steep drop in output power and the rise of signal distortions within conventional amplifiers at MHz frequencies due to slew rate limitations, design details and principles are provided herein for an exemplary wideband amplifier. This exemplary wideband amplifier provides, for example, an absence of harmonic distortions and parasitic DC within the amplifier output up to 15 MHz, thereby enabling analysis of cytoplasmic alterations on exemplary oocysts of *Cryptosporidium parvum*, due to constant force dispersion in the MHz range.

Dielectrophoresis provides frequency-modulated manipulation of polarized bio-particles under a spatially non-uniform electric field and is widely applied towards the selective transport, separation and characterization of biosystems. In particular, its application as electrode-less or insulator dielectrophoresis (iDEP), wherein the polarized particles are directed towards (by positive DEP or pDEP) or away (by negative DEP or nDEP) from spatially localized regions of high field caused by insulating constrictions in a microfluidic device, provides a variety of advantages for the sorting and analysis of biosystems.

In comparison to electrode-based methods, problems associated with field-induced adhesion and destruction are reduced since bio-particles are manipulated in an electrode-less or contact-less manner across a wide spatial extent spanning the entire device depth, thereby enhancing throughput.

In addition, the designs described herein provide for integration of DEP preconcentration of analytes with a variety of sensing paradigms since the polarized particles are not trapped at the vicinity of the electrodes driving the DEP. Rather, polarized particles are collected or trapped at (e.g., near, in the vicinity of, adjacent to, or proximal to) insulator constriction regions where, in certain embodiments, capture probes can be immobilized for enabling selectivity through bio-recognition strategies. Capture probes are not utilized in certain embodiments.

The electrodes driving the DEP field orthogonal to the fluid flow are often spaced a pre-determined distance from each other (~0.5-2 cm) to enhance a wide spatial extent for particle manipulation and to facilitate the absence of field distortion and bio-particle damage that can occur due to electrode edges within the channel. Due to the frequent electrode spacing preferences, higher voltages are often desired (typically 100-1000 $V_{RMS}$) than is typically required with electrode-based DEP (typically 20-40 $V_{RMS}$) to ensure the necessary field strength to provide for trapping particles having low or reduced polarizability. Higher field strengths are often provided, even in embodiments that include 3D constrictions (e.g., insulator constrictions) or nano-device designs that enhance localized field. This high voltage requirement can be problematic for conducting iDEP in the MHz frequency ranges, due to the performance degradation of commercial amplifiers. As a result, a majority of iDEP studies are restricted to DC fields, or low frequency AC fields (<500 kHz), where the discrimination is based only on cell membrane integrity, rather than on the electrophysiology of cellular cytoplasm (1-10 MHz) or nucleoplasm (>40 MHz), or the unique conformation of biomolecules (>1 MHz).

Design principles for constructing a wideband power amplifier for performing iDEP at MHz frequencies are provided herein. Based on counter-phase coupling of two operational amplifiers (Op-amps) by using a splitter to ensure 180° phase-shifted signals over a large bandwidth, in conjunction with an adjustable power supply and attenuator to arrest dissipation, the output power is maximized up to 15 MHz in one exemplary embodiment, while avoiding signal distortion. This is validated by demonstrating the absence of harmonic distortions and parasitic DC offset fields within the amplifier output at MHz frequencies, since these often adversely affect DEP trapping. The application of this wideband amplifier for enabling quantitative DEP analysis of 3 µm sized *Cryptosporidium parvum* (*C. parvum*) bio-particles is demonstrated by comparing its performance to state-of-the-art commercial amplifiers currently on the market. This instrumental innovation aids quantitative iDEP based separation of subpopulations of C. parvum oocysts based, for example, on sporozoite integrity in their cytoplasm (at 1-10 MHz) and towards coupling iDEP preconcentration to the detection of neuropeptide Y (at ~3 MHz) [18], prostate specific antigen (at ~5 MHz) and protein-DNA complexes (at 1 MHz). Distinctions based on electrophysiology of cell cytoplasm and nucleoplasm for separating stem cell subpopulations (among other cell populations, including mixed or heterogenous cell populations [19]) are also contemplated, using electrode-less and contact-less iDEP as described herein.

Methods: the Design Process

Figure 7:
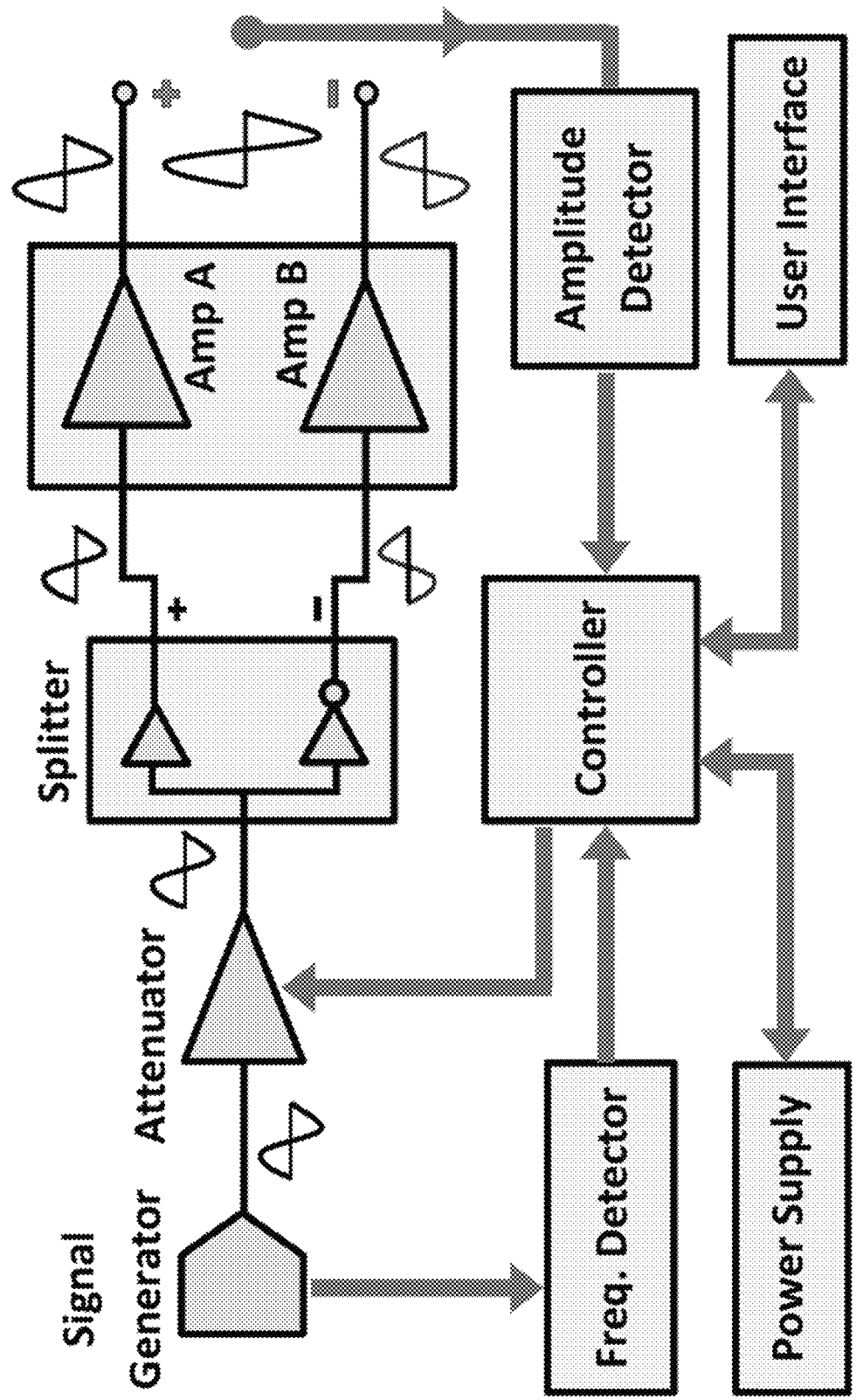
FIG. 7. Block diagram for the wideband amplifier circuit.

The literature on wideband power amplifiers is scarce. Prior work has focused on amplifying voltages (up to 1 kV) for operation at frequencies up to only a few hundred KHz, rather than at higher frequencies. State-of-the-art commercial power amplifiers (FLC Elec. A400DI, Trek Inc. 2100HF and Thorlab Inc. HVA200) are able to operate up at ~500 $V_{pp}$ until 500 kHz, after which they exhibit a steady drop in power. The design of the wideband amplifier circuit described herein is based, for example, on high speed power operational amplifiers (Op-amps) rather than on discrete transistors, since Op-amps are highly predictable ICs, in terms of gain and signal shape, with no need for particular biasing or stabilizing components. FIG. 7 depicts an exemplary circuit.

High Speed Dual-Amplifier and Splitter

The speed of power Op-amps under high voltage settings is limited by their slew rate. Slew rate is the maximum rate of change of output voltage per unit time (V/µs). Limitations in slew rate capability can give rise to distortions in signal shape of the amplifier output. For a sinusoidal signal, the slew rate (SR) capability at all points in an amplifier must satisfy:

$$\text{Slew rate (SR)} \geq \pi \times V_{pp} \times f \quad (1)$$

Here, f is the signal frequency and $V_{pp}$ is the peak-peak amplitude of the signal. Hence, to obtain a sinusoidal signal output at 5 MHz with amplitude of 250 $V_{pp}$ an Op-amp with a slew rate of: 4000 V/µs is called for. This is beyond the capability of ultrafast power Op-amps in the market. PA107DP from APEX Micro, for instance, is capable of slew rates only up to 2500 V/µs. To address this limitation, two identical PA107DP Op-amps were fed with counter-phase signals of the same amplitude. In this manner, whenever the output of one Op-amp is at its maximum, the output of the other Op-amp is at its minimum, thereby causing a voltage difference between the two outputs, which is twice that of each individual output. As a result, this counter-phase combination of the two Op-amps is equivalent to an Op-amp with a 5000 V/µs slew rate. However, the splitter unit that provides these counter-phase signals needs to be designed with super-fast low-power Op-amps (Texas Instruments LM7171) to obviate deviation from the 180° phase difference, for eliminating distortion and nonlinearity over a wide dynamic range of input signals and frequency bandwidth.

Self-Adjustable Power Supply

Power dissipation ($P_D$) inside the Op-amps can limit the maximum output power at high frequencies. If no load is connected or the output current is small ($P_{Load} \ll PD$), then for two symmetrical high-voltage supplies ($\pm V_S$) and supply current of $I_S$ drawn from the power supply, $P_D$ is given by:

$$P_D = (V_S^+ - V_S^-) \times I_S = 2 V_S I_S \quad (2)$$

With increasing frequency, the power dissipation first rises due to the higher supply current ($I_S$) from the lower internal impedances, while at even higher frequencies, the dissipation eventually falls due to diminishing output gain, thereby causing a peak in power dissipation at ~5 MHz. Hence, a self-adjustable Power Supply is often utilized for dynamic modulation of the supply voltages ($V_S$) at each working frequency, to ensure minimal dissipation in the 3-7 MHz range. In this manner, the drop in gain at higher frequencies is compensated by adjusting for the optimal input signal levels required to maximize output power, while avoiding over-heating and reducing signal distortion over a wide frequency range.

Attenuator and Controller Unit

The gain of the Op-amp drops steadily at certain frequencies, for example, above 1 MHz. Therefore, larger input signals at successively higher frequencies are often desired to maximize output amplitude. However, if this large input signal is maintained at lower frequencies then the output waveform will often be distorted from sinusoidal to that resembling a square wave, which increases power dissipation and total harmonic distortion (THD) due to operation in the saturation regime. Thus, an adjustable gain stage unit is often utilized to attenuate the input signal, so that the output amplitude is limited to a constant user-defined voltage level ($V_{max}$). The attenuator gain is adjusted, for example, by a controller based on the output amplitude and frequency.

Figures of Merit for Signal Characteristics

The performance of the wideband amplifier was compared to that of a so-called conventional amplifier (FLC A400DI), as this was one example of a product with an output of 300 $V_{pp}$ up to 1 MHz. The respective amplifiers were compared based on the frequency response of their output signal amplitude and distortion. Signal shapes (Tektronix TDS3012B-NV) were quantified by voltage at DC (parasitic DC) and amplitude at harmonic frequencies ($V_n$ for $n^{th}$ harmonic, with n=1 being the fundamental) for computing Total Harmonic Distortion (THD):

$$THD = \frac{\sqrt{v_2^2 + v_3^2 + \ldots + v_n^2}}{v_1} \quad (3)$$

DEP Force Quantification

Comparison of the levels of positive DEP on *Cryptasporidium parvum* in the MHz range was performed by using the respective amplifiers within an electrode-less iDEP device. The DEP force values were calculated using frame-by-frame tracking of the trapped particles to extract their displacement vectors (x and y) over time (t) to compute $F_{DEP}$ using:

$$F_{DEP} = m \frac{d^2 x}{dt^2} - 6\pi\eta a \frac{dx}{dt} \quad (4)$$

Here, m and a are the mass and radius of the particles and η is the viscosity of the fluid.

Figure 8:
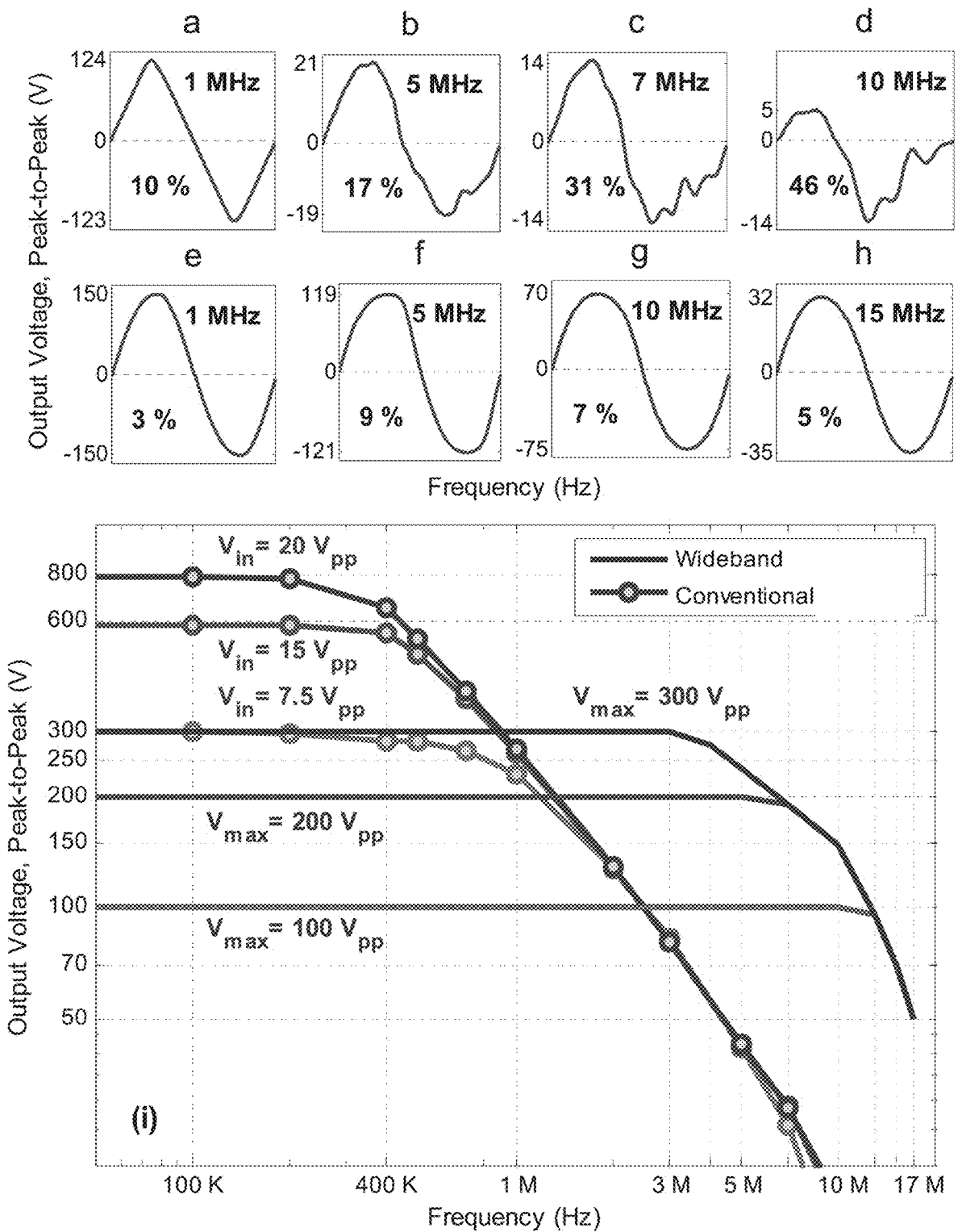
FIG. 8. Output waveform of conventional amplifier (FLC A400DI) for $V_{in}=15V_{pp}$ (a-d) vs. wideband amplifier (e-h) in the 1-15 MHz range (THD in %). (i) Frequency responses of wideband amplifier (square inicators) at the indicated $V_{max}$ levels vs. the conventional amplifier (circle indicators) at the indicated $V_{in}$ levels. Normalized amplitudes ($V_2/V_1$) and ($V_3/V_1$) at 1-10 MHz for: (j) conventional amplifier and (k) the wideband amplifier.
Figure 8:
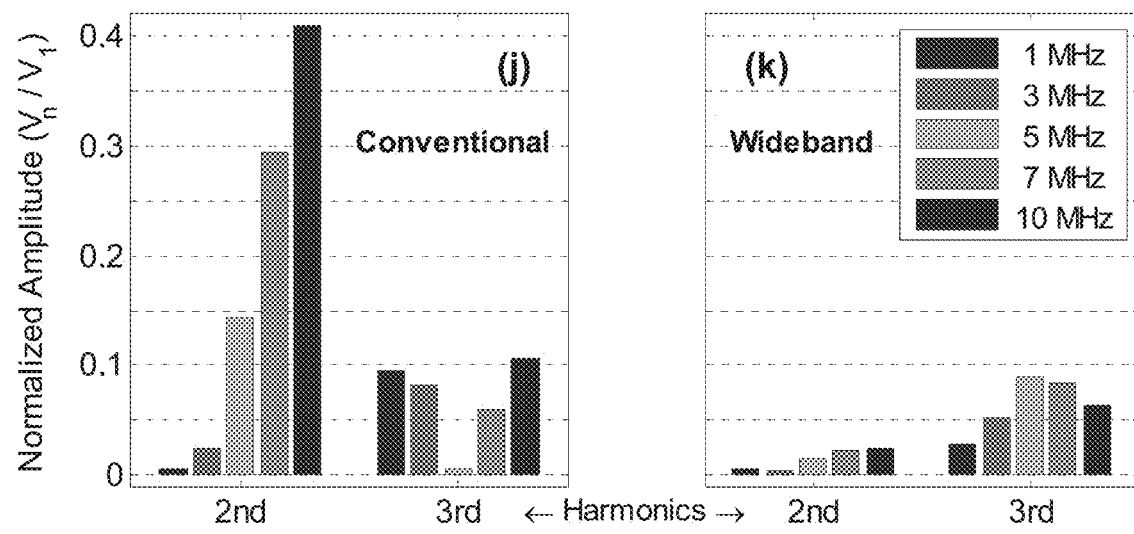

The frequency responses of the output amplitude and signal distortion from the wideband amplifier are compared to those from the FLC A400DI amplifier in FIG. 8. It is apparent that while the conventional amplifier offers greater voltage in the low frequency range (<800 kHz), the output from the wideband amplifier is far higher, around and above 1 MHz. Furthermore, the conventional amplifier shows a highly distorted signal shape at successively higher frequencies in the MHz range (see, e.g., FIGS. 8a-d), whereas the sinusoidal wave-shapes are preserved in the MHz range for the wideband amplifier (FIG. 8e-h). This signal distortion is quantified, for example, in FIG. 8j-k and Table 1 in terms of the parasitic DC and THD levels. There it can be seen that parasitic DC levels from the conventional amplifier exhibit a steady rise with increasing frequency due to, for example, the increasing difference in DC levels at the two channels of the amplifier. While the absolute parasitic DC levels are small, they become a greater fraction of the output at higher frequencies, since slew rate limitations cause a steep decline in $V_{RMS}$ output at the fundamental frequency. For instance, while the VRms to parasitic DC ratio is 250 at 1 MHz, it drops steeply to just 28 at 5 MHz, and 8 at 10 MHz.

TABLE 1

Comparison of output voltage (RMS and DC offset) and % THD of conventional amplifier vs. the wideband amplifier.

| | | Frequency | | | | | | |
|---|---|---|---|---|---|---|---|---|
| | | 1 | 3 | 5 | 7 | 10 | 13 | 15 |
| Conventional Amplifier | $V_{RMS}$ (V) | 77 | 25 | 14 | 10 | 6 | — | — |
| | DC (V) | 0.3 | 0.3 | 0.5 | 0.9 | 0.7 | — | — |
| | THD (%) | 10 | 11 | 17 | 31 | 46 | — | — |
| Wideband Amplifier | $V_{RMS}$ (V) | 107 | 107 | 91 | 74 | 54 | 34 | 25 |
| | DC (V) | 0 | 0 | 0 | 0 | 0 | 0 | 0 |
| | THD (%) | 3 | 6 | 9 | 9 | 7 | 6 | 5 |

Figure 9:
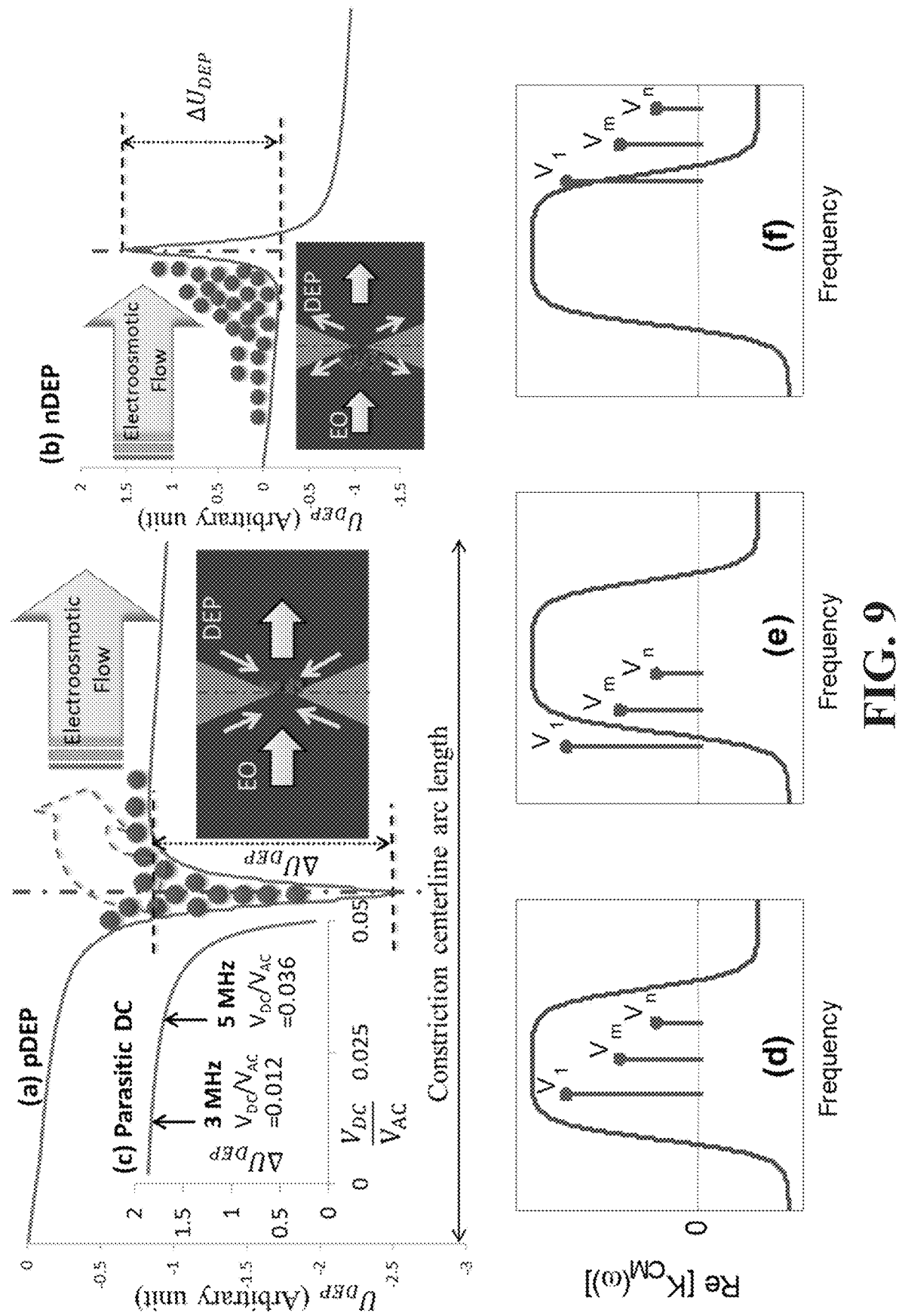
FIG. 9. Influence of DC offset on AC field driven pDEP (a) and nDEP (b), as quantified in (c). (d-g) Influence of harmonic distortion ($V_m$, $V_n$) of the fundamental AC signal ($V_1$) at different regions of the polarizability dispersion.
Figure 9:
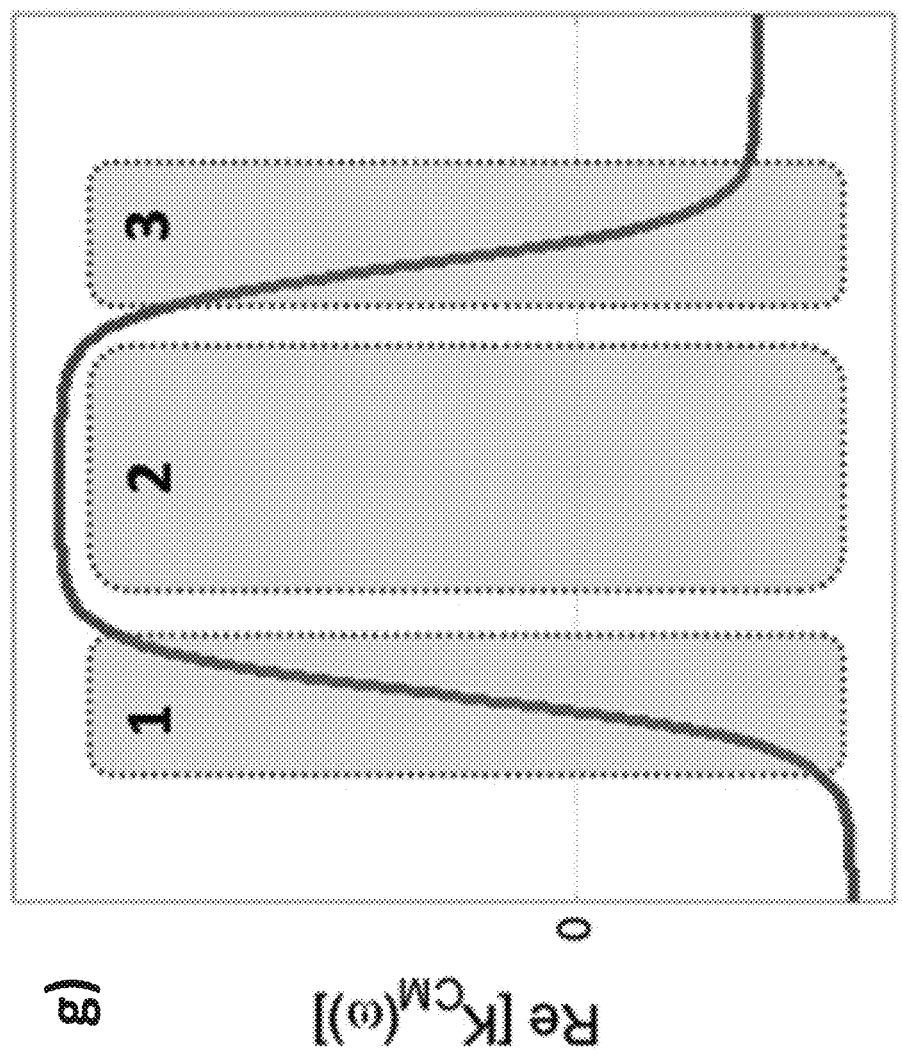
Figure 10:
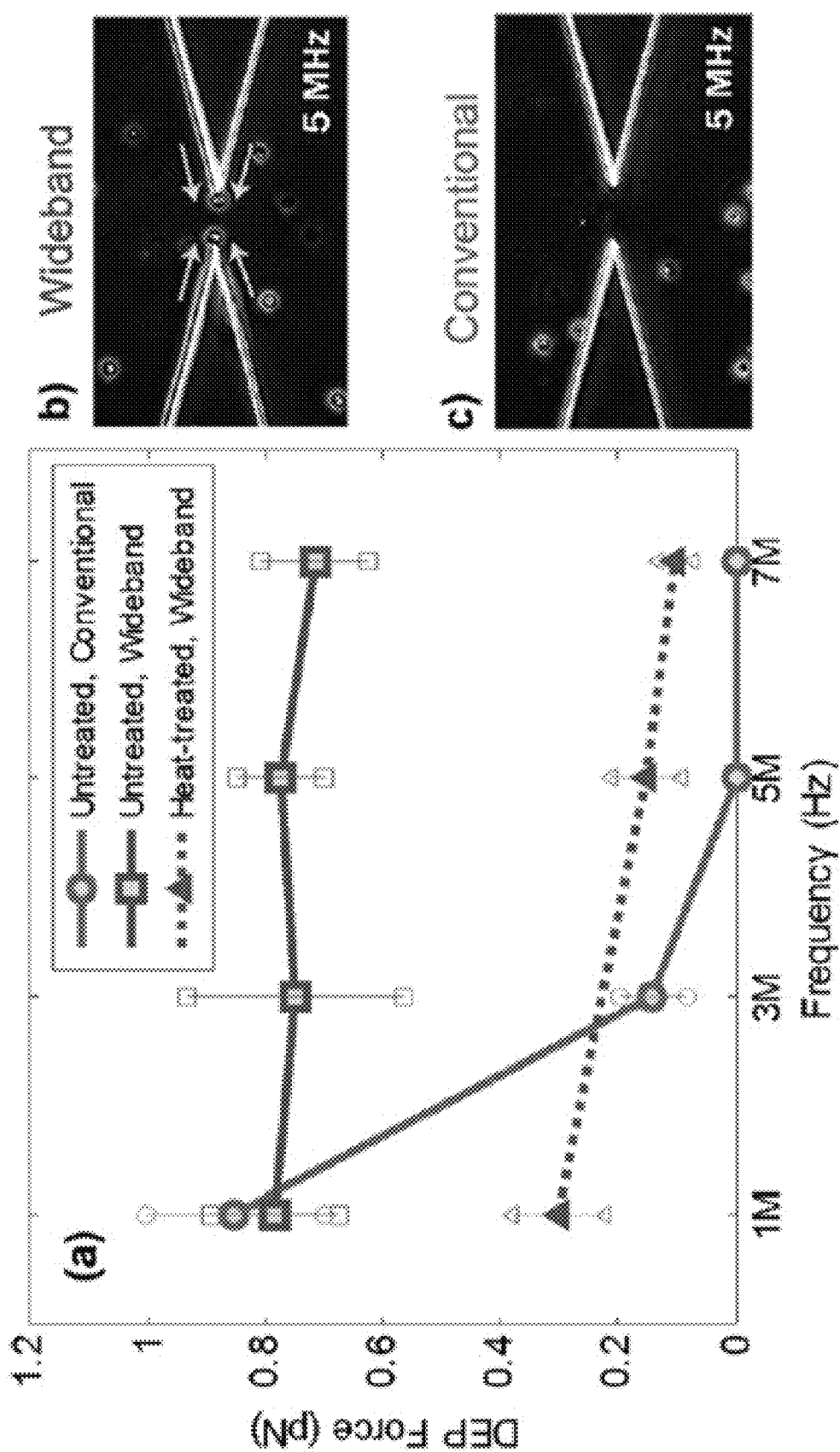
FIG. 10. Measured DEP force dispersion of C. parvum in the 1-7 MHz region using the conventional vs. wideband amplifier.
Figure 11:
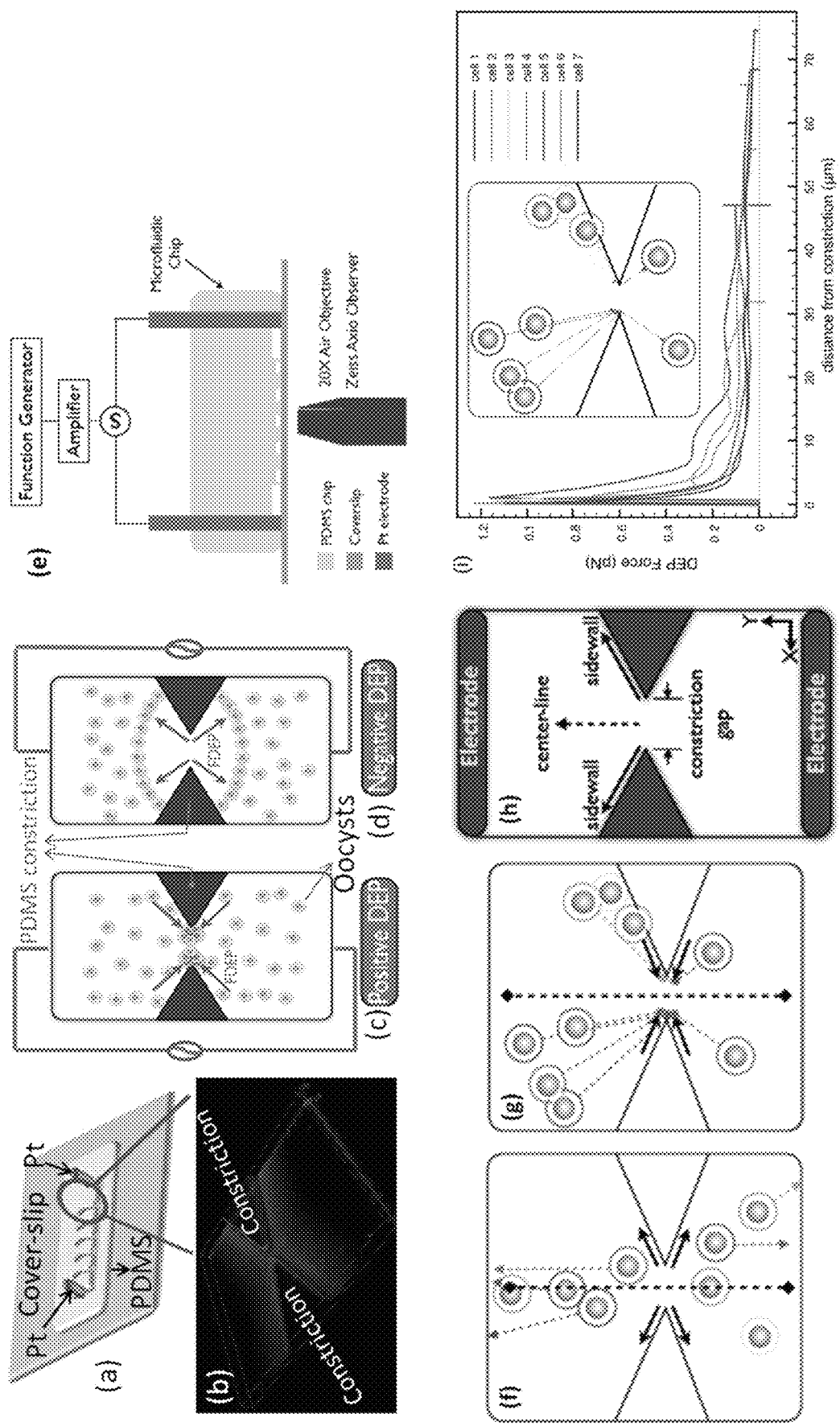
FIG. 11:(a) Schematic device; (b) confocal image of constriction chip; and force directions under: (c) positive DEP (PDEP), and: (d) negative DEP (NDEP). (e) Set-up for observing DEP behavior of oocysts. Translation vectors for oocysts under: (f) NDEP; and (g) PDEP. (h) Center-line and sidewall vectors for the constriction device. (i) Typical force profiles in pN versus distance from constriction tip for untreated oocysts. There are ~25-30 data points over the constriction region and force profiles peak at 2-4 μm from constriction tip.

This steady rise of parasitic DC in proportion to the AC field causes electrophoretic ($F_{EP}$) and electroosmotic ($F_{EO}$) forces to influence the net force balance. As is apparent from FIG. 9a-b, while these DC-driven electrokinetic forces tilt the potential profile to enhance trapping under nDEP, they also cause the leakage of particles under pDEP trapping, thereby altering the quantitative DEP force dispersion by reducing effective pDEP trapping in the MHz range. As indicated in FIG. 9c, for example, beyond a critical level DC fields can cause a reduction in the DEP trapping potential. On the other hand, parasitic DC levels are negligible for the wideband amplifier, thereby offering highly quantitative DEP force dispersions. An alternate problem with conventional power amplifiers is the emerging harmonic distortion at MHz frequencies. Herein, the amplitude levels of the higher order harmonics are large enough to cause a deviation of the sinusoidal wave shape, from a single frequency signal to one that includes signals at several harmonic frequencies, thereby influencing the polarizability dispersion (FIG. 9d-g). This waveform distortion arises due to phase shift deviations at high frequency from the required counter phase signal input to the Op-amps or due to the operation of Op-amps at their saturation level at low frequencies.

As per the normalized amplitude at each harmonic with respect to the fundamental frequency ($V_n/V_1$) in FIG. 8j-k and % THD in Table 1, significant distortions are apparent with the conventional amplifier beyond 5 MHz, especially at the second harmonic, whereas the distortions, if present, are much weaker with the wideband amplifier. A sine wave, which exhibits only one harmonic, has a THD of zero, whereas triangular and symmetrical square waves exhibit THDs of 0.12 and 0.48, respectively. At least one important implication of this harmonic distortion is an alteration in the DEP force magnitude, and in some scenarios the force direction too. For instance, FIG. 9d (see also FIG. 9g-region 2), presents the scenario when the fundamental frequency, as well as the harmonics cause pDEP, with relatively constant polarizability dispersion (real-part of the Clausius-Mossotti ($K_{cm}$)). We can then calculate an altered DEP force ($F_{DEP}$) due to the distorted signal (THD) with peak-peak amplitude of $V_1$ (fundamental), as a function of the ideal sinusoidal signal of peak-peak amplitude $V_{pp}$ that causes $F_{ideal}$ (further details provided below):

$$F_{DEP} = (1 + THD^2)\left(\frac{V_1}{V_{pp}}\right)^2 F_{Ideal} \tag{5}$$

Here, the frequency dependent term: $(1+THD^2)$ influences the force dispersion, due to contributions of the higher order harmonics, whereas the term: $(V_1/V_{pp})^2$, reflects an alteration in maximum amplitude of the output signal due to deviation from the ideal sinusoidal wave shape. Hence, while the distorted quasi-triangular wave shape of the conventional amplifier causes a reduction in DEP force by just 20% at 1 MHz (due to 10% THD and $V_1/V_{pp}$=0.9), the respective force reductions are larger at 5, 7 and 10 MHz. On the other hand, since the THD of the wideband amplifier is less than 10% (Table 1) and $V_1/V_{pp}$ remains close to unity, the DEP force alteration is less than 5% over the MHz range. Next, considering the scenario where the fundamental frequency is in the nDEP region, whereas the harmonics lie in the pDEP frequency region (FIG. 9g-region 1), then the force would be further distorted, since the Re($K_{CM}$) is no longer constant but rather varies with each harmonic signal. For instance, if $K_{CM}$ at the fundamental frequency is $K_{CM}(\omega_1)$ and that for the next significant higher order harmonic is $K_{CM}(\omega_m)$, then Eq. (5) can be modified (ESI):

$$F_{DEP} = (1 + \alpha THD^2)\left(\frac{V_1}{V_{pp}}\right)^2 F_{Ideal}; \alpha = \frac{\text{Re}[K_{CM}(\omega_m)]}{\text{Re}[K_{CM}(\omega_1)]} \tag{6}$$

In the scenario wherein the fundamental frequency ($\omega_1$) is in the nDEP region close to crossover towards pDEP, whereas the next significant harmonic ($\omega_m$) is in the pDEP region, as in FIG. 9e (see also FIG. 9g-region 1), then: a « -1, since $K_{CM}$ under nDEP ($\omega_1$) is usually less than that under pDEP ($\omega_m$). This causes greater DEP force distortions from $F_{ideal}$ than the scenario in FIG. 9d (see also FIG. 9g-region 2). Moreover, at high enough THD values, the direction of the DEP force could also be altered. A similar scenario can occur at ultra-high frequencies near the second DEP crossover region (FIG. 9f; FIG. 9g-region 3).

Comparison of Amplifiers for iDEP Dispersion in MHz Range

Finally, a comparison of the DEP force dispersion in the MHz range on the iDEP device using the conventional amplifier versus the wideband amplifier is provided, with oocysts of C. parvum as an exemplary model bio-particle. The exemplary iDEP device is composed of PDMS microchannels with sharp symmetric constrictions (1000 to 15 μm) to enhance the localized field. We focus on the DEP force dispersion in the 1-7 MHz range, where the polarized oocysts exhibit positive DEP due to the dominance of cytoplasm conductivity, thereby causing trapping at the constriction tip. It is apparent from the measured DEP force data in FIG. 4 (videos in ESI) that while the trapping under pDEP using the conventional amplifier is clear at 1 MHz, it is less clear at 3 MHz and absent at 5 MHz. On the other hand, with the wide bandwidth amplifier, the trapping continues to be significant and at a constant level in the 1-7 MHz range.

To provide electrode-less or contact-less manipulation of biosystems in the MHz frequency range, we present herein certain design principles for a wideband power amplifier to address the steep drop in amplitude and the rise of signal distortion that occurs within conventional amplifiers. Issues related to the present innovations in this area are described conceptually herein and though specific exemplary equipment an implementations are described, the present disclosure is not intended to be limited as such. Through counter-phase coupling of two operational amplifiers by using a wideband splitter circuit, in conjunction with a self-adjustable power supply and an attenuator to deliver a constant power output for avoiding over-heating and signal distortion due to saturation, power up to 15 MHz was achieved. This is validated by demonstrating the reduction of harmonic distortions and parasitic DC effects within the amplifier output, as well as by demonstrating a constant level of pDEP force on oocysts of *C. parvum* in the 1-7 MHz range, due to dominance of cytoplasmic conductivity.

Electronic Supplementary Information (ESI): Quantifying DEP Force on the Oocysts from Velocity Tracking Measurements:

For a particle accelerated under a dielectrophoretic force ($F_{DEP}$), based on Netwon's second law, the net force on the particle of radius: a, within a medium of viscosity: scan be determined by tracking displacement (x) as a function of time (t)

$$F_{DEP} - 6\pi\eta\alpha\frac{dx}{dt} = m\frac{d^2x}{dt^2} \quad \text{Eq. (S1-1)}$$

Tracking dielectrophoretic particle displacement versus time: The set-up for imaging the dielectrophoretic translation of oocysts is shown in FIGS. 11*a* and 11*e*. Based on data from high frame per second (~30 fps) movies of oocyst translation under FDEp, the displacement (x & y) are tracked as a function of time (t) for particles translated away from the constriction tip under negative DEP (NDEP) and towards the constriction tip under positive DEP (PDEP). For NDEP, the translation of oocysts that were originally at rest at the constriction tip prior to application of AC field at the particular frequency of interest is recorded as displacement versus time of field, onwards from the constriction tip along a particular displacement vector (FIG. 11*f*). For PDEP, the translation of oocysts that were originally at rest in the region immediately outside of the constriction gradient prior to application of AC field at the particular frequency of interest is recorded as displacement versus time of the field, towards the constriction tip along a particular displacement vector (FIG. 11*g*). Since the motion of particles take place in two-dimensional space, trajectories of particles encompass both X and Y coordinates, leading us to do all computation for both directions individually.

In this manner, the experimental raw data acquired in the form of video, is processed to yield a table of position versus time; i.e. (x, y,t) coordinates for the analyzed cocysts. The displacement data (x and y vectors) as a function of time is algorithmically smoothed by using a high-order polynomial fit, since the faster displacements under higher FDEP require higher frame rates for accurately tracking displacement over time, versus the slower displacements. To ensure an effective smoothing, the lack of jagged features on the derivatives of Eq. (S1) was evaluated. As a result the equation $v_x=dx/dt$, $v_y=dy/dt$, $a_x=d^2x/dt^2$ and $a_y=d^2y/dt^2$ is obtained for the oocysts at a particular applied field and frequency, after each of the disinfection treatments, which can be used to compute the X and Y components of $F_{DEP}$ frequency response in the direction of the particle trajectory ("track" direction). At each point of the trajectory, the distance from the constriction (r) can be determined based on x and y coordinates: $r=\sqrt{x^2+y^2}$ and the total DEP force based on the value of $F_x$ and $F_y$ at that point: $F_r=\sqrt{F_x^2+F_y^2}$. Therefore, the Force vs. distance (F (r)) is computed.

Normalizing for field non-uniformities: Within the constriction device, the profile of the electric field and hence, $F_{DEP}$, varies depending on the displacement vector of the oocysts. This can create a variation in $F_{DEP}$ of up to an order of magnitude, depending on displacement direction and distance of the oocysts in relationship to the constriction tip of a given device. Hence, all the data for field differences was normalized from the velocity tracked direction (track) to that along the centerline direction (CL), by accounting for the field differences ($\nabla E^2$) between the "track" and "centerline" directions through a normalization factor:

$$K = \frac{\nabla E_{track}^2}{\nabla E_{CL}^2};\ F_{DEP}^{CL} = \frac{F_{DEP}^{track}}{K}$$

The $\nabla E^2$ in the "track" direction is calculated by translating the measured trajectory of the oocyst to a simulation of the device in order to read the magnitude and gradient of the electric field along this vector direction. The magnitude and gradient of the electric field along the centerline direction is also available from this simulation. In this manner, by dividing the computed DEP force along the "track" direction by the field enhancement ratio K, all the variations in DEP force can be attributed to variations in particle polarizability, rather than field non-uniformities due to the device geometry. An exemplary set of force profile data for untreated oocysts is shown in FIG. 11(*i*).

Influence of Harmonic Distortion on Dielectrophoretic Force and its Frequency Dispersion The Clausius-Massotti relation describes the DEP force ($F_{DEP}$) on a spherical particle of radius: a, in a medium of permittivity: $E_m$, under an RMS field: $E_{rms}$ $$F_{DEP}=2\pi\epsilon_m a^3 Re[K_{CM}(\omega)]\nabla_{rms}^2 \quad \text{(S2-1)}$$

Here, $K_{CM}$ is the Classius-Mossoti factor, which represents the frequency-dependent complex dielectric contrast of the particle versus the medium:

$$K_{CM}(\omega) = \frac{\epsilon_p^* - \epsilon_m^*}{\epsilon_p^* - 2\epsilon_m^*} \quad \text{(S2-2)}$$

Here, $\epsilon^*$ denotes the frequency-dependent complex permittivity which includes both permittivity ($\epsilon$) and conductivity ($\sigma$) as $\epsilon^*=\epsilon+(\sigma/j\omega)$. Subscripts p and m denote the respective property of particle and medium, respectively.

If the Electric field E(t) has a pure sinusoidal waveform with the frequency of $\omega_1$:

$$E_{rms}^2 = \frac{1}{8}E_{pp}^2 \quad \text{(S2-3)}$$

Then equation (1) can be rewritten as $$F_{DEP} = \frac{1}{8} \cdot 2\pi\epsilon_m a^3 \text{Re}[K_{CM}(\omega_1)]\nabla E_{pp}^2 \qquad (S2\text{-}4)$$

In case the applied field is not purely sinusoidal, then it comprises of higher order harmonics where their corresponding frequencies ($\omega_n$) are integer multiples of the fundamental frequency ($\omega_1$). Using Parseval's theorem, $E_{rms}$ can be expanded based on its orthogonal harmonics:

$$E_{rms}^2 = \frac{1}{8}(E_1^2 + E_2^2 + E_3^2 + \ldots) \qquad (S2\text{-}5)$$

Here, $E_1 \ldots E_n$ are the peak-peak intensities of each harmonic of the electric field. However, $K_{CM}$ may take different value at each frequency, as follows:

$$F_{DEP} = \frac{1}{8} \cdot 2\pi\epsilon_m a^3 \nabla (\text{Re}[K_{CM}(\omega_1)]E_1^2 + \qquad (S2\text{-}6)$$
$$\text{Re}[K_{CM}(\omega_2)]E_2^2 + \text{Re}[K_{CM}(\omega_3)]E_3^2 + \ldots)$$

If the most significant differences occurring between the first two harmonics is assumed, with all other harmonics at higher frequencies exhibiting minor differences in $K_{CM}$ value equal to $K_{CM}(\omega_2)$ denoted as $K_{CM}(\omega_m)$, then (S2-6) can be shortened as:

$$F_{DEP} = \qquad (S2\text{-}7)$$
$$\frac{1}{8} \cdot 2\pi\epsilon_m a^3 \nabla \left(\text{Re}[K_{CM}(\omega_1)]E_1^2 + \text{Re}[K_{CM}(\omega_m)]\frac{(E_2^2 + E_3^2 + \ldots)}{E_1^2 \cdot THD^2}\right)$$

$$F_{DEP} = \frac{1}{8} \cdot 2\pi\epsilon_m a^3 \text{Re}[K_{CM}(\omega_1)]\nabla E_1^2 \cdot (1 + \alpha THD^2) \qquad (S2\text{-}8)$$

Here a is the ration of $\text{Re}[K_{CM}]$ at the frequencies of higher order harmonics versus fundamental harmonic $$\left(\alpha = \frac{\text{Re}[K_{CM}(\omega_m)]}{\text{Re}[K_{CM}(\omega_1)]}\right)$$

The Peak-to-Peak amplitude of fundamental harmonic is not generally equal to the Peak-to-Peak amplitude of a signal. To better understand the effect of distortion on DEP force, the DEP force can be compared with the so-called Ideal DEP force (Fideca) from a sinusoidal field with the same Peak-to-Peak amplitude to the original signal:

$$F_{Ideal} = \frac{1}{8} \cdot 2\pi\epsilon_m a^3 \text{Re}[K_{CM}(\omega_1)]\nabla E_{pp}^2 \qquad (S2\text{-}9)$$

The DEP force ($F_{DEP}$) and the Ideal DEP Force ($F_{ideal}$) can be related together by comparing equation (S2-8) and (S2-9):

$$F_{DEP} = (1 + \alpha THD^2)\frac{[\nabla E_1^2]}{[\nabla E_{pp}^2]}F_{Ideal} \qquad (S2\text{-}10)$$

The gradient terms ($\nabla E_{pp}^2$, and $\nabla E_1^2$) in (S2-9) depend on the position of particle, device geometry and field intensities. Hence, their ratio can be substituted based on their corresponding intensities and applied electric potentials:

$$\frac{[\nabla E_1^2]}{[\nabla E_{pp}^2]} = \frac{E_1 \cdot \nabla E_1}{E_{pp} \nabla E_{pp}} = \frac{E_1^2}{E_{pp}^2} = \left(\frac{V_1}{V_{pp}}\right)^2 \qquad (S2\text{-}11)$$

Here, $V_{pp}$ and $V_1$ are the Peak-to-Peak amplitudes of the applied electric potential and its fundamental harmonic, respectively.

Finally, by substituting (S2-11) into (S2-10) can be obtained:

$$F_{DEP} = (1 + \alpha THD^2)\left(\frac{V_1}{V_{pp}}\right)^2 F_{Ideal} \ldots \qquad (S2\text{-}12)$$

In special case where all harmonics, including the fundamental harmonic, lie in the pDEP region and have the same $K_{CM}$, (a=1) and (S2-12) can be simplified to:

$$F_{DEP} = (1 + \alpha THD^2)\left(\frac{V_1}{V_{pp}}\right)^2 F_{Ideal} \ldots \qquad (S2\text{-}13)$$

See related articles (each of which is incorporated herein by reference):
1. H. A. Pohl, J. Appl. Phys., 1951, 22, 869.
2. T. B. Jones, Electromechanics of particles (Cambridge Univ. Press, 1995).
3. R. Pethig, Biomicrofluidics, 2010, 4.
4. C. F. Chou et al., Biophys J, 2002, 83, 2170-2179.
5. J. Regtmeier et al., Electrophoresis, 2011, 32, 2253-2273.
6. E. B. Cummings and A. K. Singh, Anal. Chem., 2003, 75, 4724-4731.
7. S. K. Srivastava et al., Anal. and Bioanal. Chem., 2011, 399, 301-321.
8. C. F. Chou and F. Zenhausern, IEEE, 2003, 22, 62-67.
9. A. Salmanzadeh et al., Lab on a chip, 2012, 12, 182-189.
10. N. Swami et al., Lab on a chip, 2009, 9, 3212-3220.
11. W. A. Braff et al., Lab on a chip, 2012, 12, 1327-1331.
12. V. Chaurey et al., Electrophoresis, 2013, 34, 1097-1104.
13. K. T. Liao et al., Electrophoresis, 2012, 33, 1958-1966.
14. B. H. Lapizco-Encinas et al., J Microbiol Meth, 2005, 62, 317-326.
15. B. G. Hawkins et al., Anal. chemistry, 2007, 79, 7291-7300.
16. A. Rohani et al., Electrophoresis, 2014.
17. Y. H. Su et al., Analyst, 2014, 139, 66-73.
18. B. J. Sanghavi et al., Analytical chemistry, 2014, 86, 4120-4125.
19. R. Pethig et al., J Biomed Biotechnol, 2010.

20. J. W. Ting et al., Nuc. Sci. Symp. Conf. Record, 2003 IEEE, 2, 1247-1249.

Dielectrophoretic Monitoring and Separation of *C. difficile*

S-layers glyco-proteins are part of the cell wall envelope in gram positive and gram negative bacteria. They are integral towards surface recognition, colonization, host-pathogen adhesion and virulence. A number of studies have shown that the antigenic variations of S-layers between *C. difficile* strains can serve as a potential alternative to sero-typing by PCR-restriction fragment length polymorphism analysis and nucleotide sequencing, but these methods have not been applied towards the recovery of intact microbials of each strain. S-layer deficient mutant strains can exhibit morphological differences, such as lower surface roughness versus the wild type strain, within various microbial samples. Hence, the correlation of S-layer induced morphological or functional variations to the cell electrophysiology can enable inter-strain distinctions for the separation of intact *C. difficile*, as well as other gram positive and gram negative microbials that exhibit inter-strain S-layer variations. For instance *Campylobacter fetus*, exhibits antigenically distinct S-layers due to DNA inversion and recombination of surface array A gene (sapA), while *Geobacillus stearotherrnophilus* has various S-layer gene expressions depending on different oxygen level, and strains of *C. fetus* and *Lactobacillus helveticus* can be identified based on the S-layer gene after PCR amplification.

Dielectrophoresis (DEP) causes the frequency-selective translation of polarized bio-particles in a spatially non-uniform electric field, either towards (by positive DEP or pDEP) or away (by negative DEP or nDEP) from the high field regions of a microfluidic device, depending on the polarizability of the bin-particle versus that of the medium. Hence, in spite of the heterogeneous nature of microbial samples, the frequency response of the DEP velocity of individual cells towards or away from localized regions of a microfluidic device can be used to quantify the alterations in electrophysiology of each cell type, while the frequency-selective DEP collection rate at these localized regions can be used to quantify the relative levels of each cell type. While prior work has focused on applying DEP towards the separation and discrimination of live versus dead gram positive or gram negative bacteria and sorting of fluorescently labeled *E. coli*; more recent work has demonstrated its ability to distinguish serotypes of *E. coli*, discriminate wild type versus surface protein isogenic mutant bacteria strains, characterize subtle modifications in capacitance of microbial cell wall and discern persistent versus susceptible subpopulations of *Cryptos-poridirim parvirm* through sensitive and label-free measurement of the DEP trapping force on single microbial cells. In the present description, differences in cell wall morphology, presumably attributed to the constituting S-layer within each *C. difficile* strain, are demonstrated as providing for their independent distinction; thereby permitting the label-free separation of intact microbial subpopulations of each strain type using the disclosed methods, systems, and devices, for example before and after antibiotic treatment. The morphological differences in the cell wall region of *C. difficile* strains cause systematic differences in their dielectrophoretic (DEP) frequency spectra due to alterations in the net capacitance of their cell wall. The sensitivity of the DEP method for monitoring alterations to each *C. difficile* strain after vancomycin treatment is benchmarked against the toxin production and growth rate methods. Based on this, we provide the application of DEP techniques towards the independent monitoring and separation of each *C. difficile* strain from mixed samples, in a non-destructive and label-free manner.

Experimental Methods

Bacteria strains preparation. II three *C. difficile* strains were purchased from ATCC. The bacteria were cultured in brain heart infusion (BHI) broth (BD BBL Brain Heart Infusion) at 37° C. overnight under anaerobic condition before further antibiotic treatment or dielectrophoretic experiments. 250 μL of the overnight cultured bacteria suspension and 750 μL of the BHI with vancomycin (Novaplus) or without vancomycin for the control groups were mixed in Eppendorf tubes and incubated at 37° C. for 4 hours or 24 hours. The vancomycin concentration for VPI10463 (high-toxigenic, HTCD) was 2 mg/mL and 1 mg/mL for ATCC630 (low-toxigenic, LTCD) and VPI11186 (non-toxigenic, NTCD). Prior to the dielectrophoresis experiments, the BHI broth was replaced with 8.8% sucrose water and re-adjusted with BHI broth to optimize the medium conductivity 105±5% mS/m for enabling DEP-based distinction of *C. difficile* strains from mixed samples. All three strains were confirmed to be viable within this altered BHI media over the timeframe of the DEP experiments, as per the colony forming unit (CFU) assay.

Growth measurement. 250 μL of the overnight cultured bacteria suspension and 750 μL of the BHI broth, with or without vancomycin were mixed in Eppendorf tubes. The optical density at a wavelength of 600 nm (OD600) of the mixed bacteria suspensions, measured by Spectrophotometry (Eppendorf Biophotometer) before incubation, was indexed as the "0 hour" time point. The OD600 number at later time points (4 and 24 hours) for respective strain at each condition was normalized to its 0 hour point.

Toxicity enzyme-linked immunosorbent assay. Total toxin (A/B) production was measured using the *C. difficile* TOX A/B II kit (Tech-Lab) according to the manufacturer's instructions. Culture supernatants were collected at 0, 4 and 24 hours by centrifugation at 3500 rcf for 5 min and stored at −20° C. The supernatants of the VPI110463 strain were diluted 1 to 20, while the supernatants of the VPI11186 strain were undiluted. Each specimen was run in duplicate. Total toxin levels were determined by measuring A450 under a 96 well plate spectrophotometry. The A450 number at each time point (4 hours and 24 hours) of each strain at each condition was normalized to its 0 hour time point.

Sample preparation for transmission electron microscope imaging. 1 mL of the overnight cultured bacteria samples were pelleted and fixed in 2% glutaraldehyde and 2% paraformaldehyde in PBS for 4 hours at room temperature. The samples were pelleted and washed 3 times in DI water before re-suspension in 2% osmium tetroxide. After 30 minutes, the samples were pelleted and washed 2 times in DI water before dehydration process. The samples were dehydrated through a serial gradient ethanol solution (50%, 70% 95% and 100%), for a 10 minute for each sample. The samples then re-suspended in 1:1 EtOH/EPON (epoxy resin) overnight, followed by 1:2 EtOH/EPON for 2 hours and 1:4 EtOH/EPON for 4 hours and 100% EPON for overnight. After embedding the samples in fresh 100% EPON, the samples were baked in a 65° C. oven. The EPON hardened samples were sectioned to 75 nm, mounted onto 200 mesh copper grids and contrast stained with 0.25% lead citrate and 2% uranyl acetate for TEM imaging (JEOL 1230) at 80 kV (SIA digital camera).

Dielectrophoretic characterization of *C. difficile*. The experimental setup has been described in our prior work. Briefly, Standard PDMS (Poly-di-methyl-siloxane) micro-molding methods were used to micro-fabricate channels with sharp lateral constrictions (1000 μm to 15 μm). This "constriction chip" (i.e., an exemplary device; also referred to herein as a device having an "insulator constriction" or "insulating constrictions") was bonded using oxygen plasma treatment to a standard coverslip for easy microscopic viewing of DEP behavior. Using Pt electrodes at the inlet and outlet, AC fields were applied over a wide-frequency range (10 kHz-15 MHz) by utilizing a power amplifier for particle trapping towards or away from high field points at the constriction tips. The trajectory of the unlabeled *C. difficile* of each strain type was observed under this field, as high frame per second movies to quantify the DEP velocity. For experiments within mixed *C. difficile* samples, the trapped microbials were released and analyzed with the immunoassay to confirm toxigenicity. A full description of the simultaneous and automated dielectrophoretic tracking of single bio-particles can be found in our previous work.

Morphological Differences Between *C. difficile* Strains.

Figure 12:
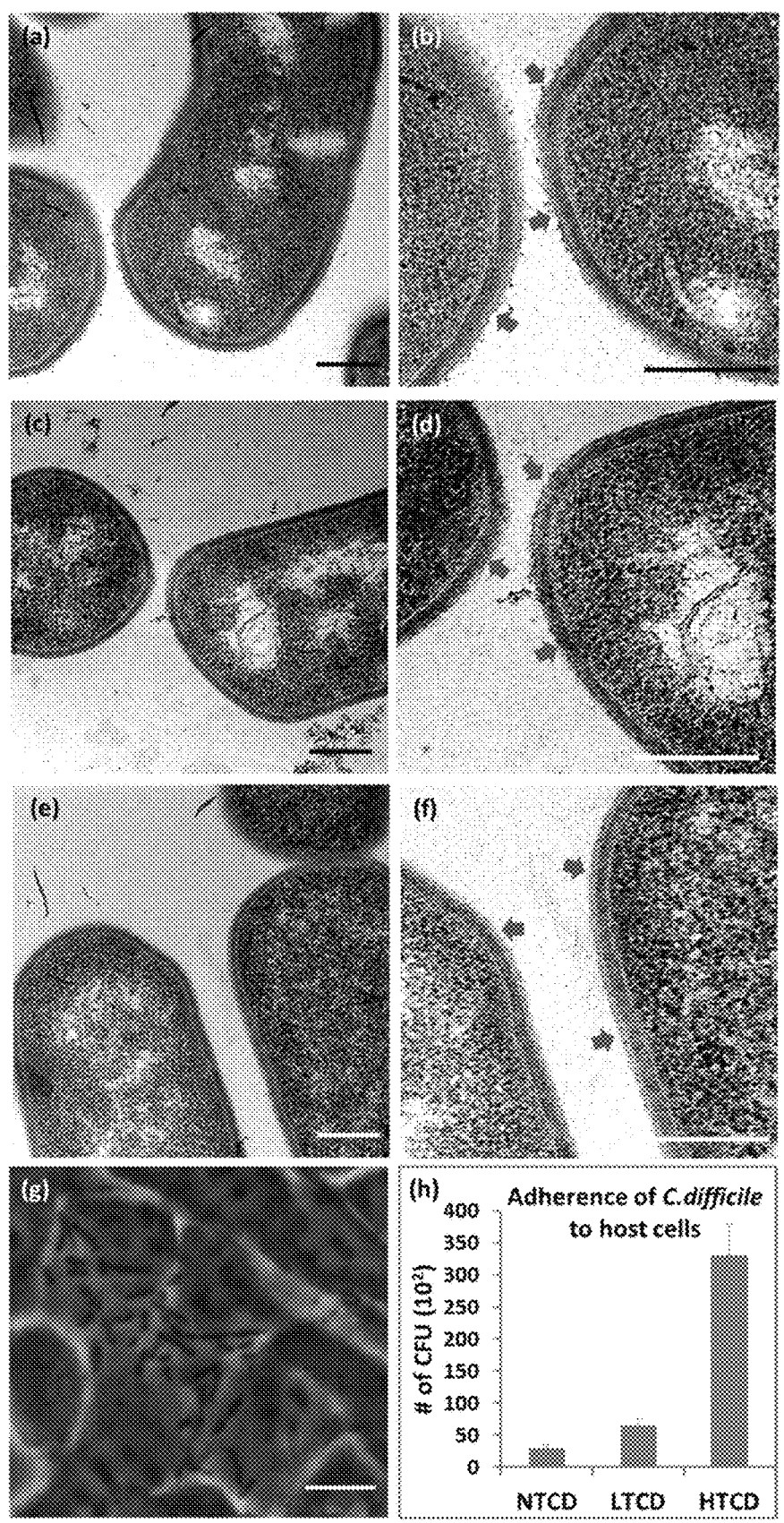
FIG. 12: Transmission electron microscope images of the C. difficile strains at 50 k magnification (a-c) and 100 k magnification (d-e). (a & d): HTCD (High-toxigenic Cdacile, VPI1.0463); (b & e): LTCD (Low-toxigenic C. difficile, ATCC630) and (c & f): NTCD (non-toxigenic C. difficile, VPI11186) strains. Scale bar: 0.2 μm. (g): A representative phase contrast image showing HTCD adherence to the human colon epithelial host cells. Scale bar: 5 μm. (h) Variations in adherence of each C. difficile strain to human colon epithelial cells by enumerating colony-forming units (CFU).

The morphological differences between three particular *C. difficile* strains are examined: the high-toxigenic VPI10463 strain (HTCD), the low-toxigenic strain ATCC630 (LTCD) and the non-toxigenic strain VPI11186 (NTCD). As per the Transmission Electron Microscopy (TEM) images at 50 k magnification in FIG. 12(a-c) and at 100 k magnification FIG. 12(d-f), the three *C. difficile* strains show-systematic variations in surface roughness in the cell wall region, with the highest roughness apparent in the HTCD strain (FIGS. 12a and 12d), followed by LTCD (FIGS. 12b and 12e) and finally the NTCD strain (FIGS. 12c and 12f), which exhibits relatively smooth surface features. One of the chief differences between the respective strains is the S-layer on their cell wall, which exhibits SIpA gene and Cwp gene sequence variations. Based on prior observations of a smoother cell surface for the S-layer deficient mutant *Tannerella forsythia* versus the wild type, we seek to correlate the inter-strain morphological differences in *C. difficile* to their S-layer variations, by using a standard adhesion assay. It has been shown that surface layer proteins are the chief determinant for the adherence of *C. difficile* to host cells and for binding to gastrointestinal tissues. FIG. 12g shows a representative phase contrast image of the adherence of HTCD to the human colon epithelial host cells after three wash steps. As per FIG. 12h, the HTCD strain shows the strongest adherence to the host cells, followed by LTCD and finally NTCD strains. This correlation of high cell wall roughness of the *C. difficile* strain-type to its enhanced host-cell adherence suggests an abundance of S-layer proteins within the HTCD strain, with successively lower S-layer protein levels within the LTCD and NTCD strains due to their relatively smoother features and poorer adhesion to the host cells. It is observed that the average cell wall thickness of the HTCD strain (32.1±3.8 nm) is lower than that of the NTCD strain (38.3±5.2 nm), as averaged over 10 cells.

Independent Dielectrophoretic Monitoring of Each *C. difficile* Strain.

Dielectraphoresis (DEP) of biological particles, such as *C. difficile*, can be characterized using a shell model. Herein, the net capacitance (C) due to the dielectric properties of the cell wall and membrane screens the electric field at low frequencies to cause negative DEP (nDEP), whereas the low resistance (R) due to conductive properties of the cytoplasm dominates at high frequencies to cause positive DEP (pDEP), with the crossover frequency ($f_{xo}$) from nDEP to pDEP being determined by the inverse of the RC time constant due to the net resistance and capacitance of the system. Based on a parallel-plate model for the cell wall with spacing: d, and material permittivity: ε, its capacitance rises with surface area (A):

$$C_{net} = \frac{\varepsilon A}{d} \quad \ldots \quad [1]$$

Changes in surface roughness and area of the cell wall would cause systematic differences in the net capacitance of each *C. difficile* strain. Hence, based on the inter-strain differences in surface roughness in FIG. 12, HTCD strains should have the highest net capacitance, followed by the LTCD and then by the NTCD strains. The DEP crossover ($f_{xo}$) for each *C. difficile* strain can be related to these differences in net cell wall capacitance ($C_{net}$) at a given media conductivity ($\sigma_m$), as follows:

$$f_{xo} = \frac{\sigma_m}{\sqrt{2}\, \pi r C_{net}} \quad \ldots \quad [2]$$

Hence, we anticipate the lowest $f_{xo}$ for the HTCD strain, followed by that of the LTCD strain and finally the NTCD strain. However, in order to observe this systematic difference in $f_{xo}$ between the three strains, it is necessary to optimize the media conductivity ($\sigma_m$). Below a critical value of $\sigma_m$, the high resistance of the surrounding media will dominate the net RC time constant of the system, thereby driving the $f_{xo}$ to low values and making it insensitive to differences in wall capacitance between the three strains. On the other hand, above a critical $\sigma_m$ value, pDEP cannot be effectively observed (pDEP requires particle conductivity to exceed media conductivity), thereby posing complications towards determination of the $f_{xo}$, due to lack of a clear crossover. However, the need for conducting DEP measurements within media of a substantial conductivity level to enable the observation of differences in the $f_{xo}$ between *C. difficile* strains can be challenging, due to the disruptive effects of electrolysis, electrothermal flow and electro-permeabilization of cells within electrode-based DEP devices at substantial $\sigma_m$.

Figure 13:
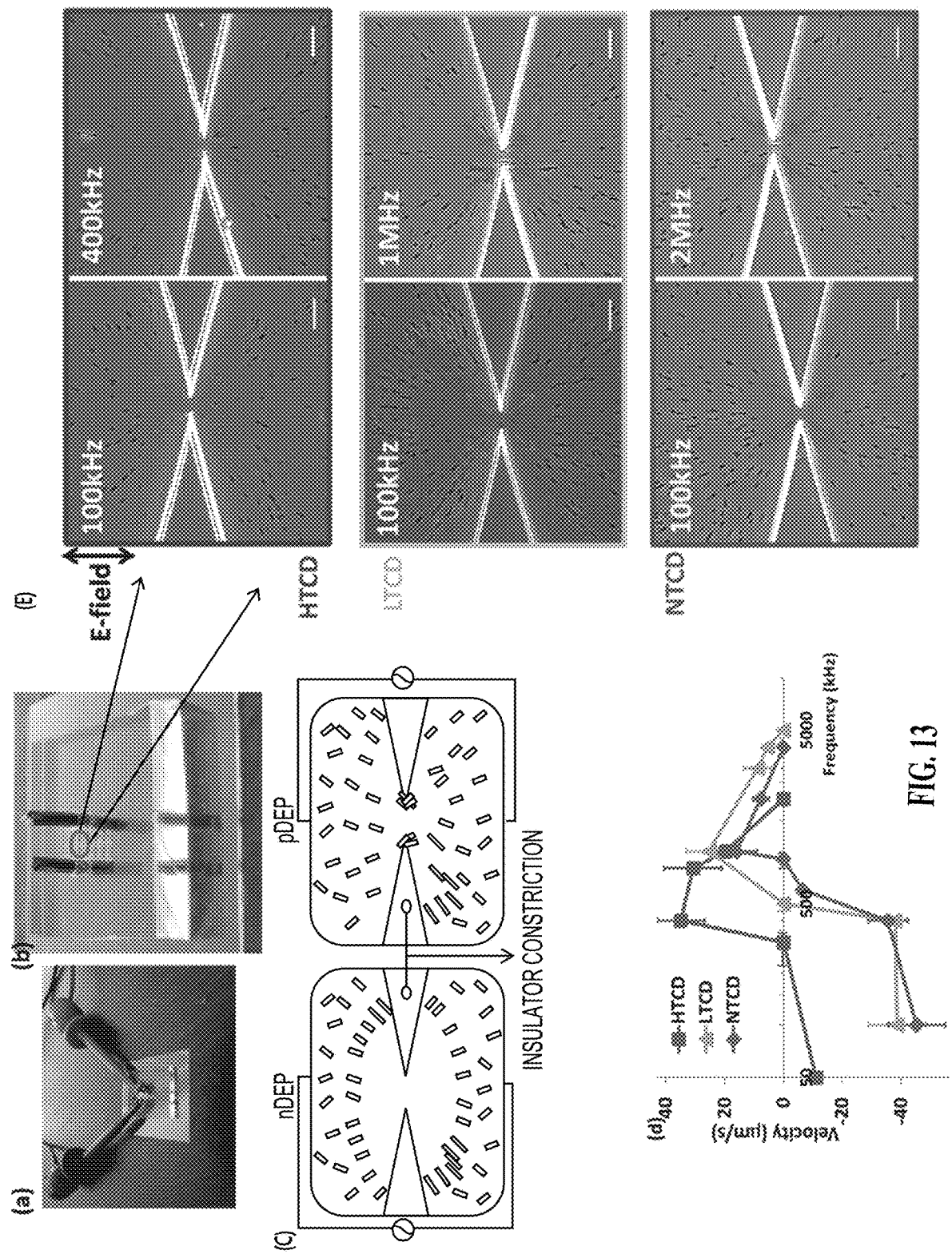
FIGS. 13:(a & b) Illustration of example electrode-less device with platinum electrodes (1 cm apart) for localized microbial trapping in the constriction region, (c) Illustration of DEP trapping within a constriction device, (d) Well-separated DEP spectra (velocity under $F_{DEP}$) for each strain: HTCD, LTCD and NTCD; (e) DEP behavior of each C. difficile strains in the constriction region after 30 seconds of AC field: 300 $V_{pp}$/cm of nDEP (1st column) at 100 kHz for all three strains or pDEP (2nd column) at 400 kHz, 1 and 2 MHz for HTCD, LTCD and NTCD, respectively. Scale bar: 30 μm FIG. 14:(a-c) Modification of dielectrophoretic spectra (velocity under DEP) can be used to monitor alterations after vancomycin treatment of (a) HTCD, (b) LTCD, and (c) NTCD strains. Note that reported velocities are averaged over 20 cells, of which an overwhelming majority (95-100%) exhibits the reported velocities, except for vancomycin treated cells at frequencies close to the DEP crossover, wherein this value drops to a 50-65% majority of the analyzed cells. (d) Alteration in the magnitude of the DEP response at 1 MHz (velocity under DEP) after vancomycin treatment and (e) change in DEP crossover frequency after vancomycin treatment offer information on alterations in cell electrophysiology.

Hence, in this current work, the influence of these disruptive effects on DEP observations is reduced by the use of electrode-less microfluidic devices, wherein heat dissipation is enhanced by using channels of high surface to volume ratio and wherein cell trapping under DEP does not occur at the electrode, but instead at or away from the tips of insulator constrictions that are designed to locally enhance electric fields. FIGS. 2a and 2b show the electrode-less device with external electrodes (1 cm apart) to initiate localized microbial trapping in the constriction region. This electrode-less device geometry also enables facile and automated dielectrophoretic tracking due to the well-defined particle trajectories, either towards (by pDEP) or away (by nDEP) from highly localized constriction tips (FIG. 13c), with a symmetric field profile across the device depth. In this manner, as per prior work[33], the translational velocity under the DEP trapping force is measured for ~20 individual microbial cells to quantify the DEP spectra. Upon optimization of $\sigma_m$ at: 100 mS/m, well separated DEP spectra for each strain are apparent, as per FIG. 13d. Example images in vicinity of the constriction region of the device after 30 seconds of ~300 $V_{pp}$/cm field at the optimal frequency for nDEP and pDEP behavior are shown in FIG. 13e for each strain, with arrows to denote the direction of translation and the respective velocity values at each frequency are reported in FIG. 13d. Based on this, while nDEP is highest at 100 kHz for all strains, the magnitude of the nDEP velocity is significantly lower for the HTCD strain versus the LTCD and NTCD strains. Furthermore, the crossover from nDEP to pDEP behavior occurs at successively lower values for the HTCD strain (300±75 kHz) versus the LTCD (500 kHz) and NTCD (900±75 kHz) strains, which is consistent with its progressively higher net wall capacitance due to higher surface area and lower cell wall thickness, as per the TEM images in FIG. 12. It is noteworthy that the absolute $f_{xo}$ value of the HTCD strain is significantly lower than the other strains, not only due to its higher cell wall capacitance, but also due to its significantly higher surface conductance, as judged by the lower magnitude of its nDEP velocity at low frequencies versus other strains. Also apparent, is the successive reduction in the magnitude of maximum positive DEP force levels, from highest for HTCD to a lower level for LTCD to lowest for the NTCD strain, which indicates a gradual reduction in cytoplasm polarizability for the respective strains, since their sizes are identical. While the magnitude of highest pDEP occurs at 400 kHz for the HTCD strain, it occurs at 1 MHz for the LTCD and NTCD strains. Finally, it is apparent that in spite of the reduction in cytoplasm polarizability for the NTCD strain versus other strains, a discernible level of positive DEP can be observed up to ~2 MHz with the NTCD strain, up to ~3 MHz with the LTCD strain and up to ~1 MHz with the HTCD strain.

These characteristic spectral features in the 0.05-5 MHz range; i.e. the $f_{xo}$, the frequency and magnitude of maximum pDEP and the frequency bandwidth for pDEP, can offer the means to separate intact microbials of the three strains from each other and possibly from other microbial species within heterogeneous samples. More generally, since numerous other gram-positive and gram-negative microbials exhibit S-layer variations, these results with *C. difficile* suggest the broader applicability of frequency-resolved DEP spectra towards inter-strain distinctions.

Alterations to Each *C. difficile* Strain Upon Vancomycin Treatment.

Figure 14:
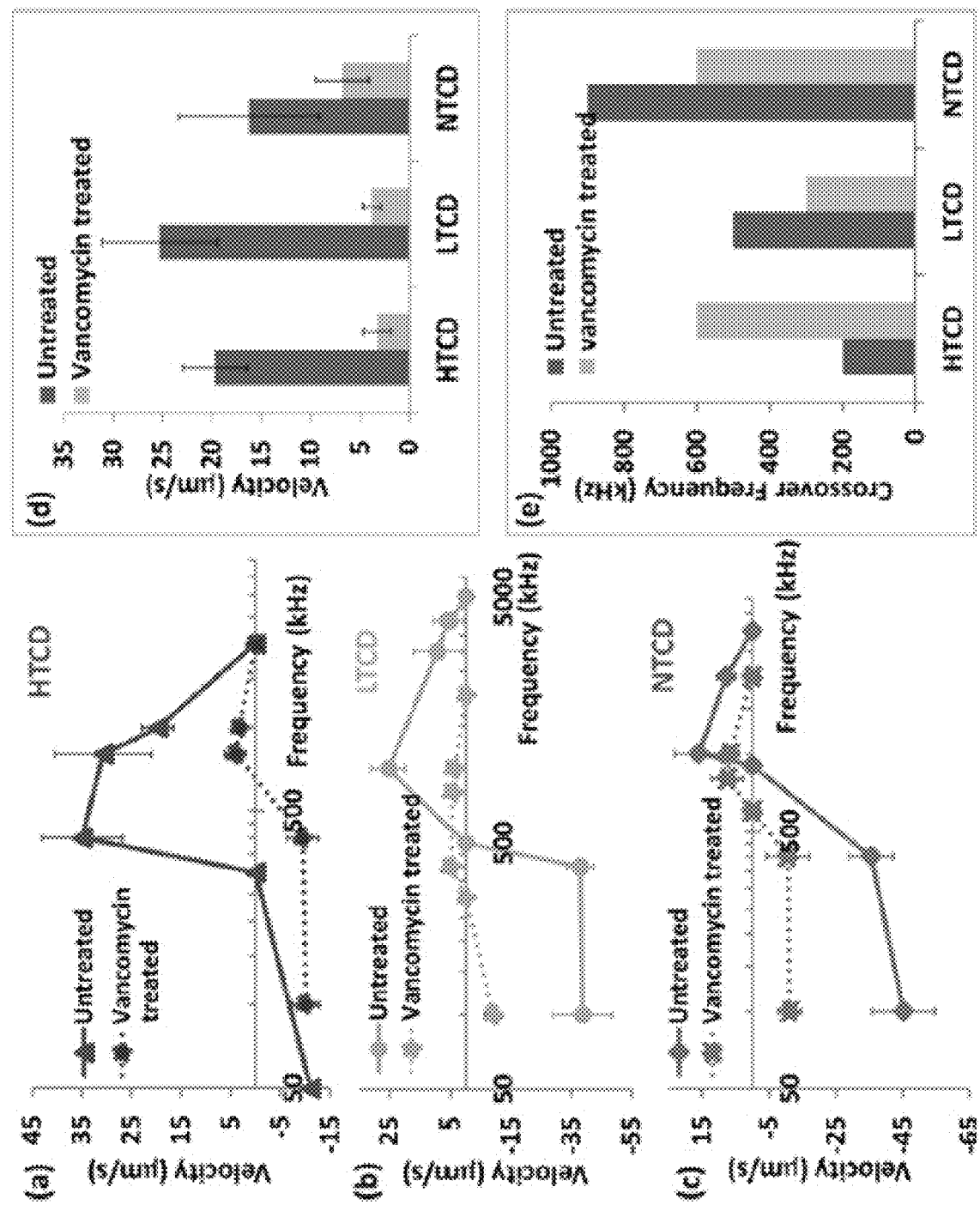

Alterations to the electrophysiology of cells upon antibiotic treatment, such as distinguishing the degree of cell wall permeabilization versus cytoplasm disruption, can be quantified by analyzing the dielectrophoretic frequency spectra of treated versus untreated cells. Herein, we utilize DEP to probe relative differences in the mechanism of microbial disruption for each *C. difficile* strain after vancomycin treatment, especially since similar measurements based on toxin production and growth rate can only indicate the altered functionality after vancomycin treatment, without providing information on the disruption mechanism, Furthermore, DEP spectra can offer information on the optimal frequencies for separating vancomycin treated cells from untreated cells of each *C. difficile* strain, thereby enabling a means for quantifying the efficacy of vancomycin treatment on each strain, especially within heterogeneous samples. In general, all the three strains become less polarizable due to functionality alterations to the cell after 24 hours of vancomycin treatment. However; the HTCD strain requires almost twice as much vancomycin levels than required for LTCD and NTCD strains to cause alterations to the DEP spectra. As a result of vancomycin treatment, while the DEP spectra for the HTCD strain (FIG. 14a) is shifted towards a higher crossover frequency (300 kHz to 600 kHz); the spectra for the LTCD strain (FIG. 14b) and the NTCD strain (FIG. 14c) are shifted towards successively lower crossover frequencies (500 kHz to 300 kHz for LTCD and 900 kHz to 600 kHz for NTCD). To quantify the relative alterations after vancomycin treatment, we show the steady reduction in DEP velocity for each strain at 1 MHz (FIG. 14d) and the changes in crossover frequencies (FIG. 14e). It is likely that vancomycin treatment alters the permeability of the cell wall and membrane regions, so that the lowered inverse RC time constant of the system enables DEP crossover at earlier frequencies, as observed for the NTCD and LTCD strains. For the HTCD strain, on the other hand, the need for higher vancomycin levels to cause alterations and the up-shifting of the DEP crossover frequency after vancomycin treatment suggests a relatively sturdier cell wall and membrane that is not easily permeabilized, in comparison to the LTCD and NTCD strains. This is somewhat consistent with prior observations that infer the need for higher antibiotic levels to deactivate HTCD strains versus others.

Benchmarking DEP Velocities to Toxin Production and Growth Rate

In order to evaluate the sensitivity of DEP methods versus the current state of the art, we benchmark the DEP velocity data for HTCD and NTCD *C. difficile* strains after various levels of antibiotic treatment versus conventional diagnostic measures for the loss of *C. difficile* functionality, such as toxin production and growth rate values. To enable the comparison of DEP data across the range of *C. difficile* strains, we choose a frequency of 1 MHz, since all strains show some level of pDEP before and after antibiotic treatment. For measurements of alteration in toxin production level and growth rate of *C. difficile* strains after antibiotic treatment, it is necessary to culture the microbial cells with the antibiotic over a period of 4-24 hours, to enable sufficient sensitivity for the measurements. Hence, these results on the untreated or antibiotic treated microbials are reported as a proportion of their respective value versus that after a "0 hour culture time" (indexed as "1"). Furthermore, the results after antibiotic treatment for a particular period of time are compared against their respective values on untreated microbials for the same period of culture time (this control value for each treatment time is indicated as "Un-0", "Un-4" or "Un-24" in FIGS. 15c-15e).

Figure 15:
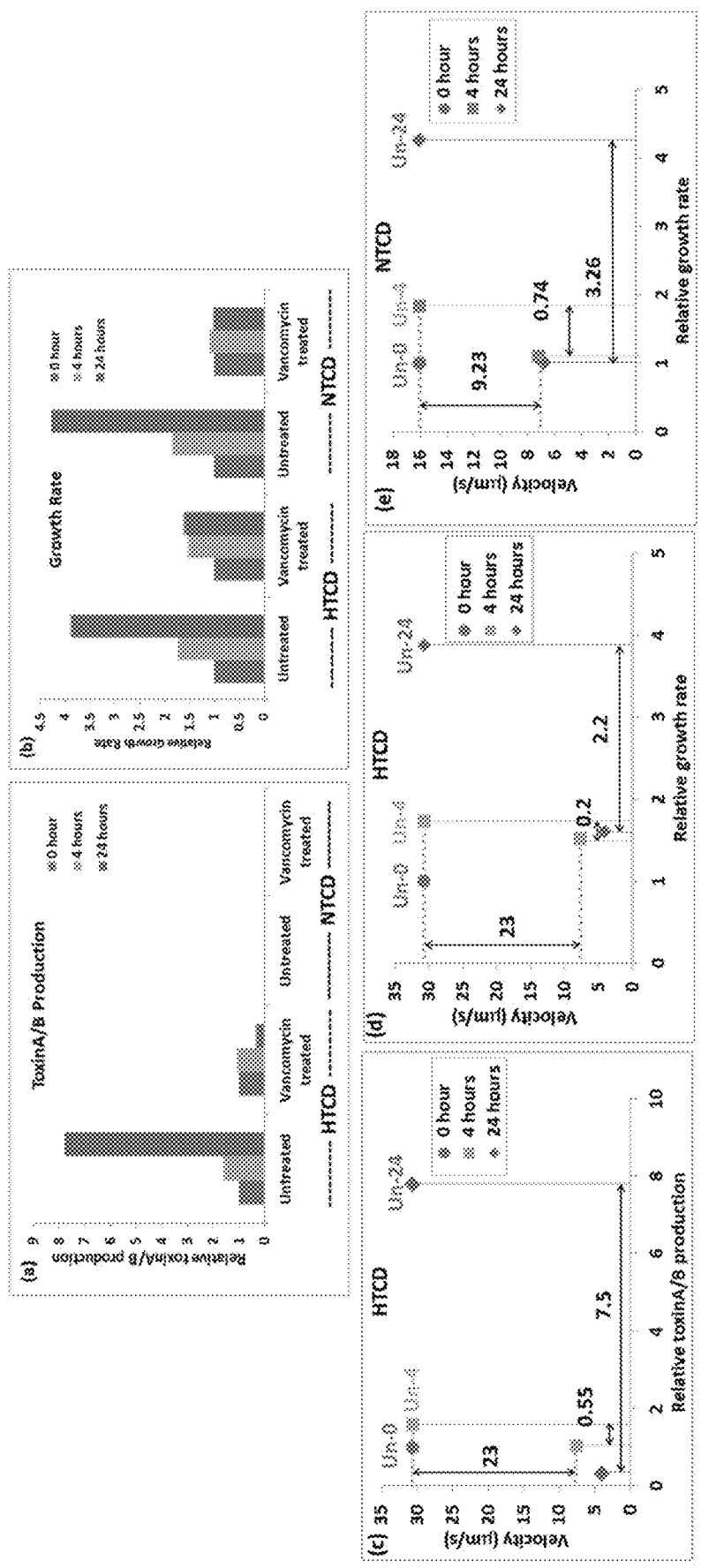
FIG. 15:(a) Relative toxin production and (b) relative growth rate for HTCD and NTCD strains before and after vancomycin treatment at 0, 4 and 24 hours. The data points after 4 hours and 24 hours of treatment are normalized to their respective value at the 0 hour time point. The differences in microbial toxin production (c for HTCD) and growth rate (d for HTCD & e for NTCD) after vancomycin treatment are compared versus the control (0 hour treatment) as arrows in X-direction, while the alterations in DEP response after each treatment are shown as arrows in the Y-direction. Note that the respective control value for the Untreated sample at various time points is shown as: Un-0, Un-4 and Un-24 (controls are invariant for DEP data but not so for toxin production and growth rate data).

Since DEP velocity measurements do not require microbial culture to enhance sensitivity, the "control" measurement for DEP velocity of untreated *C. difficile* is invariant with antibiotic treatment time. FIG. 15a shows the steady exponential rise in toxin production levels with culture time for the untreated HTCD strain, while the alterations upon vancomycin treatment lead to only a mild rise (1.05 times) after 4 hours of treatment and a small reduction after 24 hours treatment, due to degradation of residual toxin level. The data also shows that the NTCD strain cannot be quantified by this method due to absence of toxin production. The growth rate data in FIG. 15b follows a similar trend, with the untreated samples showing a steady exponential rise over time, whereas the vancomycin treated HTCD sample shows only a mild rise to 1.51 and 1.61 times after 4 and 24 hours respectively, and the vancomycin treated NTCD sample shows only a minimal rise to 1.1 and 1.05 times, after 4 and 24 hours, respectively. Next, the DEP velocity data after various treatment periods (4 and 24 hours) is compared to the toxin production level for the HTCD strain (FIG. 15c), the growth rate data for the HTCD strain (FIG. 15d) and the growth rate data for the NTCD strain (FIG. 15e) aver the same treatment periods (4 and 24 hours), with the respective value for the untreated sample at the same time period serving as the "control" (Un-0, Un-4 or Un-24). As per the toxin production levels in FIG. 15c, while alterations to the HTCD strain are apparent after 24 hours of vancomycin treatment; i.e. a difference of 7.5 versus the control (Un-24) as per red solid lines along the X-direction, the alteration is just barely apparent after 4 hours of vancomycin treatment; i.e. a difference of just 0.55 versus the control (Un-4) as per green solid lines along the X-direction). On the other hand, the DEP data shows a significant reduction in velocity, from 30.7 µm/s to 7.6 µm/s (green dashed lines in the Y-direction), right from the first time point of 4 hours of vancomycin treatment, with further reduction to 4 I.Un/s after 24 hours of vancomycin treatment. Similarly, the growth rate reduction of the HTCD strain is clear only after 24 hours of vancomycin treatment in FIG. 15d, with a difference of 2.2 versus the control (Un-24), as per red solid tines in the X-direction. In comparison to the minimal growth rate reduction in the HTCD strain after 4 hours of vancomycin treatment, the respective reduction in the DEP velocity is substantial for the same 4 hour treatment time. For the NTCD strain, while the reduction in growth rate is apparent in FIG. 15e after 24 hours of vancomycin treatment; i.e. a difference of 3.3 versus the untreated sample (Un-24) as per red solid lines in the X-direction, the alteration is not easily distinguishable after 4 hours of vancomycin treatment; i.e. a difference of 0.74 versus the untreated sample (Un-4), as per green solid lines in the X-direction. On the other hand, just as with the HTCD strain, reduction in the DEP velocity is substantial (16 µm/s to ~7 µm/s) right from the first time point of 4 hours of vancomycin treatment, as per green dash lines in the Y-direction. Hence, DEP methods are capable of more sensitively probing alterations in microbial physiology during antibiotic therapies on a variety of *C. difficile* strains, without the need for multiple control experiments, thereby enabling their application towards the optimization of antibiotics without the need for additional microbial culture.

Figure 16:
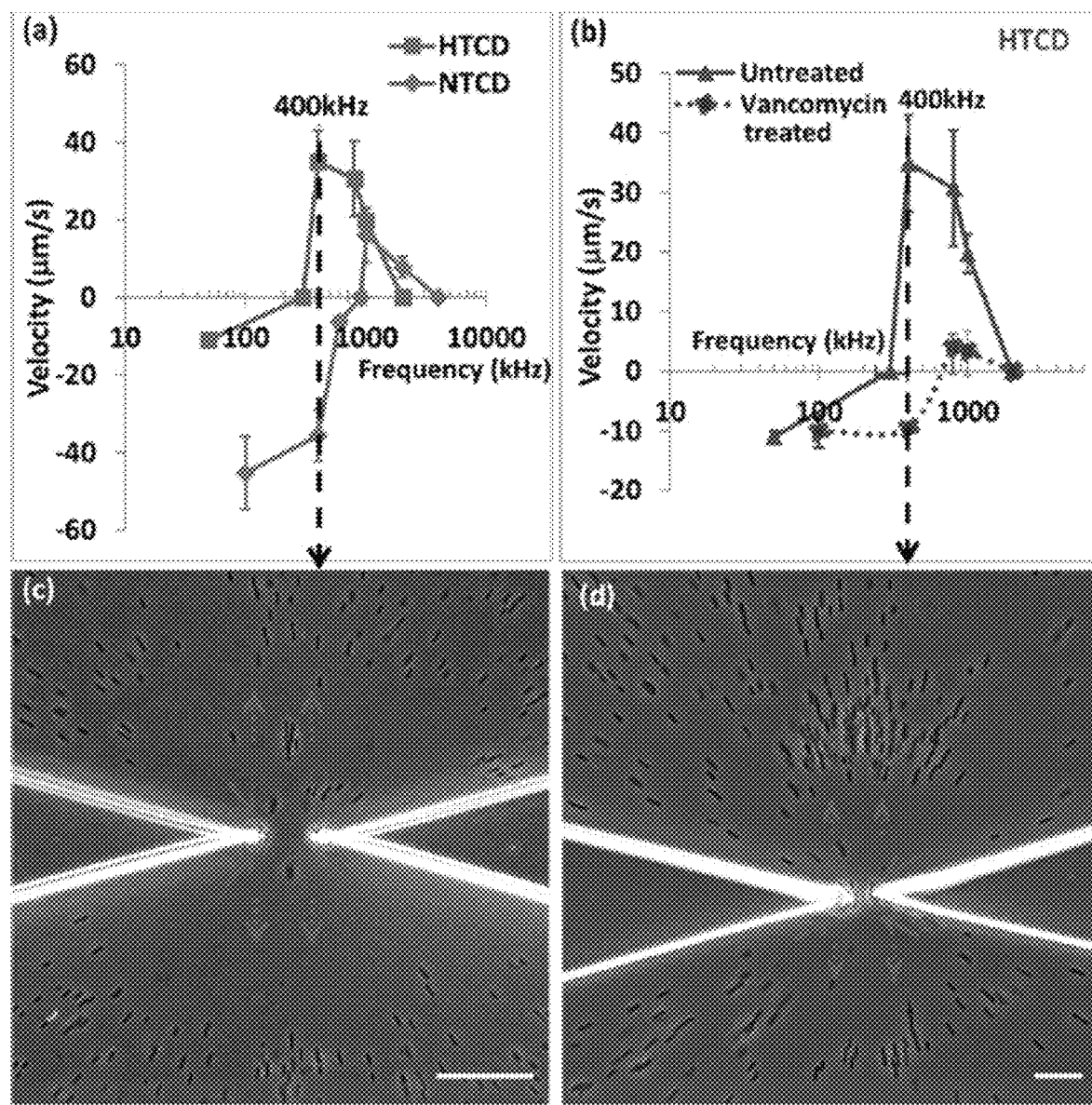
FIG. 16:(a) Dielectrophoretic spectra of HTCD versus NTCD; (b) DEP spectra of HTCD after vancomycin treatment; (c) At 400 kHz, HTCD strain shows pDEP (solid arrows) versus NTCD strain shows nDEP (dotted arrows); (d) at 400 kHz, untreated HTCD strain shows pDEP (solid arrows) versus vancomycin treated HTCD strain shows nDEP (dotted arrows). Scale bar: 30 μm

Separations from mixed *C. difficile* samples based on electrophysiology. The quantitative DEP response measurements in FIG. 13a and FIG. 14 suggest that through identifying an appropriate frequency, particular *C. difficile* strains may be separated from others within a mixed sample or after antibiotic treatment, based on differences in DEP force magnitude and direction. For the separation of a subpopulation of HTCD strains from a majority population of NTCD strains, we choose the frequency of 400 kHz, at which the HTCD strain exhibits strong pDEP behavior, while the NTCD strain continues to exhibit substantial nDEP. It is apparent from FIG. 16c, that such a separation can be accomplished in a facile manner, as confirmed by the DEP response and toxin production levels measured from pDEP trapped *C. difficile*. Similarly, vancomycin treated HTCD samples can be separated from untreated HTCD strains based on differences in their DEP behavior at 400 kHz (FIG. 16d), with untreated HTCD strains showing pDEP (red solid arrows), whereas the vancomycin treated HTCD samples show some residual level of nDEP (red dotted arrow), thereby presenting a methodology to quantify the effectiveness of antibiotic treatments based on the DEP collection rate.

In summary, we demonstrate that morphological differences in the cell wall region of *C. difficile* strains, presumably due to differing S-layer glyco-protein levels, cause systematic variations in their crossover frequency for transition from negative to positive dielectrophoresis (DEP) behavior, due to differences in the net cell wall capacitance. As a result, the DEP spectra exhibit characteristic features that may be applied towards independently monitoring each *C. difficile* strain, as well as towards inter-strain separation of intact cells from mixed microbial samples. Through benchmarking the DEP data against conventional measures of *C. difficile* activity, such as toxin production and growth rate, we demonstrate its superior sensitivity towards characterizing microbial alterations upon vancomycin treatment, thereby enabling the application of DEP methods towards the optimization of antibiotic treatments. Finally, through appropriate choice of frequency of the applied field, we demonstrate proof-of-concept separation of subpopulations of high-toxigenic *C. difficile* strains from a sample of non-toxigenic *C. difficile*, based on the magnitude and direction of their dielectrophoresis behavior thereby presenting a methodology for isolation of individual strains from mixed samples, quantification of antibiotic treatments and the engineering of nutrient environments to control microbiomes.

See related articles (each of which is incorporated herein by reference):

(1) Carroll et al., Annu Rev Microbiol 2011, 65, 501-521.
(2) Natarajan et al., Anaerobe 2013, 22, 1-5.
(3) Nagaro et al., Antimicrob Agents Chemother 2013, 57, 5266-5270.
(4) Villano et al., Antimicrob Agents Chemother 2012, 56, 5224-5229.
(5) Marsh et al., Current protocols in microbiology 2013, 30, 9A 3 1-9.
(6) Cohen et al., Society for Healthcare Epidemiology of, A.; Infectious Diseases Society of, A. Infection control and hospital epidemiology: the official journal of the Society of Hospital Epidemiologists of America 2010, 31, 431-455.
(7) Hunt, J. J.; Ballard, J. D. Microbiology and molecular biology reviews: MMBR 2013, 77, 567-581.
(8) Spigaglia, P.; Mastrantonio, P. Journal of clinical microbiology 2002, 40, 3470-3475.
(9) Sleytr et al., FEMS microbiology reviews 2014.
(10) Fagan, R. P.; Fairweather, N. F. Nature reviews. Microbiology 2014, 12, 211-222.
(11) Reynolds et al., PLoS pathogens 2011, 7, e1002024.
(12) Spigaglia et al., Journal of medical microbiology 2013, 62, 1386-1393.
(13) Mukherjee et al., Microbiology 2002, 148, 2245-2253.
(14) Karjalainen et al., A. Journal of clinical microbiology 2002, 40, 2452-2458.
(15) Sekot et al., Journal of dental research 2011, 90, 109-114.
(16) Sara, M.; Sleytr, U. B. Journal of bacteriology 2000, 182, 859-868.
(17) Sara et al., Journal of bacteriology 1996, 178, 2108-2117.
(18) Casademont et al., FEMS immunology and medical microbiology 1998, 21, 269-281.
(19) Ventura et al., FEMS microbiology letters 2000, 189, 275-279.
(20) Jones, T. B. Electromechanics of Particles; Cambridge, New York: Cambridge University Press, 2005.
(21) Green, H. M. a. N. G. AC Electrokinetics: Colloids and Nanoparticles; Res. Studies Pr., 2003.
(22) Pethig, R. Biomicrofluidics 2010, 4, 022811.
(23) Morgan et al., J Phys D Appl Phys 2007, 40, 61-67.
(24) Lapizco-Encinas et al., Analytical chemistry 2004, 76, 1571-1579.
(25) Hawkins et al., Analytical chemistry 2011, 83, 3507-3515.
(26) Hoettges et al., Analytical chemistry 2008, 80, 2063-2068.
(27) Rohani et al., Electrophoresis 2014, 35, 1795-1802.
(28) Gascoyne et al., Electrophoresis 2013, 34, 1042-1050.

(29) Jones et al., Analytical and bioanalytical chemistry 2014, 406, 183-192.

(30) Braff et al., PloS one 2013, 8, e76751.

(31) Farmehini et al., Lab on a chip 2014, 14, 4183-4187.

(32) Su et al., The Analyst 2014, 139, 66-73.

(33) Trejo et al., Anaerobe 2006, 12, 186-193.

(34) Merrigan et al., PloS one 2013, 8, e78404.

(35) Chaurey et al., Electrophoresis 2013, 34, 1097-1104.

(36) Calabi et al., Infection and immunity 2002, 70, 5770-5778.

(37) Hawkins, B. G.; Kirby, B. J. Electrophoresis 2010, 31, 3622-3633.

(38) Xuan, X. Electrophoresis 2008, 29, 33-43.

(39) Nakano et al., Analytical chemistry 2014, 86, 6516-6524.

(40) Sanghavi et al., Anal. Chem. 2014, 86, 4120-4125.

(41) Liao et al., Electrophoresis 2012, 33, 1958-1966.

(42) Hoettges et al., Physics in medicine and biology 2007, 52, 6001-6009.

(43) Gerber et al., Journal of medical microbiology 2008, 57, 776-783.

Dielectrophoretic Tracking of Subpopulations of *Cryptosporidium Parvum*

Microbial persistence to antibiotics is attributed to subpopulations with phenotypic variations that cause a spread of susceptibility levels, leading to the recurrence of infections and stability of biofilms. Herein, persistent oocyst subpopulations identified by animal infectivity and excystation assays during the disinfection of *Cryptosporidium parvum*, a water-borne pathogen capable of causing enteric infections at ultra-low doses, are separated and characterized by quantitative dielectrophoretic tracking over a wide frequency range (10 kHz-10 MHz). To enable the simultaneous and facile dielectrophoretic tracking of individual oocysts, insulator constrictions in a microfluidic channel are utilized to spatially modulate the localized field over the extent needed for defining oocyst trajectories and for obtaining high-resolution displacement versus time measurements under both, positive and negative dielectrophoresis. This manner, by obviating the need for averaging dielectrophoretic data over a large collection region, the force response is more sensitive to differences in electrophysiology from sub-population fractions. Hence, the electrophysiology of sensitive and persistent oocysts after heat and silver nanoparticle treatments can be quantified by correlating the force response at low frequencies (<100 kHz) to the integrity of the oocyst wall and at high frequencies (0.4-1 MHz) to the sporozoites in the oocyst. This label-free method can characterize heterogeneous microbial samples with subpopulations of phenotypically different alterations, for quantifying the intensity of alteration and fraction with a particular alteration type.

Micro-organism samples are usually spread over developmental lifecycles and subpopulations, leading to their persistence due to altered levels of susceptibility to antibiotics. The sensitive quantification of these heterogeneous modifications is a major challenge, especially for subpopulations with phenotypic rather than genotypic variations and for organisms that cannot be enriched in vitro by microbial culture methods. The case of *Cryptosporidium parvum*, an oocyst forming protozoan parasite species (henceforth called *C. parvum* oocysts) illustrates this problem. Ingestion of *C. parvum* oocysts, which are not deactivated by the standard chlorine treatments, leads to Cryptosporidiosis, which is estimated to be responsible for about 50% of the waterborne diseases attributed to parasites worldwide. On one hand, there is a need to sensitively quantify alterations to the oocyst by disinfectants, since as few as ten viable oocysts of the billion oocysts shed by a host during an infection episode, are sufficient to cause a new infection. On the other hand, the heterogeneous nature of the alterations during disinfection, due to subpopulations in the sample, leads to substantial variations in oocyst viability. Hence, a relatively high concentration of $\sim 10^6$ oocysts per mL is required within in vivo infectivity tests on animal models to enable quantitative assessments on modifications to oocyst viability. Additionally, the lack of means to proliferate the oocysts limits the sensitivity of in vitro monitoring methods, since *C. parvum* oocysts typically only excyst and complete their lifecycle in the mammalian gastrointestinal tract. Biomolecular assessment of viability based on hsp70 mRNA levels is highly sensitive, but unsuitable for real-time monitoring during disinfection or in cases where subsequent analysis is needed on the oocysts. Hence, there is a need to separate and enrich oocysts with particular alterations for quantification of each subpopulation.

Dielectrophoresis (DEP) causes frequency-selective translation of polarized bio-particles in a non-uniform field, either towards or away from high field regions within a device, depending on the polarizability of the bio-particle versus that of the medium. Some of the distinguishing features of DEP include: (a) its highly sensitive, label-free and non-destructive characterization methodology that is dependent only on the inherent dielectric properties of single bio-particles; (b) its ability to probe different dielectric regions of the bio-particle, such as its non-conducting shell versus its conducting core, based on appropriate choice of frequency of the field; and: (c) its ability to separate and enrich particular bio-particles of interest versus others in the media, due to its frequency-selectivity. Hence, DEP is widely investigated for sample enrichment and sensing of tumor cells, micro-organisms, viruses, nucleic acids, proteins, and for drug screening. While the need for microfluidic systems to enhance DEP trapping forces has limited its suitability for high throughput applications (>1 mL), it is well suited for probing subtle distinctions in micro-organisms after their immuno-magnetic separation from large water systems. Dielectrophoretie, and electro-rotation techniques have been applied previously to investigate modifications to the oocyst wall of *C. parvum* after heat treatment. However, no prior work has quantitatively correlated the DEP behavior to the modifications in structure and infectivity of sporozoites in the oocyst. This is necessary for the separation of oocysts based on sporozoite structure to discern the effectiveness of disinfectants, since infections are caused by the release of sporozoites from the oocyst. Silver nanoparticles (AgNP) show an enhanced antimicrobial effect over silver salts, and have been widely investigated for water disinfection applications.

Quantitative DEP characterization of cell electrophysiology can be accomplished through methods such as, measuring the DEP collection rate, determining the DEP crossover frequency of cells, measuring the DEP levitation height of cells or through actively tracking the translation of cells under DEP. However, a limitation within all these techniques is the lack of means to define the trajectory of the cells under DEP behavior, especially under negative DEP. Hence, the data needs to be averaged over a large number of cells that are trapped over an ill-defined region of the device, thereby making them less sensitive to variations from small fractions of persistent subpopulations, such as: $10^{-5}$-$10^{-6}$ of the total population for *E coli*, that is phenotypically distinct and resistant to antibiotics. Herein, we utilize insulator constrictions within a microfluidic device to localize the field symmetrically across the device depth and modulate the lateral field gradient over a specified spatial extent, thereby defining the trajectory of microbial cells under both, positive and negative DEP behavior. This enables the simultaneous and facile dielectrophoretic tracking of individual *C. parvum* oocysts during positive and negative DEP over a wide frequency range (10 kHz-10 MHz). As a result, the electrophysiology of sensitive and persistent subpopulations can be quantified in parallel, by identifying a frequency for their separation based on the magnitude and direction of the DEP trapping force. In this manner, the intensity of alteration of a subpopulation can be monitored by correlating the DEP tracking data to the integrity of their oocyst wall and sporozoites in the oocyst, while the fraction of oocysts with a particular alteration can be quantified by DEP collection data.

Preparation of *Cryptosporidium parvum* Oocysts

*Cryptosporidium parvum* oocysts were purchased from Waterborne Inc. and stored at 4° C., until use. All the oocysts from a particular batch were used within a month, since oocysts undergo significant de-activation over time. The media conductivity ($\sigma_m$) of oocyst stock ($10^9$/50 mL in phosphate-buffered saline) was lowered to 2 mS $m^{-1}$, by centrifuging the oocysts (Eppendorf 5430), aspirating the supernatant and resuspending the oocysts in DI water by vortexing to prevent aggregation or sedimentation.

Disinfection Treatments on Oocysts

For heat treatment, the oocysts were placed in a dry block/shaker (Thermomixer, Eppendorf) at 90° C. for 10 minutes with 300 rpm shaking to allow homogenous heat distribution. An alternate treatment at 70° C. for 5 minutes, which is the minimal level required for a loss of infectivity within the mouse model,' was also studied for isolating persistent subpopulations with less intense modifications to the oocyst. For treatment with silver nanoparticles (AgNPs), the animal infectivity experiment was done after the oocysts were treated with 100 mg $L^{-1}$ proteinate capped AgNPs (Argenol) (~15 nm) for 4 hours. While disinfection treatments were carried out over a 4 hours period, continuous DEP monitoring was used to confirm that steady state levels of oocyst deactivation were reached within 20 minutes for each treatment. For silver nitrate ($AgNO_3$) (Fisher Scientific) treatment, oocysts were treated with 100 mg $L^{-1}$ $AgNO_3$ for 4 hours.

Fluorescence Monitoring of Oocysts

4',6-diamidino-2-phenylindole (DAPI) and propidium iodide (PI) were prepared in DI water to a stock concentration of 1 mg $mL^{-1}$ by standard methods. The suspension of oocysts from each treatment was placed for 45 minutes in diluted DAPI (final concentration: 2 μg $mL^{-1}$) and then for 15 minutes in diluted PI (final concentration: 0.2 μg $mL^{-1}$). After an hour treatment with the fluorescent dyes, the oocysts were centrifuged, aspirated and re-suspended in DI water by vortexing to prevent any aggregation and sedimentation. The wash steps were repeated twice to eliminate the background signal. Images were acquired using a Zeiss Observer Z1 microscope with a 63× oil immersion objective lens under bright field view for phase and Differential Interference Contrast (DIC) images, and fluorescent view for DAPI and PI images.

Excystation of Oocysts and Mouse Model Infectivity Studies

After each disinfection treatment, the oocysts were treated with 10% bleach (Bleach-Rite) for 30 minutes in a microcentrifuge tube at room temperature, followed by vortexing every 10 minutes. The suspension was incubated in a microfluidic chamber with a glass cover-slip for an hour, for real-time recording of the excystation; i.e. release of sporozoites from the oocyst. The excystation was examined by inverted microscopy using 63× oil immersion phase and DIC objectives. At least ten different fields of view were taken (Hammatsu Orca Flash4) and results from at least 300 oocysts were used to calculate the net ex-cystation rate for each treatment. The percentage of the excystation was calculated as: (# of excysted oocytsl # of total oocyst)×100.[29] For mouse model infectivity studies,[12] all mice were malnourished for a period of 13 days before experiments. For every six mice fed with the oocysts for each treatment, three other mice were fed with untreated oocysts as positive control. RT-PCR analysis was performed on stool shed from mice from the day after inoculation to day 7, post-infection.

Dielectrophoretic Characterization of Oocysts

The schematic set-up utilized for the DEP studies on the oocysts is shown in FIG. 2. Standard PDMS (poly-di-methyl-siloxane) micro-molding methods were used to microfabricate a channel of ~1 cm length and 15 μm depth, with several sharp lateral constrictions from 1500 μm to 15 μm and back to 1500 μm over a total extent of ~200 μm length (FIG. 2*b*). This so-called "constriction chip" was bonded using al minute oxygen plasma treatment to a glass coverslip for easy microscopic viewing of DEP behavior (FIG. 2*a*). After filling the micro-channel with the oocyst sample, Pt electrodes (Alfa Aesar) were inserted and sealed within the "inlet" and "outlet" to activate the electric field. AC fields were applied using a function generator (Agilent 33220 A) and a voltage amplifier (FLC) for fields of ~300 $V_{pp}$ $cm_{-1}$ at a frequency range of 1 kHz to 15 MHz. Under conditions for positive DEP (PDEP), the oocysts were translated towards the constriction tip (FIG. 2*c*) and under negative DEP (NDEP) they were translated away from the constriction tip (FIG. 2*d*). For spherical particles of radius: a, in a medium of permittivity: $\epsilon_m$, the DEP force ($F_{DEP}$) under an rms field: $E_{rms}$, depends on product of the localized field with its gradient ($\nabla E^2$) and the frequency-dependent complex dielectric contrast of the particle versus the medium, as given by real-part of the Claussius-Mossoti factor ($K_{CM}$):

$$F_{DEP} = 2\pi\alpha^3\varepsilon_m \mathrm{Re}\left(\frac{\varepsilon^*_{p-}\varepsilon^*_m}{\varepsilon^*_p + 2\varepsilon^*_m}\right)\nabla E_{rms^2} - 2\pi a^3\varepsilon_m \mathrm{Re}[K_{CM}(\omega)]\nabla E_{rms^2} \quad (1)$$

Here, E*, denotes the complex permittivity, and subscripts p and m, denote the respective property of the particle and medium, respectively. The frequency (ω) dependent permittivity (ε) is related to conductivity (o) as: ε*=ε+(σ/jω). Hence, at low frequencies (<1 MHz), the respective o terms dominate, whereas at high frequencies (>1 MHz), the respective E terms begin to play a significant role on the DEP response. Specifically, at low frequencies (<1 MHz):

$$F_{DEP} = 2\pi\alpha^3\varepsilon_m\left(\frac{\sigma_P - \sigma_m}{\sigma_P + 2\sigma_m}\right)\nabla E^2 \quad (2)$$

$F_{DEP}$ values were calculated by standard particle tracking methodologies[14] to monitor the displacement (x) of the oocysts over time (t) under NDEP or PDEP, based on data from high frame per second (~30 fps) movies. In this manner, the velocity (dx/dt) and acceleration ($d^2x/dt^2$) of the oocysts could be continuously tracked to compute $F_{DEP}$ using:

$$F_{DEP} = 6\pi\eta\alpha\frac{dx}{dt} = m\frac{d^2x}{dt^2} \qquad (3)$$

The force data was fit to a single shell model[28] to calculate the conductivity and permittivity of the shell composed of the oocyst wall ($\sigma_{wall}$ and $\varepsilon_{wall}$) and the core composed of the cytoplasm with the sporozoites ($\sigma_{cyto}$ and $\varepsilon_{cyto}$). Details of the particle tracking to measure the $F_{DEP}$ and computation of cell electrophysiology by fitting dielectric properties to the shell model are described in subsequent section and in ESI.

Identifying Persistent Subpopulations After Disinfection

Figure 17:
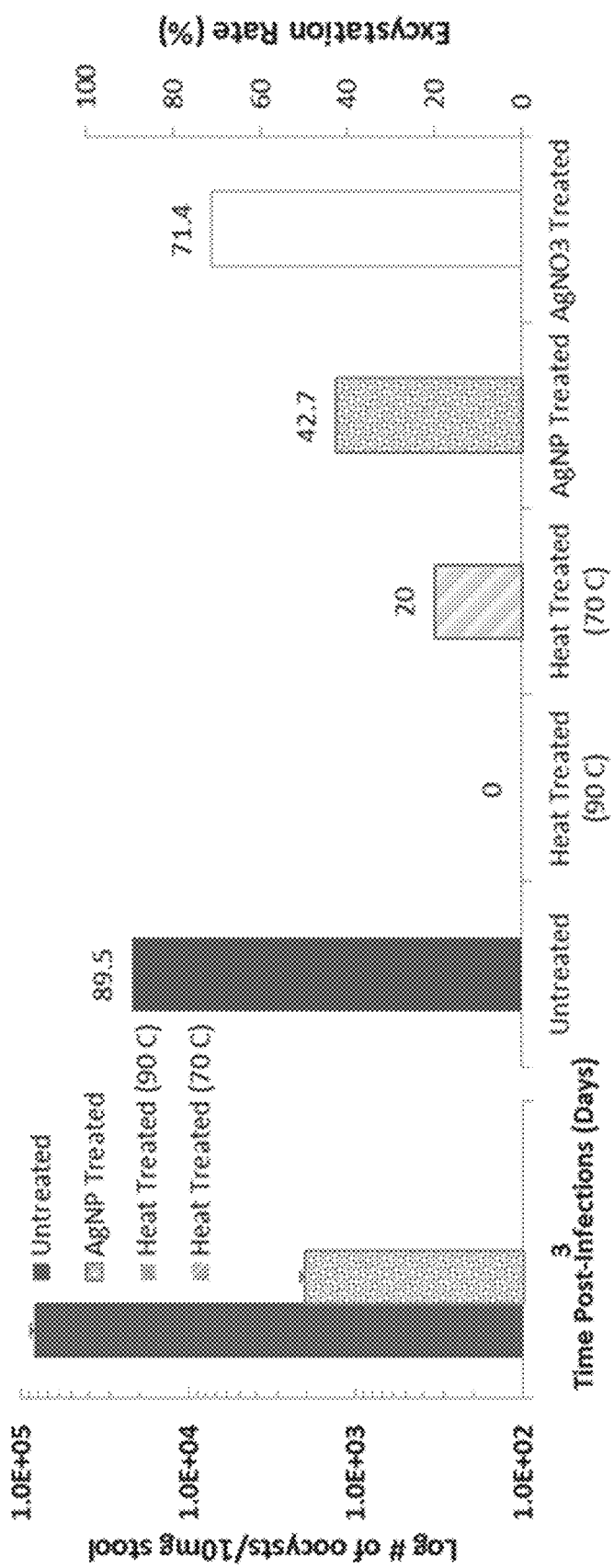
FIG. 17 depicts the functionality of sporozoites in the oocyst after disinfection treatments: (left) # of shed oocysts on day 3 of the infection on the mouse model; and (right) excystation rate. No oocysts shed after heat treatment.
Figure 18:
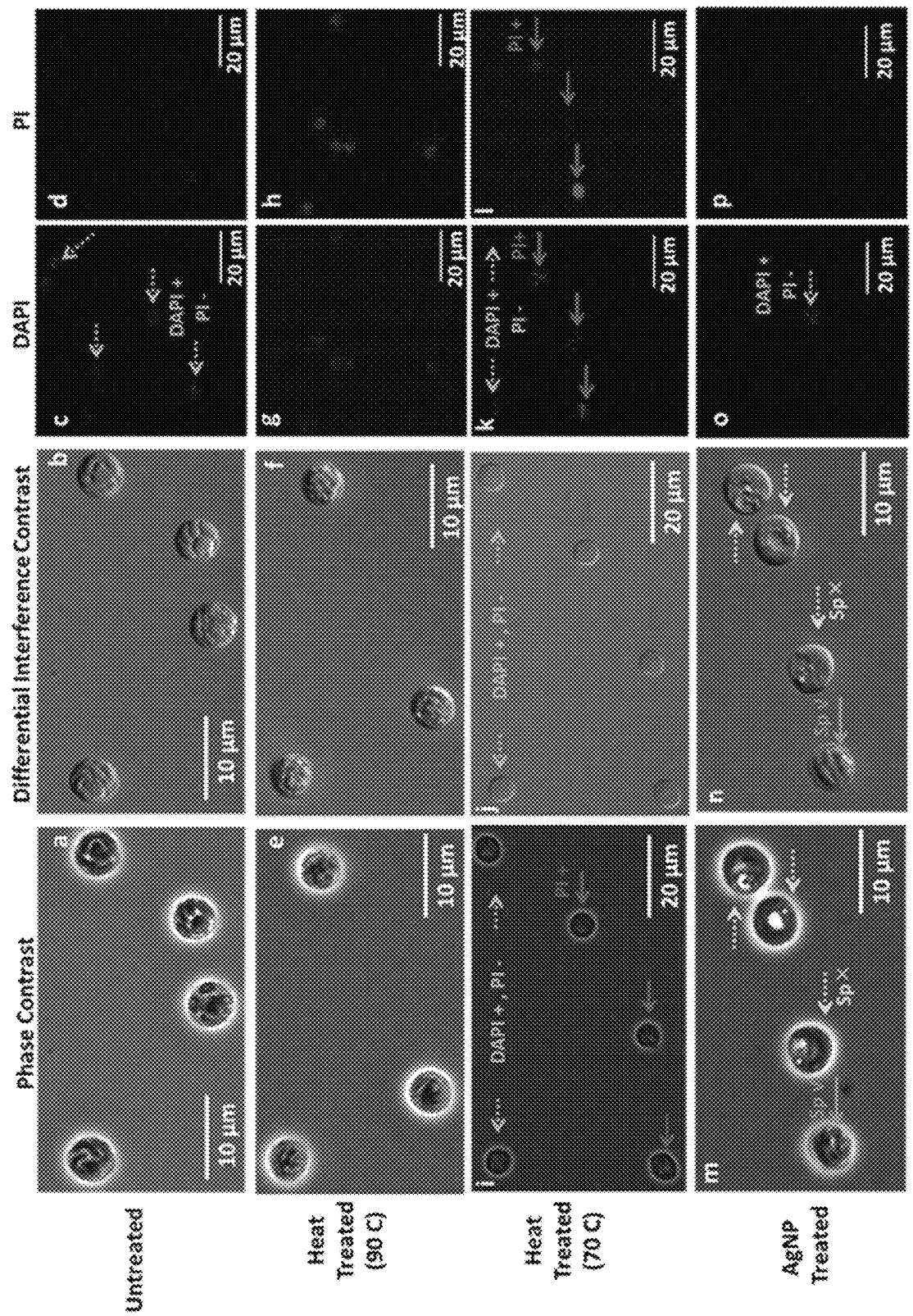
FIG. 18 show phase images, DIC images, and flourescence images of the heterogeneous modification of oocysts after disinfection treatments.

We begin with applying the excystation assay and infectivity tests on the mouse model to identify the persistent and sensitive subpopulations of C. parvum oocysts with differing phenotypic alterations after heat and AgNP treatment. As per FIG. 17 (left), based on # of oocysts shed from the mouse on Day 3 when the infection is most intense, as confirmed by the weight-loss data, the high infectivity of untreated oocysts is almost absent with heat treated oocysts at both, 90° C. and 70° C. Following AgNP treatment, while the infectivity of the oocysts is significantly reduced, it is still discernible. Based on the excys-tation rate (FIG. 17—right), it is clear that while 89.5% of the untreated oocysts undergo excystation, the rate drops to 71.4% after $AgNO_3$ treatment, to 42.7% after AgNP treatment, and to 20% and 0%, after heat treatment at 70° C. and 90° C., respectively. Together, these results suggest that while heat treatment of oocysts at 90° C. causes complete de-activation, there are persistent subpopulations of unactivated oocysts after heat treatment at 70° C. and after AgNP treatment. In comparison to AgNP treatment, the disinfectant effect of $AgNO_3$ is less significant, as apparent from the 70% excystation rate.

Heterogeneous Modification of Oocysts After Disinfection

The viability of sporozoites in the oocyst can be indicated by the banana-shaped sporozoite morphology in phase and DIC microscopy modes, and the presence of DAPI signal in fluorescence mode, whereas absence of PI signal indicates integrity of the oocyst wall. The distinct sporozoite structure of untreated oocysts is apparent in the phase contrast (FIG. 18*a*), and DIC images (FIG. 18*b*). Additionally, based on presence of DAPI labeling that delineates the four nuclei of the sporozoites (FIG. 18*c*) and the absence of PI labeling (FIG. 18*d*), henceforth labeled as: DAPI+/PI− (dotted green arrows), we infer the viability of the oocysts. Note that for clarity, the phase and DIC images in FIG. 18 are at higher magnification than the fluorescence images, but the respective images from the same field of view in ESI section (FIG. S3†) also illustrate these inferences. Heat treated oocysts at 90° C. do not show a discernible banana-shaped sporozoite structure. Instead, a nebulous sporozoite structure that is indistinguishable from the background is apparent under phase contrast (FIG. 18*e*) and DIC (FIG. 18*f*), alongside a diffuse level of DAPI labeling that is spread beyond the four nuclei of the sporozoites (FIG. 18*g*), suggesting a disorganized oocyst cytoplasm. Furthermore, the presence of PI labeling within the oocysts (FIG. 18*h*), indicates disruption of the oocyst wall, henceforth labeled as: PI+ (solid red arrows). Heat treated oocysts at 70° C. indicate heterogeneous modifications, with a subpopulation showing intact sporozoites with DAPI+/PI− labeling and another showing the destroyed oocyst wall with PI+ labeling (FIGS. 18*k* and l). The differential levels of PI signal from the PI+ labeled oocysts further indicates the heterogeneous modifications (FIG. 18*l*). Upon AgNP treatment, instead of the banana-shaped sporozoite structure, the phase contrast image of the oocyst cytoplasm reveals a transparent region composed of a coalesced cluster adjoining an empty region (FIG. 18*m*), with topographic differences in the DIC image (FIG. 18*n*) that suggest an altered sporozoite structure. However, there is a small group of AgNP treated oocysts that continue to show the distinct sporozoite morphology of untreated oocysts, as apparent from the red arrow with Sp √ in FIG. 18*m-n*. This sub-group of oocysts indicate the DAPI+/PI− signal delineating the nuclei of the sporozoites (FIG. 18O), whereas the other subgroup of AgNP treated oocysts with the altered sporozoite structure (Sp X) do not show any DAPI signal. The PI signal is uniformly absent from all AgNP treated oocysts (FIG. 18). Hence, optical microscopy confirms the heterogeneous modification of the oocysts after heat treatment at 70° C. and after AgNP treatment. Note that these treatments were carried out over ~4 hours to ensure steady-state behavior. After heat treatment at 70° C., there is a persistent subpopulation with intact occyst wall and sporozoite structure (DAPI+/PI−) and a sensitive subpopulation with a compromised occyst wall and diffuse sporozoite structure (PI+). After AgNP treatment, there is a persistent subpopulation with an intact sporozoite structure in the oocyst (Sp √) that indicates: DAPI+/PI− signal, whereas there is a sensitive subpopulation with an altered sporozoite structure in the oocyst (Sp X), but with an intact oocyst wall (i.e. DAPI− and PI−). We infer that while optical microscopy is qualitatively consistent with excystation and infectivity assays, which indicate the partial loss of sporozoite functionality due to sensitive and persistent subpopulations after AgNP treatment and heat treatment at 70° C., these techniques are unable to quantify the degree of oocyst alteration and number of oocysts with a particular alteration.

Simultaneous Dielectrophoretic Tracking of Single Oocysts

To quantify sensitive versus persistent oocyst subpopulations after heat treatment at 70° C. or after AgNP treatment, we characterize the differences in DEP behavior as a probe of cell electrophysiology. The capability of DEP for frequency-modulated characterization of oocysts, with selectivity to the properties of the oocyst wall at low frequencies and to the properties of the sporozoites in the cytoplasm at high frequencies, can enable electrophysiological monitoring of the oocysts, without the need for chemical alteration or wash steps, as would be required for fluorescence assays based on dye penetration and antibody binding schemes. Furthermore, this frequency-selective DEP behavior can be applied towards the separation and enrichment of oocysts due to their spatial localization based on their oocyst wall or sporozoite condition, thereby enabling the quantification of their heterogeneous modification by disinfectants. For this purpose, we continuously track the time evolution of displacement of the oocysts under DEP behavior within a constriction device. Prior methods have used interdigitated or quadrapole electrode devices to track the collection rate or velocity of polarized bio-particles under dielectrophoresis. The chief disadvantage of devices with electrodes for quantifying the DEP behavior is that since field lines must terminate normal to the electrode surface, the degree of spatial control of the field gradient across the lateral and depth directions is rather limited.

As indicated in FIGS. 3*a* and 3*b*, the sharp field non-uniformity laterally from 10 μm spaced interdigitated electrode edges will cause polarized bio-particles to be abruptly accelerated, only in close proximity of the electrode edge. Hence, under positive DEP, this sharp field profile does not allow for recording of significant displacement versus time points, especially for microbial and mammalian cells that extend over several microns. Furthermore, as depicted in FIG. 3c, the field non-uniformity vertically from the electrode causes differential influence of the field across the device depth. As a result, displacement tracking to quantify the DEP response is not accurate. While collection rate measurements can enable quantification, they will require averaging over a large region due to the ill-defined trapping region, which will make the data less sensitive to variations from fractional subpopulations. Quantifying negative DEP behavior presents even greater problems since the polarized bio-particles are translated along the device depth. While confocal microscopy can quantify the final position under negative DEP, active tracking at high frame rates is not possible. In this context, the insulator constriction within the device used in the current study enables an unprecedented degree of spatial control of the field to define the trajectory of the polarized bio-particles under both, positive and negative DEP. First, the high-field point is localized at the constriction tip and the gradient is modulated over a specified spatial extent of ~50 μm, as shown in FIGS. 3a and 3d. Hence, the trajectory of polarized bio-particles is well-defined; i.e. from the beginning of the field gradient to the constriction tip under positive DEP (FIG. 3g) and from the constriction tip to the end of the field gradient under negative DEP (FIG. 3h). Furthermore, since the constriction occurs uniformly across the device depth, the field profile is symmetric across the depth (FIG. 3e). Hence, all of the polarized bio-particles in the device within the vicinity of the field gradient due to the constriction are influenced uniformly, irrespective of their position within the device depth, whereas the differences in trapping force due to the lateral field non-uniformity can be normalized by the field gradient (FIG. 3d) along a particular trajectory. In this manner, since the particle trajectory is highly defined under both, positive and negative DEP, the displacement versus time data of individual bio-particles can be simultaneously measured in a facile manner by image analysis, without the need for averaging of the data from multiple bio-particle collection measurements over a large region. This enhances the sensitivity of our measurements towards small differences in electrophysiology of subpopulation.

Frequency-Selective Localization by Dielectrophoresis

Figure 19:
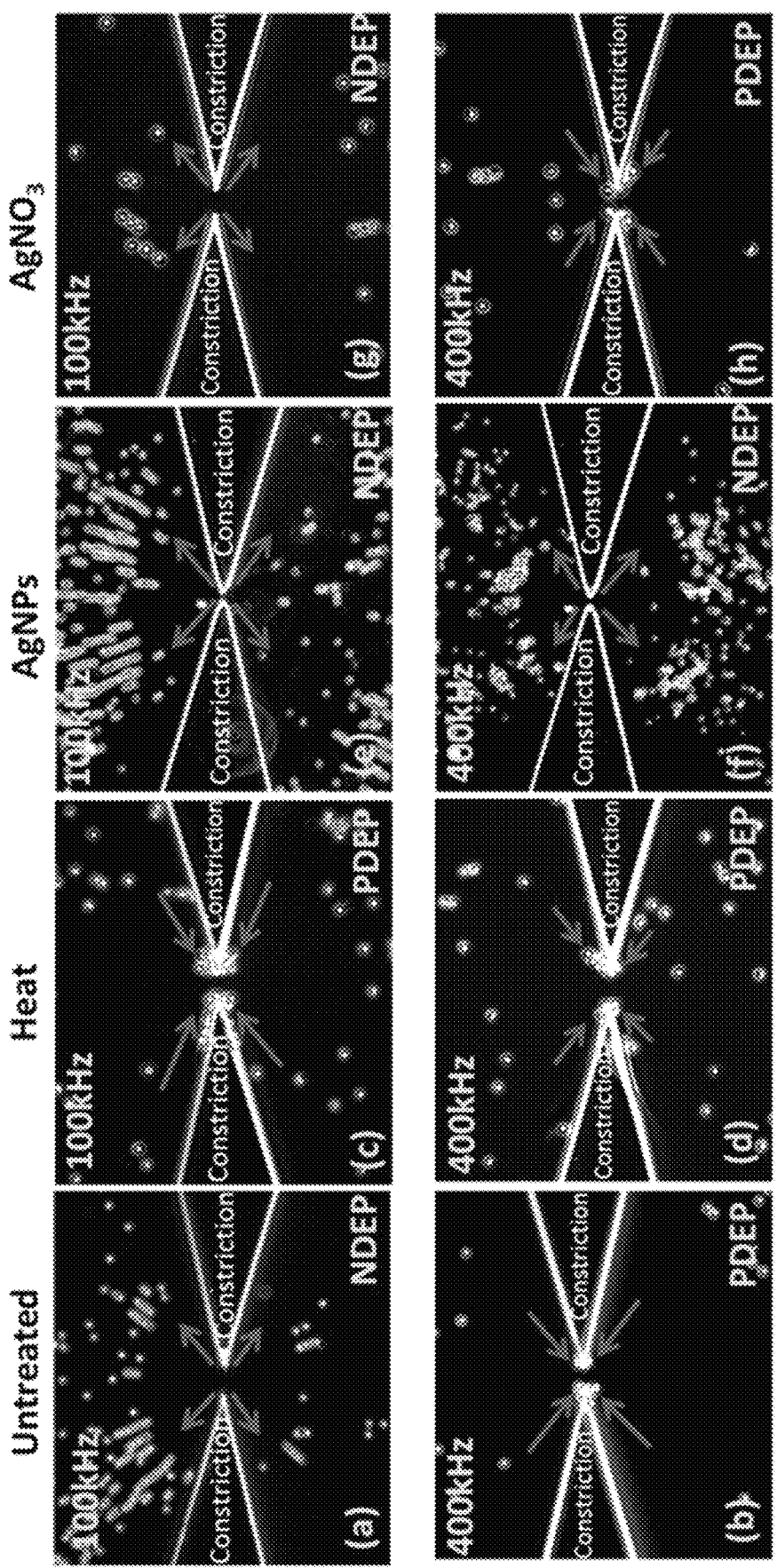
FIG. 19 depicts dielectric behavior of oocysts in the contriction region after 30 seconds of AC field: 300 $V_{pp}$ cm$^{-1}$ at 100 kHz (a, c, e, g) or 400 kHz (b, d, f, h) for: Untreated oocysts (a&b); heat-treated (90° C.) oocysts (c&d); AgNP treated oocysts (e&f); and AgNO$_3$ treated oocysts (g&h).

The DEP response of biological particles, such as *C. parvum* oocysts can be characterized using a shell model, with the shell composed of an oocyst wall of low conductivity ($\sigma_{wall}$ ~100 nS m$^{-1}$ as per ref. 28) and a core of higher conductivity due to intact sporozoites within the cytoplasm ($\sigma_{cyto}$~0.05 S m$^{-1}$ ref. 28). The oocyst can be represented in terms of an equivalent circuit composed of a low-loss capacitor of capacitance: C, to denote the oocyst wall, in series with the high-conductivity oocyst cytoplasm of resistance: R. As per RC circuit analysis, at frequencies below the inverse RC time constant, the polariz-ability and net direction of particle translation is determined by the capacitor due to the oocyst wall, which should result in negative DEP (NDEP) behavior within moderately conducting media ($\sigma_m$~0.1-10 mS m$^{-1}$), due to: $\sigma_{wall}$ (~100 nS m$^{-1}$)<$\sigma_m$(0.1-10 mS m$^{-1}$) in eqn (2). On the other hand, at frequencies above the inverse RC time constant, the high conductivity region at the oocyst core determines the DEP response, thereby causing positive DEP (PDEP) behavior, since: ($\sigma_{cyto}$ (~0.05 S m$^{-1}$)>$\sigma_m$ (0.1-10 mS m$^{-1}$) in eqn (2). At very high frequencies (~10 MHz), the response is determined by permittivity rather than conductivity, which should cause NDEP behavior, due to: $\varepsilon_{cyto}$ (~60)<$\varepsilon_m$(~80).[28] This is indeed the trend observed within FIG. 5, which shows images in the vicinity of the insulator constriction region of the device after 30 seconds of the onset of DEP behavior at ~300 V$_{pp}$ cm$^1$ field; and at frequencies of 100 kHz and 400 kHz, where the oocyst wall and the sporozoites in the oocyst cytoplasm, respectively, determine the net DEP behavior. For untreated oocysts, NDEP behavior occurs from 1 kHz onwards until ~200 kHz, as apparent from the strong translation force on the oocysts away from the constriction tip at 100 kHz (as per arrows in FIG. 19a), whereas PDEP behavior occurs from 400 kHz onwards, as apparent from trapping of the oocysts at the constriction tip (as per arrows in FIG. 19b). Upon heat treatment of the oocysts (90° C.), the disruption of the oocyst wall, as apparent from the fluorescence images in FIGS. 5g and h, affects the DEP response. The increased permeability of the oocyst wall impedes dipole formation across the oocyst wall, thereby eliminating the screening action of the capacitor and the associated NDEP behavior. Instead, crossover to PDEP behavior is observed at earlier frequencies, due to polarization of the oocyst cytoplasm, which is no longer screened by the oocyst wall at low frequencies. Hence, the onset of PDEP, which occurs from 10 kHz onwards for heat-treated oocysts, is clearly apparent at 100 kHz in FIG. 19c. At 400 kHz, PDEP behavior continues to be present, albeit at a significantly lower force level, as apparent from the fewer trapped oocysts at the constriction tip in FIG. 19d after the same 30 seconds of applied field. Following AgNP treatment, the strong NDEP response is clearly apparent at 100 kHz in FIG. 19e, indicating an unborn-promised oocyst wall, which is consistent with the fluorescence results. At 400 kHz, instead of the oocysts being directed towards the constriction tips, as observed with untreated (FIG. 19b) or heat treated oocysts (FIG. 19c), the DEP force on AgNP treated oocysts continues to remain directed away from the constrictions tips (FIG. 19t). However, the magnitude of the NDEP force at 400 kHz is lower versus that at 100 kHz, as apparent from localization of the oocysts closer to the constriction tip at 400 kHz (FIG. 19f) versus 100 kHz (FIG. 19e). For oocysts with an uncompromised wall, the DEP response at 400 kHz should be determined by the difference of cytoplasm and media conductivity. Hence, the NDEP behavior after AgNP treatment of the oocysts can be attributed to a reduction in the cytoplasm conductivity due to alteration of the sporozoites ($\sigma_{cyto}$), thereby obviating PDEP behavior, due to: ($\sigma_{cyto}-\sigma_m$)<0. In the subsequent sections we explain the NDEP behavior of AgNP treated oocysts and correlate it to alteration of sporozoites in the oocyst. Finally, based on the similarity of DEP response of AgNO$_3$ treated versus untreated oocysts at 100 kHz (FIG. 19g) and at 400 kHz (FIG. 19h), we infer that the oocysts are not significantly altered, which is consistent with the excystation results.

Characterizing Cell Electrophysiology by Dielectrophoresis

Figure 20:
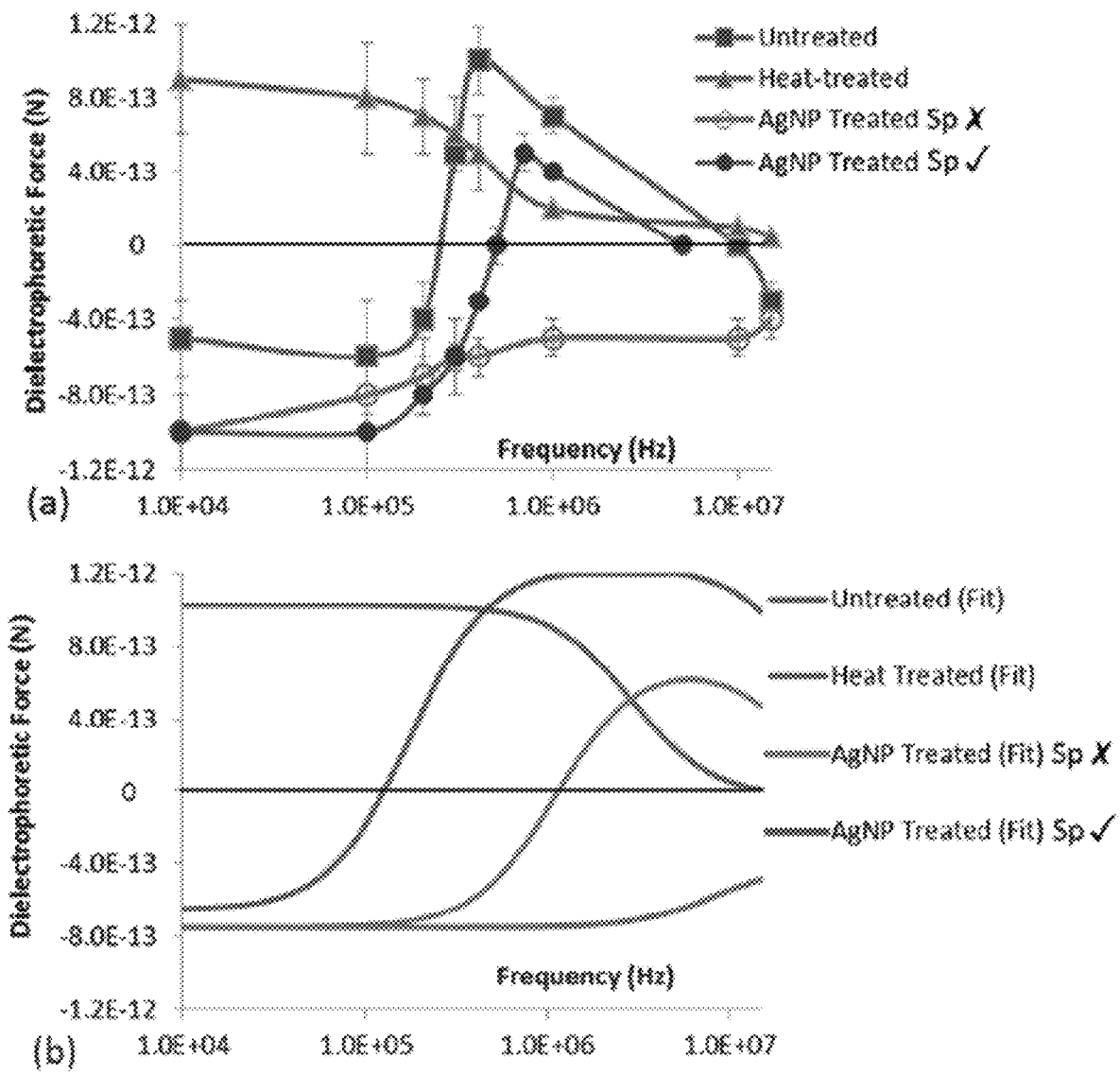
FIG. 20 depicts measured FDEP frequency responses from DEP tracking of: (a) untreated and heat treated oocysts (90° C.) at $\sigma_m$ of 2 mS m$^{-1}$ and AgNP treated oocysts at $\sigma_m$ of 10 mS m$^{-1}$. Error bars are based on velocity profiles from 20 oocysts after each treatment type. (b) The fitted force response at the respective $\sigma_m$ values is applied to characterize oocyst electrophysiology as in Table 1 below.

Based on tracking the displacement of the oocysts versus time to quantify the DEP force after normalizing for the field uniformities within the constriction device (as described within the Methods section and ESL S1†), FIG. 20a shows the frequency response of F$_{DEP}$ (symbols) for untreated, heat treated (90° C.) and AgNP treated oocysts, with a polynomial fit. For untreated oocysts, the transition from NDEP behavior at low frequencies (<100 kHz) to PDEP behavior at mid-level frequencies (>400 kHz) is apparent. For heat treated oocysts, PDEP behavior starts at successively earlier frequencies, due to loss of the field screening by the compromised oocyst wall.

For AgNP treated oocysts, we are able to identify different DEP behavior at frequencies beyond 400 kHz for sensitive oocysts with altered sporozoites (Sp X) versus persistent oocysts with intact sporozoites (Sp √), as will be described in the subsequent section. The force responses of FIG. 20a were fit to a single shell model (ESI S2†), to quantify the oocyst electro-physiology, as given by conductivity and permittivity values for the oocyst wall ($\sigma_{wall}$, $\epsilon_{wall}$) and sporozoites in the cytoplasm ($\sigma_{cyto}$, $\epsilon_{cyto}$), after each treatment. This method compares well with the crossover frequency method, without the need for measuring the spectra within media of varying conductivity (see ESI S4†). Based on the "fits" in FIG. 20b and Table 1, it is clear that heat treatment causes a steep rise in $\sigma_{wall}$, from $6\times10^{-7}$ S m$^{-1}$ for untreated oocysts to $5\times10^{-5}$ S m$^{-1}$ for heat treated oocysts. Following AgNP treatment, there is a sensitive subpopulation with altered sporozoites (Sp X) that correlates with a steeply lowered $\sigma_{cyto}$ and no changes to $\sigma_{wall}$, while the persistent subpopulation with intact sporozoites (Sp √) exhibits no significant alterations in $\sigma_{cyto}$ and $\sigma_{wall}$, in comparison to untreated oocysts. The antimicrobial action of AgNP is usually attributed to the release of silver ions and generation reactive oxygen species that damage the cell membrane or penetrate into the cells to destroy the proteins and DNA. Hence, the significantly lowered $\sigma_{cyto}$ after AgNP treatment for the subpopulation with altered sporozoites (Sp X) is attributed to cytoplasm alteration due to degraded proteins and DNA.

TABLE 1

Dielectric parameters of the oocyst wall ($\sigma_{wall}$ in S m$^{-1}$ and $\epsilon_{wall}$) and sporozoites ($\sigma_{cyto}$ in S m$^{-1}$ and $\epsilon_{cyto}$), as determined by fitting the measured DEP force response of FIG. 6

| Treatment | $\sigma_{wall}$ | $\epsilon_{wall}$ | $\sigma_{cyto}$ | $\epsilon_{cyto}$ |
|---|---|---|---|---|
| Untreated | $6 \times 10^{-7}$ | 8 | 0.055 | 55 |
| Heat-treated | $5 \times 10^{-8}$ | 8 | 0.005 | 78 |
| AgNP treated (Sp X) | $5 \times 10^{-7}$ | 5 | $5 \times 10^{-6}$ | 30 |
| AgNP treated (Sp √) | $1 \times 10^{-8}$ | 3 | 0.032 | 70 |

Separation Based on Oocyst Wall and Sporozoite Infectivity

Finally, using the quantitative force response in FIG. 20a from the DEP tracking measurements, we can identify the appropriate frequency for effectively separating the sub-populations after AgNP and heat treatment (70° C.), utilizing differences in the magnitude and direction of the DEP trapping force. This is necessary, since persistent subpopulations can form extremely small fractions of the total population. Through collection rate measurements on the separated subpopulations, the fraction with a particular electrophysiological alteration or phenotype can be quantified.

Figure 21:
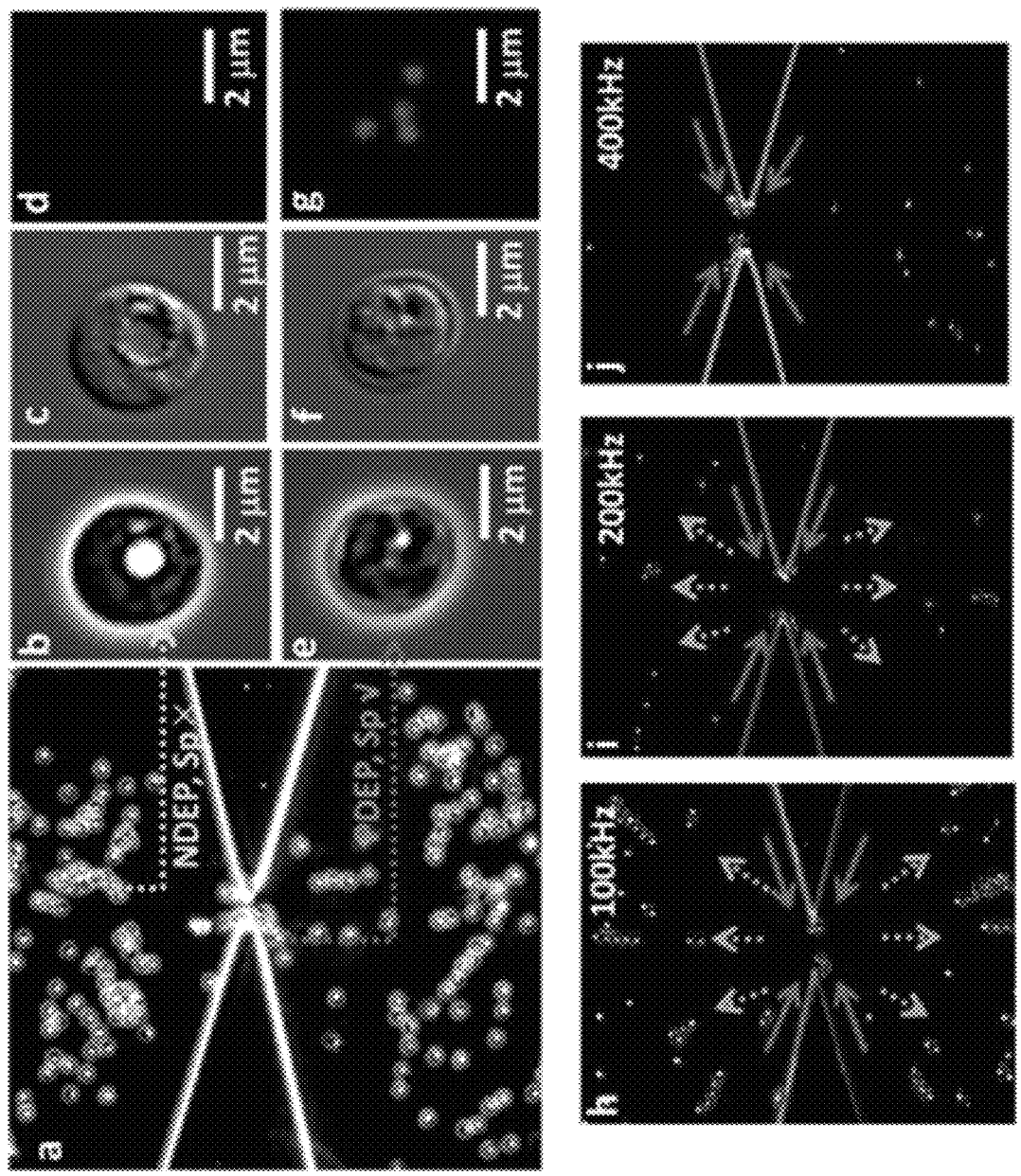
FIG. 21 depicts dielectrophoretic separation of oocysts based on sporozoite alteration (a-g) and oocyst wall integrity (h-j). (a) 300 $V_{pp}$ cm$^{-1}$ field at 700 kHz causes NDEP of oocysts with altered sporozoites (Sp X), as confirmed by absence of sporozoite structure in phase (b) and DIC images (c), and absence of DAPI signal (d). Oocysts with intact sporozoites (Sp √), as confirmed by presence of characteristic sporozoite structure in phase contrast (e) and DIC images (f), and the presence of DAPI signal (g) show PDEP trapping. (h) Separation based on oocyst wall integrity is more effective under 300 $V_{pp}$ cm$^{-1}$ field at 100 kHz, versus at: (i) 200 kHz, and (j) 400 kHz

For oocysts with altered (Sp X) versus intact sporozoites (Sp √) after AgNP treatment, a frequency of 700 kHz causes PDEP behavior for Sp √ oocysts (blue arrows), whereas Sp X oocysts experience NDEP behavior (yellow arrows), as per FIG. 21. Optical microscopy of the sub-group of AgNP treated oocysts exhibiting NDEP behavior confirms their altered sporozoites (Sp X), as apparent from absence of the banana-shaped sporozoite structure in the phase contrast (FIG. 7b) and DIC images (FIG. 21), as well as the exclusion of DAPI signal in fluo-rescence images (FIG. 21). On the other hand, the oocysts exhibiting PDEP behavior show the distinct banana-shaped sporozoite structure in the high-magnification phase contrast (FIG. 21e) and DIC (FIG. 21f) images; as well as the presence of DAPI signal in fluores-cence images (FIG. 21g). Next, we demonstrate the separation of the sub-groups with intact versus compromised oocyst walls, after heat treatment at 70° C. As per FIG. 21h-j, a lower frequency of 100 kHz, where dominance of the screening action of the oocyst wall causes NDEP behavior, is more effective at separating the respective oocyst groups versus at higher frequencies, where the net polarization behavior of the oocysts is no longer sensitive to the oocyst wall. Oocysts with uncompromised walls exhibit NDEP up to 200 kHz, whereas those with disrupted walls exhibit PDEP, starting from successively lower frequencies (depending on degree of disruption) and extending to ~400 kHz. Hence, judicious choice of the frequency can enable more effective separations through modulation of the magnitude and direction of the DEP trapping force.

Towards quantifying persistent microbial subpopulations with phenotypically different alterations after disinfection treatments and characterizing their electrophysiology, we demonstrate the utility of quantitative dielectrophoretic tracking for force measurements over a wide frequency range (10 kHz-10 MHz). Utilizing a device with insulator constrictions to localize the field and modulate the spatial extent of the field gradient so that it is symmetric across the device depth, we are able to establish a well-defined trajectory of cells under positive and negative dielectrophoresis. As a result, the simultaneous and facile tracking of velocity of single cells can be accomplished for computing the quantitative force response, which is more sensitive to electro-physiological differences from subpopulations, since there is no need for averaging over large collection regions. This quantitative force response over the 10 kHz-10 MHz frequency range is applied to characterize and separate sensitive versus persistent subpopulations that were identified by excystation and animal infectivity assays during the disinfection of *Cryptosporidium parvum*. Through correlating the force response at 0.4-1 MHz to integrity of sporozoites in the oocyst and at ≤100 kHz to the integrity of the oocyst wall, we demonstrate the separation of persistent subpopulations after AgNP treatment and heat treatment at 70° C., respectively. We envision the application of this technique for probing subtle distinctions in microbial electrophysiology after immuno-magnetic separation from large water systems. See related articles (each of which is incorporated herein by reference):

1 K. R. Allison et al., *Curr. Opin. Microbial.*, 2011, 14, 593-598.

2 O. Gefen and N. Q. Balaban, *FEMS microbiology reviews*, 2009, 33, 704-717.

3 E. J. Stewart, *J. Bacteria*, 2012, 194, 4151-4160.

4 M. Smith, *Cryptosporidium: The Analytical Challenge*, Royal Society of Chemistry 2001.

5 U. N. H. S. Programme, i Water and Sanitation in the World's Cities: Local Action for Global Goals, Earthscan Publications, London, 2003.

6 X. M. Chen et al., *N. EngL J. Med.*, 2002, 346, 1723-1731.

7 R. Dillingham and R. L. Guerrant, *Lancet*, 2004, 363, 94-95.

8 C. G. R. Kenneth and J. Ryan, *Sherris Medical microbiology: An introduction to infectious disease*, McGraw-Hill, New York, 4th edn, 2004.

9 H. V. Smith and R. A. Nichols, *Exp. Parasitol.*, 2010, 124, 61-79.

10 P. C. Okhuysen et al., *Infect. Dis.*, 1999, 180, 1275-1281.

11 M. Walker et al., *Appl Environ. Microbial.*, 2001, 67, 5526-5529.

12 J. B. Parr et al., *Am. J. Trap. Med. Hyg.*, 2007, 76, 938-942.

13 J. T. Connelly et al., *Anal. Bioanal. Chem.*, 2008, 391, 487-495.

14 N. G. Green and H. Morgan, *AC Electrokinetics: colloids and nanoparticles*, Research Studies Press Ltd., USA, 1st edn, 2002, p. 250.

15 T. B. Jones, *Electromechanics of Particles*, Cambridge University Press (1995.

16 R. Pethig, *Biomicrofluidics*, 2010, 4, 022811.

17 S. Bhattacharya et al., *Electrophoresis*, 2011, 32, 2550-2558.

18 A. Salmanzadeh et al., *Lab Chip*, 2012, 12, 182-189.

19 B. H. Lapizco-Encinas et al., *J. Microbial. Methods*, 2005, 62, 317-326.

20 H. Morgan et al., *Biophys. J.*, 1999, 77, 516-525.

21 N. Swami et al., *Lab Chip*, 2009, 9, 3212-3220.

22 K. T. Liao et al., *Electrophoresis*, 2012, 33, 1958-1966.

23 K. F. Hoettges et al., *Anal. Chem.*, 2008, 80, 2063-2068.

24 W. A. Graff et al., *Lab Chip*, 2012, 12, 1327-1331.

25 V. Chaurey et al., *Biomicrofluidics*, 2012, 6, 012806: 1-14.

26 C. C. Chung et al., *Anal. Chem.*, 2012, 84, 3347-3354.

27 B. G. Hawkins et al., *Anal. Chem.*, 2011, 83, 3507-3515.

28 H. Narayanan Unni et al., *Biomicrofluidics*, 2012, 6, 12805-1280514.

29 C. M. Quinn et al., *Lett. Appl. Microbiol.*, 1996, 22, 224-228.

30 A. D. Goater et al., *J. Phys. D: Appl, Phys.*, 1997, 30, 5.

31 C. G. Dalton et al., *Colloids Surf., A*, 2001, 195, 6.

32 C. Marambio-Jones and E. M. V. Hoek, *J. Nanopart. Res.*, 2010, 12, 1531-1551.

33 E. Fauss et al., *Colloids Surf, B*, 2014, 113, 77-84.

34 V. A. Oyanedel-Craver and J. A. Smith, *Environ. Sci. Technol*, 2008, 42, 927-933.

35 B. De Gusseme et al., *Water Res.*, 2011, 45, 1856-1864.

36 Y. H. Lv et al., *J. Membr. Sci.*, 2009, 331, 50-56.

37 J. R. Morones et al., *Nanotechnology*, 2005, 16, 2346-2353.

38 D. J. Bakewell and H. Morgan, *Meas. Sci. Technol.*, 2004, 15, 254-266.

39 F. H. Labeed et al., *Biochim. Biophys. Acta, Gen. Subj.*, 2006, 1760, 922-929.

40 Z. Gagnon et al., *Electrophoresis*, 2008, 29, 2272-2279.

41 Z. Gagnon et al., *Biomicrofluidics*, 2009, 3, 044108.

42 M. Castellarnau et al., *Biophys. J.*, 2006, 91, 3937-3945.

43 A. Di Biasio et al., *Biophys. J.*, 2010, 99, 163-174.

44 K. V. Kaler and T. B. Jones, *Biophys, J.*, 1990, 57, 173182.

45 H. Watarai et al., *Langmuir*, 1997, 13, 2417-2420.

46 H. S. Moyed and K. P. Bertrand, *Bacterial.*, 1983, 155, 768775.

47 R. Fayer, *Appl Environ. Microbiol*, 1994, 60, 2732-2735.

48 A. T. Campbell et al., *Appl Environ. Microbial.*, 1992, 58, 3488-3493.

49 L. J. Anguish and W. C. Ghiorse, *Appl Environ. Microbial.*, 1997, 63, 724-733.

50 V. Chaurey et al., *Langmuir*, 2010, 26, 19022-19026.

51 Z. R. Gagnon, *Electrophoresis*, 2011, 32, 2466-2487.

The above examples are included for illustrative purposes only and is not intended to limit the scope of the disclosure. Many variations to those methods, systems, and devices described above are possible. Since modifications and variations to the examples described above will be apparent to those of skill in this art, it is intended that this invention be limited only by the scope of the appended claims. One skilled in the art will appreciate further features and advantages of the presently disclosed methods, systems and devices based on the above-described embodiments. Accordingly, the presently disclosed methods, systems and devices are not to be limited by what has been particularly shown and described, except as indicated by the appended claims. All publications and references cited herein are expressly incorporated herein by reference in their entirety or for purposes of which they are specifically cited.

We claim:

1. A system comprising a paired and counter-phase amplifier unit coupled to electrodes in a microfluidic device, the system comprising:
   the microfluidic device comprising:
      an elongate channel having an inlet defining a first end, and an outlet defining a second end, and having at least one spatially localized high-field region configured to provide translation of a particle or cell in an insulator dielectrophoresis (iDEP) control operation; and
      the electrodes comprising a first electrode located in the inlet and a second electrode located in the outlet, the electrodes being configured to generate a spatially non-uniform electric field at the at least one spatially localized high-field region;
   the paired and counter-phase amplifier unit comprising:
      a wideband splitter unit adapted to generate counter-phase input signals comprising a first signal and a second signal from an input signal, wherein the second signal is 180° phase-shifted from the first signal; and
      wideband power amplifiers comprising a first amplifier and a second amplifier, wherein an input of the first amplifier is coupled to a first output of the wideband splitter unit to receive the first signal, and wherein an input of the second amplifier is coupled to a second output of the wideband splitter unit to receive the second signal, and wherein the first amplifier and second amplifier are configured to generate counter-phase output signals applied to the first and second electrodes by amplifying a voltage difference between the first signal and the second signal to an output voltage twice that of individual outputs of the first and second signals at a range between, and inclusive of, 20 V and 1000 V, and wherein the counter-phase output signals have a frequency between, and inclusive of, 0.01 MHz and 10 MHz; and
   an adjustable power supply operably connected with the paired and counter-phase amplifier unit and configured for feedback control for a constant power output for the insulator dielectrophoresis control operation.

2. The system of claim 1, wherein each of the first and second electrodes is located outside the at least one spatially localized high-field region.

3. The system of claim 2, wherein the system is configured for single particle tracking.

4. The system of claim 3, wherein the system is configured for single particle dielectrophoretic translation of bioparticles under electric fields.

5. The system of claim 4, wherein the paired and counter-phase amplifier unit is operably connected for electrical stimulation and measurements with the microfluidic device and the single particle trapping is performed in one or more insulator constriction regions in the microfluidic device.

6. The system of claim 1, wherein the first and second amplifiers are provided with the first and second signals each having a same amplitude.

7. The system of claim 1, wherein the first and second amplifiers are each operational amplifiers (Op-amps).

8. The system of claim 1, wherein the wideband splitter unit comprises super-fast low-power Op-amps.

9. The system of claim 1, further comprising an attenuator and a controllable signal generator, wherein the controllable signal generator is connected to the first amplifier and second amplifiers to provide a source signal for the counter-phase output signals.

10. The system of claim 1, wherein each of the first and second amplifier has a slew rate of over 2500 V/µs to provide the counter-phase output signals with a slew rate of over 5000 V/µs.

11. The system of claim 1, wherein each of the first and second amplifier has a slew rate of over 3000 V/µs to provide the counter-phase output signals with a slew rate of over 6000 V/µs.

12. The system of claim 1, wherein each of the first and second amplifier has a slew rate of over 4000 V/µs to provide the counter-phase output signals with a slew rate of over 8000 V/µs.

13. The system of claim 1, wherein each of the first and second amplifier has a slew rate of 5000 V/µs as to provide the counter-phase output signals with a slew rate of 1000 V/µs.

14. The system of claim 1, wherein the paired and counter-phase amplifier unit is operably connected with the microfluidic device and is configured to output at a high voltage and a high frequency selected from the group consisting of: 300 Vpp at 100 KHz, 300 Vpp at 1 MHz, 300 Vpp at 3 MHz, and 250 Vpp at 5 MHz.

15. The system of claim 1, wherein the adjustable power supply is self-adjustable, via the feedback control, for dynamic modulation of supply voltages in response to measurements from the microfluidic device.

16. The system of claim 15, wherein the paired and counter-phase amplifier unit is configured to deliver the constant power output for avoiding over-heating and signal distortion due to signal saturation.

17. The system of claim 16, wherein the paired and counter-phase amplifier unit is configured to reduce dynamic distortions and parasitic voltage drops within the counter-phase output signals of the first and second.

18. The system of claim 1, wherein the at least one spatially localized high-field region comprises insulator constrictions or field non-uniformities.

19. The system of claim 18, wherein the system is configured to position and measure cells within respective media in the at least one spatially localized high field region.

* * * * *

UNITED STATES PATENT AND TRADEMARK OFFICE
CERTIFICATE OF CORRECTION

| | | |
|---|---|---|
| PATENT NO. | : 11,339,417 B2 | Page 1 of 1 |
| APPLICATION NO. | : 15/515528 | |
| DATED | : May 24, 2022 | |
| INVENTOR(S) | : Nathan Swami et al. | |

It is certified that error appears in the above-identified patent and that said Letters Patent is hereby corrected as shown below:

On the Title Page

Item (72) should read:
(72) Inventors: Nathan Swami, Charlottesville, VA (US); Ali Rohani, Charlottesville, VA (US); Vahid Farmehini, Charlottesville, VA (US); Walter Varhue, Charlottesville, VA (US)

Signed and Sealed this
Second Day of August, 2022

Katherine Kelly Vidal
*Director of the United States Patent and Trademark Office*